US010070695B2

(12) United States Patent
Burns et al.

(10) Patent No.: US 10,070,695 B2
(45) Date of Patent: Sep. 11, 2018

(54) TIGHTENING MECHANISMS AND APPLICATIONS INCLUDING THE SAME

(71) Applicant: Boa Technology Inc., Denver, CO (US)

(72) Inventors: Robert E. Burns, Denver, CO (US); Gary R. Hammerslag, Steamboat Springs, CO (US); Eric C. Irwin, Denver, CO (US); Kristopher C. Lovett, Denver, CO (US); Michael J. Nickel, Golden, CO (US); Mark S. Soderberg, Conifer, CO (US)

(73) Assignee: Boa Technology Inc., Denver, CO (US)

( * ) Notice: Subject to any disclaimer, the term of this patent is extended or adjusted under 35 U.S.C. 154(b) by 7 days.

(21) Appl. No.: 15/231,562

(22) Filed: Aug. 8, 2016

(65) Prior Publication Data

US 2017/0027287 A1 Feb. 2, 2017

Related U.S. Application Data

(63) Continuation-in-part of application No. 15/191,281, filed on Jun. 23, 2016, which is a continuation-in-part
(Continued)

(51) Int. Cl.
*A43C 11/00* (2006.01)
*A43C 11/16* (2006.01)
(Continued)

(52) U.S. Cl.
CPC .............. *A43C 11/165* (2013.01); *A43C 1/04* (2013.01); *A43C 11/20* (2013.01)

(58) Field of Classification Search
CPC .......... A43C 11/165; A43C 11/20; A43C 1/04
See application file for complete search history.

(56) References Cited

U.S. PATENT DOCUMENTS

| 59,332 A | 10/1866 | White et al. |
| 80,834 A | 8/1868 | Prussia |
| (Continued) | | |

FOREIGN PATENT DOCUMENTS

| CA | 2112789 | 8/1994 |
| CA | 2114387 | 8/1994 |
| (Continued) | | |

OTHER PUBLICATIONS

U.S. Appl. No. 09/956,601, filed Sep. 18, 2001, Hammerslag.
(Continued)

*Primary Examiner* — David M Upchurch
(74) *Attorney, Agent, or Firm* — Kilpatrick Townsend & Stockton LLP

(57) ABSTRACT

This disclosure relates to articles that include a tightening mechanism, such as reel-based lace tightening mechanism, configured to tighten the article by rotation of a knob. The articles can include a concealing portion that is configured to conceal or protect at least a portion of the tightening mechanism, such as the knob. The concealing portion can be configured to prevent unintentional actuation of the tightening mechanism, such as during contact sports. The concealing portion can be configured to hide the tightening mechanism from view to improve the visual appearance of the article. The concealing portion can be collapsible such that a user can press the concealing portion down to expose the knob of the tightening mechanism.

11 Claims, 68 Drawing Sheets

Related U.S. Application Data of application No. 13/973,917, filed on Aug. 22, 2013, now Pat. No. 9,408,437, which is a continuation of application No. 13/829,601, filed on Mar. 14, 2013, now Pat. No. 9,375,053, which is a continuation of application No. 13/098,276, filed on Apr. 29, 2011, now Pat. No. 8,516,662.

(60) Provisional application No. 61/611,418, filed on Mar. 15, 2012, provisional application No. 61/330,129, filed on Apr. 30, 2010.

(51) Int. Cl.
*A43C 1/04* (2006.01)
*A43C 11/20* (2006.01)

(56) References Cited

U.S. PATENT DOCUMENTS

| | | | |
|---|---|---|---|
| 117,530 | A | 8/1871 | Foote |
| 228,946 | A | 6/1880 | Schulz |
| 230,759 | A | 8/1880 | Drummond |
| 379,113 | A | 3/1888 | Hibberd |
| 746,563 | A | 12/1903 | McMahon |
| 819,993 | A | 5/1906 | Haws et al. |
| 908,704 | A | 1/1909 | Sprinkle |
| 1,060,422 | A | 4/1913 | Bowdish |
| 1,062,511 | A | 5/1913 | Short |
| 1,083,775 | A | 1/1914 | Thomas |
| 1,090,438 | A | 3/1914 | Worth et al. |
| 1,170,472 | A | 2/1916 | Barber |
| 1,288,859 | A | 12/1918 | Feller et al. |
| 1,390,991 | A | 9/1921 | Fotchuk |
| 1,393,188 | A | 10/1921 | Whiteman |
| 1,412,486 | A | 4/1922 | Paine |
| 1,416,203 | A | 5/1922 | Hobson |
| 1,429,657 | A | 9/1922 | Trawinski |
| 1,481,903 | A | 4/1923 | Hart |
| 1,466,673 | A | 9/1923 | Solomon et al. |
| 1,469,661 | A | 10/1923 | Migita |
| 1,530,713 | A | 2/1924 | Clark |
| 1,502,919 | A | 7/1924 | Seib |
| 1,862,047 | A | 6/1932 | Boulet et al. |
| 1,995,243 | A | 6/1934 | Clarke |
| 2,088,851 | A | 8/1937 | Gantenbein |
| 2,109,751 | A | 3/1938 | Matthias et al. |
| 2,124,310 | A | 9/1938 | Murr, Jr. |
| 2,316,102 | A | 4/1943 | Preston |
| 2,539,026 | A | 1/1951 | Mangold |
| 2,611,940 | A | 9/1952 | Cairns |
| 2,673,381 | A | 3/1954 | Dueker |
| 2,907,086 | A | 10/1959 | Ord |
| 2,991,523 | A | 7/1961 | Del Conte |
| 3,028,602 | A | 4/1962 | Miller |
| 3,035,319 | A | 5/1962 | Wolff |
| 3,106,003 | A | 10/1963 | Herdman |
| 3,112,545 | A | 12/1963 | Williams |
| 3,122,810 | A | 3/1964 | Lawrence et al. |
| 3,163,900 | A | 1/1965 | Martin |
| D200,394 | S | 2/1965 | Hakim |
| 3,169,325 | A | 2/1965 | Fesl |
| 3,193,950 | A | 7/1965 | Shu-Lien Liou |
| 3,197,155 | A | 7/1965 | Chow |
| 3,221,384 | A | 12/1965 | Aufenacker |
| 3,276,090 | A | 10/1966 | Nigon |
| D206,146 | S | 11/1966 | Hendershot |
| 3,345,707 | A | 10/1967 | Rita |
| D210,649 | S | 4/1968 | Getgay |
| 3,401,437 | A | 9/1968 | Christpohersen |
| 3,430,303 | A | 3/1969 | Perrin et al. |
| 3,491,465 | A | 1/1970 | Martin |
| 3,545,106 | A | 12/1970 | Martin |
| 3,618,232 | A | 11/1971 | Shnuriwsky |
| 3,668,791 | A | 6/1972 | Salzman et al. |
| 3,678,539 | A | 7/1972 | Group |
| 3,703,775 | A | 11/1972 | Gatti |
| 3,729,779 | A | 5/1973 | Porth |
| 3,738,027 | A | 6/1973 | Schoch |
| 3,793,749 | A | 2/1974 | Gertsch et al. |
| 3,808,644 | A | 5/1974 | Schoch |
| 3,934,346 | A | 1/1976 | Sasaki et al. |
| 3,975,838 | A | 8/1976 | Martin |
| 4,084,267 | A | 4/1978 | Zadina |
| 4,130,949 | A | 12/1978 | Seidel |
| 4,142,307 | A | 3/1979 | Martin |
| 4,227,322 | A | 10/1980 | Annovi |
| 4,261,081 | A | 4/1981 | Lott |
| 4,267,622 | A | 5/1981 | Burnett-Johnston |
| 4,408,403 | A | 10/1983 | Martin |
| 4,417,703 | A | 11/1983 | Weinhold |
| 4,433,456 | A | 2/1984 | Baggio |
| 4,463,761 | A | 8/1984 | Pols et al. |
| 4,480,395 | A | 11/1984 | Schoch |
| 4,507,878 | A | 4/1985 | Semouha |
| 4,516,576 | A | 5/1985 | Kirchner |
| 4,551,932 | A | 11/1985 | Schoch |
| 4,555,830 | A | 12/1985 | Petrini et al. |
| 4,574,500 | A * | 3/1986 | Aldinio .............. A43C 11/16 24/68 SK |
| 4,616,432 | A | 10/1986 | Bunch et al. |
| 4,616,524 | A | 10/1986 | Biodia |
| 4,619,057 | A | 10/1986 | Sartor et al. |
| 4,620,378 | A | 11/1986 | Sartor |
| 4,631,839 | A | 12/1986 | Bonetti et al. |
| 4,631,840 | A | 12/1986 | Gamm |
| 4,633,599 | A * | 1/1987 | Morell .............. A43C 11/16 24/68 SK |
| 4,644,938 | A | 2/1987 | Yates et al. |
| 4,654,985 | A | 4/1987 | Chalmers |
| 4,660,300 | A | 4/1987 | Morell et al. |
| 4,660,302 | A | 4/1987 | Arieh et al. |
| 4,680,878 | A | 7/1987 | Pozzobon et al. |
| 4,719,670 | A * | 1/1988 | Kurt .............. A43C 11/16 24/68 SK |
| 4,719,709 | A * | 1/1988 | Vaccari .............. A43B 5/0433 36/117.8 |
| 4,719,710 | A | 1/1988 | Pozzobon |
| 4,722,477 | A | 2/1988 | Floyd |
| 4,741,115 | A | 5/1988 | Pozzobon |
| 4,748,726 | A | 6/1988 | Schoch |
| 4,760,653 | A | 8/1988 | Baggio |
| 4,780,969 | A | 11/1988 | White, Jr. |
| 4,787,124 | A | 11/1988 | Pozzobon et al. |
| 4,790,081 | A | 12/1988 | Benoit et al. |
| 4,796,829 | A | 1/1989 | Pozzobon et al. |
| 4,799,297 | A | 1/1989 | Baggio et al. |
| 4,802,291 | A | 2/1989 | Sailor |
| 4,811,503 | A | 3/1989 | Lwama |
| 4,826,098 | A | 5/1989 | Pozzobon et al. |
| 4,841,649 | A | 6/1989 | Baggio et al. |
| 4,856,207 | A | 8/1989 | Datson |
| 4,862,878 | A | 9/1989 | Davison |
| 4,870,723 | A | 10/1989 | Pozzobon et al. |
| 4,870,761 | A | 10/1989 | Tracy |
| 4,884,760 | A | 12/1989 | Baggio et al. |
| 4,901,938 | A | 2/1990 | Cantley et al. |
| 4,924,605 | A | 5/1990 | Spademan |
| D308,282 | S | 6/1990 | Bergman et al. |
| 4,937,953 | A | 7/1990 | Walkhoff |
| 4,961,544 | A | 10/1990 | Biodia |
| 4,979,953 | A | 12/1990 | Spence |
| 4,989,805 | A | 2/1991 | Burke |
| 5,001,817 | A | 3/1991 | De Bortoli et al. |
| 5,016,327 | A | 5/1991 | Klausner |
| 5,042,177 | A | 8/1991 | Schoch |
| 5,062,225 | A | 11/1991 | Gorza |
| 5,065,480 | A | 11/1991 | DeBortoli |
| 5,065,481 | A | 11/1991 | Walkhoff |
| 5,108,216 | A | 4/1992 | Geyer et al. |
| 5,117,567 | A | 6/1992 | Berger |
| 5,152,038 | A | 10/1992 | Schoch |
| 5,157,813 | A | 10/1992 | Carroll |
| 5,158,428 | A | 10/1992 | Gessner et al. |
| 5,177,882 | A | 1/1993 | Berger |

(56) References Cited

U.S. PATENT DOCUMENTS

| | | |
|---|---|---|
| 5,181,331 A | 1/1993 | Berger |
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |
| 5,315,741 A | 5/1994 | Debberke |
| 5,319,868 A * | 6/1994 | Hallenbeck ............ A43C 11/00 36/50.1 |
| 5,319,869 A | 6/1994 | McDonald et al. |
| 5,325,613 A | 7/1994 | Sussmann |
| 5,327,662 A * | 7/1994 | Hallenbeck ............ A43C 11/00 36/50.1 |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A | 1/2000 | Lai |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| 6,195,914 B1 * | 3/2001 | Otis ...................... A43B 3/105 36/11.5 |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| 6,311,633 B1 | 11/2001 | Keire |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| 6,606,804 B2 | 8/2003 | Kaneko et al. |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,899,720 B1 | 5/2005 | McMillan |
| 6,922,917 B2 | 8/2005 | Kerns et al. |
| 6,938,913 B2 | 9/2005 | Elkington |
| 6,945,543 B2 | 9/2005 | De Bertoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,367,522 B2 | 5/2008 | Chen |
| 7,386,947 B2 | 6/2008 | Martin |
| 7,392,602 B2 | 7/2008 | Reagan et al. |
| 7,401,423 B2 | 7/2008 | Reagan et al. |
| 7,490,458 B2 | 2/2009 | Ford |
| 7,568,298 B2 | 8/2009 | Kerns |
| 7,582,102 B2 | 9/2009 | Heinz et al. |
| 7,584,528 B2 | 9/2009 | Hu |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |
| 7,624,517 B2 | 12/2009 | Smith |
| 7,648,404 B1 * | 1/2010 | Martin ................ B63B 35/7936 114/39.19 |
| 7,650,705 B2 | 1/2010 | Donnadieu et al. |
| 7,694,354 B2 | 4/2010 | Philpott et al. |

(56) References Cited

U.S. PATENT DOCUMENTS

| | | |
|---|---|---|
| 7,752,774 B2 | 7/2010 | Ussher |
| 7,757,412 B2 | 7/2010 | Farys |
| 7,774,956 B2 | 8/2010 | Dua et al. |
| D626,322 S | 11/2010 | Servettaz |
| 7,841,106 B2 | 11/2010 | Farys |
| 7,871,334 B2 | 1/2011 | Young et al. |
| 7,877,845 B2 | 2/2011 | Signori |
| 7,900,378 B1 * | 3/2011 | Busse ............... A43B 23/029 36/29 |
| 7,908,769 B2 | 3/2011 | Pellegrini |
| 7,947,061 B1 | 5/2011 | Reis |
| 7,950,112 B2 | 5/2011 | Hammerslag et al. |
| 7,954,204 B2 | 6/2011 | Hammerslag et al. |
| 7,963,049 B2 | 6/2011 | Messmer |
| 7,992,261 B2 | 8/2011 | Hammerslag et al. |
| D646,790 S | 10/2011 | Castillo et al. |
| 8,056,150 B2 | 11/2011 | Stokes et al. |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,257,293 B2 | 9/2012 | Ingimundarson et al. |
| 8,266,827 B2 | 9/2012 | Dojan et al. |
| 8,277,401 B2 | 10/2012 | Hammerslag et al. |
| 8,302,329 B2 | 11/2012 | Hurd et al. |
| 8,303,527 B2 * | 11/2012 | Joseph ............... A61F 5/01 128/869 |
| 8,308,098 B2 | 11/2012 | Chen |
| 8,353,087 B2 | 1/2013 | Chen |
| 8,353,088 B2 | 1/2013 | Ha |
| D677,045 S | 3/2013 | Voskuil |
| D679,019 S | 3/2013 | Siddle et al. |
| 8,434,200 B2 | 5/2013 | Chen |
| 8,490,299 B2 | 7/2013 | Dua et al. |
| 8,516,662 B2 | 8/2013 | Goodman et al. |
| 8,578,632 B2 | 11/2013 | Bell et al. |
| 8,652,164 B1 | 2/2014 | Aston |
| 8,713,820 B2 | 5/2014 | Kerns et al. |
| 8,984,719 B2 | 3/2015 | Soderberg et al. |
| 9,072,341 B2 | 7/2015 | Jungkind |
| D735,987 S | 8/2015 | Hsu |
| 9,101,181 B2 | 8/2015 | Soderberg et al. |
| 9,125,455 B2 | 9/2015 | Kerns et al. |
| 9,138,030 B2 | 9/2015 | Soderberg et al. |
| 9,375,053 B2 | 6/2016 | Burns et al. |
| 9,408,437 B2 | 8/2016 | Goodman et al. |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Salomon |
| 2002/0148142 A1 | 10/2002 | Holzer et al. |
| 2002/0166260 A1 | 11/2002 | Borsoi |
| 2002/0178548 A1 | 12/2002 | Freed |
| 2003/0079376 A1 | 5/2003 | Mathieu |
| 2003/0144620 A1 | 7/2003 | Sieller |
| 2003/0150135 A1 | 8/2003 | Liu |
| 2003/0177662 A1 | 9/2003 | Elkington et al. |
| 2003/0204938 A1 | 11/2003 | Hammerslag |
| 2004/0041452 A1 | 3/2004 | Williams |
| 2004/0211039 A1 | 10/2004 | Livingston |
| 2005/0054962 A1 | 3/2005 | Bradshaw |
| 2005/0060912 A1 | 3/2005 | Holzer et al. |
| 2005/0081339 A1 | 4/2005 | Sakabayashi |
| 2005/0081403 A1 | 4/2005 | Mathieu |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0172463 A1 | 8/2005 | Rolla |
| 2005/0184186 A1 | 8/2005 | Tsoi et al. |
| 2005/0198866 A1 | 9/2005 | Wiper et al. |
| 2006/0135901 A1 | 6/2006 | Ingimundarson et al. |
| 2006/0156517 A1 * | 7/2006 | Hammerslag ............ A43B 5/16 24/68 SK |
| 2006/0179685 A1 | 8/2006 | Borel et al. |
| 2006/0185193 A1 | 8/2006 | Pellegrini |
| 2006/0287627 A1 | 12/2006 | Johnson |
| 2007/0006489 A1 | 1/2007 | Case, Jr. et al. |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 * | 7/2007 | Sodeberg ............... A43C 1/00 36/50.5 |
| 2008/0016717 A1 | 1/2008 | Ruban |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0068204 A1 | 3/2008 | Carmen et al. |
| 2008/0083135 A1 | 4/2008 | Hammerslag et al. |
| 2008/0092279 A1 | 4/2008 | Chiang |
| 2008/0172848 A1 | 7/2008 | Chen |
| 2008/0196224 A1 * | 8/2008 | Hu ...................... A43C 11/16 24/68 SK |
| 2009/0019734 A1 | 1/2009 | Reagan et al. |
| 2009/0071041 A1 | 3/2009 | Hooper |
| 2009/0090029 A1 | 4/2009 | Kishino |
| 2009/0172928 A1 | 7/2009 | Messmer et al. |
| 2009/0184189 A1 | 7/2009 | Soderberg et al. |
| 2009/0272007 A1 | 11/2009 | Beers et al. |
| 2009/0277043 A1 | 11/2009 | Graser et al. |
| 2010/0064547 A1 | 3/2010 | Kaplan |
| 2010/0101061 A1 | 4/2010 | Ha |
| 2010/0139057 A1 | 6/2010 | Soderberg et al. |
| 2010/0154254 A1 | 6/2010 | Fletcher |
| 2010/0175163 A1 | 7/2010 | Litke |
| 2010/0251524 A1 | 10/2010 | Chen |
| 2010/0299959 A1 | 12/2010 | Hammerslag |
| 2010/0319216 A1 | 12/2010 | Grenzke et al. |
| 2011/0000173 A1 | 1/2011 | Lander |
| 2011/0071647 A1 | 3/2011 | Mahon |
| 2011/0162236 A1 | 7/2011 | Voskuil et al. |
| 2011/0167543 A1 | 7/2011 | Kovacevich et al. |
| 2011/0191992 A1 | 8/2011 | Chen |
| 2011/0197362 A1 | 8/2011 | Chella et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005995 A1 | 1/2012 | Emery |
| 2012/0023717 A1 | 2/2012 | Chen |
| 2012/0101417 A1 | 4/2012 | Joseph |
| 2012/0102783 A1 | 5/2012 | Swigart et al. |
| 2012/0138882 A1 | 6/2012 | Moore et al. |
| 2012/0157902 A1 | 6/2012 | Castillo et al. |
| 2012/0167290 A1 | 7/2012 | Kovacevich et al. |
| 2012/0174437 A1 | 7/2012 | Heard |
| 2012/0228419 A1 | 9/2012 | Chen |
| 2012/0246974 A1 | 10/2012 | Hammerslag et al. |
| 2012/0310273 A1 | 12/2012 | Thorpe |
| 2013/0012856 A1 | 1/2013 | Hammerslag et al. |
| 2013/0014359 A1 | 1/2013 | Chen |
| 2013/0019501 A1 | 1/2013 | Gerber |
| 2013/0025100 A1 | 1/2013 | Ha |
| 2013/0091667 A1 | 4/2013 | Chen |
| 2013/0092780 A1 | 4/2013 | Soderberg et al. |
| 2013/0277485 A1 | 10/2013 | Soderberg et al. |
| 2013/0312293 A1 | 11/2013 | Gerber |
| 2013/0340283 A1 | 12/2013 | Bell et al. |
| 2013/0345612 A1 | 12/2013 | Bannister et al. |
| 2014/0082963 A1 | 3/2014 | Beers |
| 2014/0094728 A1 | 4/2014 | Soderberg et al. |
| 2014/0117140 A1 | 5/2014 | Goodman et al. |
| 2014/0123440 A1 | 5/2014 | Capra et al. |

(56) References Cited

U.S. PATENT DOCUMENTS

| | | |
|---|---|---|
| 2014/0123449 A1 | 5/2014 | Soderberg et al. |
| 2014/0208550 A1 | 7/2014 | Neiley |
| 2014/0221889 A1 | 8/2014 | Burns et al. |
| 2014/0290016 A1 | 10/2014 | Lovett et al. |
| 2014/0359981 A1 | 12/2014 | Cotterman et al. |
| 2015/0007422 A1 | 1/2015 | Cavanagh et al. |
| 2015/0014463 A1 | 1/2015 | Converse et al. |
| 2015/0026936 A1 | 1/2015 | Kerns et al. |
| 2015/0033519 A1 | 2/2015 | Hammerslag et al. |
| 2015/0059206 A1 | 3/2015 | Lovett et al. |
| 2015/0076272 A1 | 3/2015 | Trudel et al. |
| 2015/0089779 A1 | 4/2015 | Lawrence et al. |
| 2015/0089835 A1 | 4/2015 | Hammerslag et al. |
| 2015/0101160 A1 | 4/2015 | Soderberg et al. |
| 2015/0150705 A1 | 6/2015 | Capra et al. |
| 2015/0151070 A1 | 6/2015 | Capra et al. |
| 2015/0190262 A1 | 7/2015 | Capra et al. |
| 2015/0223608 A1 | 8/2015 | Capra et al. |
| 2015/0237962 A1 | 8/2015 | Soderberg et al. |
| 2015/0335458 A1 | 11/2015 | Romo |

FOREIGN PATENT DOCUMENTS

| | | |
|---|---|---|
| CH | 199766 | 9/1938 |
| CH | 204 834 A | 5/1939 |
| CN | 2613167 | 4/2004 |
| CN | 201015448 | 2/2008 |
| DE | 641976 | 2/1937 |
| DE | 23 41 658 | 3/1974 |
| DE | 29 00 077 A1 | 7/1980 |
| DE | 31 01 952 A1 | 9/1982 |
| DE | 38 13 470 | 11/1989 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 2/1995 |
| DE | 29503552.8 | 4/1995 |
| DE | 196 24 553 | 1/1998 |
| DE | 19945045 A1 | 3/2001 |
| DE | 20 2010 000 354 U1 | 6/2010 |
| DE | 11 2013 005 273 T5 | 9/2015 |
| EP | 0 056 953 | 8/1982 |
| EP | 0 099 504 | 2/1984 |
| EP | 0 123 050 | 10/1984 |
| EP | 0 155 596 | 9/1985 |
| EP | 0 201 051 | 11/1986 |
| EP | 0 255 869 | 2/1988 |
| EP | 0 393 380 | 10/1990 |
| EP | 0 589 232 A1 | 3/1994 |
| EP | 0 589 233 A1 | 3/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 734 622 A1 | 10/1996 |
| EP | 0 848 917 | 6/1998 |
| EP | 0 923 965 | 6/1999 |
| EP | 0 937 467 | 8/1999 |
| EP | 1163860 | 12/2001 |
| EP | 1 219 195 | 7/2002 |
| EP | 1 236 412 A | 9/2002 |
| EP | 2298107 B1 | 3/2011 |
| EP | 2359708 | 8/2011 |
| FR | 1 404 799 | 7/1965 |
| FR | 2 019 991 A | 7/1970 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| IT | 2003 A 000197 | 4/2003 |
| IT | 2003 A 000198 | 3/2005 |
| JP | 51-121375 | 10/1976 |
| JP | 53-124987 | 3/1977 |
| JP | 54-108125 | 2/1978 |
| JP | H02-236025 | 9/1990 |
| JP | 6-284906 | 2/1996 |
| JP | 3030988 | 11/1996 |
| JP | 3031760 | 12/1996 |
| JP | 10-199366 | 7/1998 |
| JP | 2004-016732 | 1/2004 |
| JP | 2004-041666 | 2/2004 |
| JP | 2009-504210 | 2/2009 |
| KR | 20-0367882 | 11/2004 |
| KR | 20-0400568 | 8/2005 |
| KR | 10-0598627 | 7/2006 |
| KR | 10-0953398 | 4/2010 |
| KR | 10-1025134 B1 | 3/2011 |
| KR | 10-1028468 | 4/2011 |
| KR | 10-1053551 | 7/2011 |
| WO | 94/27456 | 12/1994 |
| WO | 95/11602 | 5/1995 |
| WO | 1995/03720 | 9/1995 |
| WO | 98/33408 | 8/1998 |
| WO | 98/37782 | 9/1998 |
| WO | 99/09850 | 3/1999 |
| WO | 99/15043 | 4/1999 |
| WO | 99/43231 | 9/1999 |
| WO | 00/53045 | 9/2000 |
| WO | 2000/76337 A1 | 12/2000 |
| WO | 01/08525 | 2/2001 |
| WO | 01/15559 | 3/2001 |
| WO | 02/051511 | 7/2002 |
| WO | 2004/093569 | 11/2004 |
| WO | 2005/013748 A1 | 2/2005 |
| WO | 2007/016983 | 2/2007 |
| WO | 2008/015214 | 2/2008 |
| WO | 2008/033963 | 3/2008 |
| WO | 2009/134858 | 11/2009 |
| WO | 2010/059989 A2 | 5/2010 |
| WO | 2012/165803 A2 | 12/2012 |
| WO | 2015/035885 | 3/2015 |
| WO | 2015/179332 A1 | 11/2015 |
| WO | 2015/181928 A1 | 12/2015 |

OTHER PUBLICATIONS

Anonymous, "Shore durometer," Wikipedia, the free encyclopedia, Mar. 10, 2012, XP002747470, Retrieved from the Internet: URL: https:--en.wikipedia.org-w-indexphp?title=Shore_durometer&oldid=481128180 [retrieved on Oct. 20, 2015] *shore A, shore D, durometer, polymer, rubber, gel; the whole document*, 6 pages.
ASOLO® Boot Brochure Catalog upon information and belief date is as early as Aug. 22, 1997.
Supplementary European Search Report for EP 13761841 dated Oct. 21, 2015, 8 pages.
La Sportiva, A Technical Lightweight Double Boot for Cold Environments http:--www.sportiva.com-products-footwear-mountain-spantik.
"Strength of materials used to make my Safety Harnesses," Elaine, Inc. Jul. 9, 2012. Retrieved from <https:--web.archive.org-web-20120709002720-http:--www.childharness.ca-strength_data.html> on Mar. 17, 2014, 2 pages.
"Save Tourniquet," 3 pages. Copyright 2015. Accessed on Dec. 11, 2015. Retrieved from http:--www.savetourniguet.com/.
International Search Report and Written Opinion for PCT-US2013-032326 dated Jun. 14, 2013, 27 pages.
International Preliminary Report on Patentability for PCT-US2013-032326 dated Sep. 16, 2014, 6 pages.
International Search Report and Written Opinion for PCT-US2013-057637 dated Apr. 7, 2014, 34 pages.
International Preliminary Report on Patentability for PCT-US2013-057637 dated Mar. 3, 2015, 9 pages.
International Search Report and Written Opinion for PCT-US2013-068342 dated Apr. 7, 2014, 29 pages.
International Preliminary Report on Patentability for PCT-US2013-068342 dated May 5, 2015, 9 pages.

(56) References Cited

OTHER PUBLICATIONS

International Search Report and Written Opinion for PCT-US2014-014952 dated Apr. 25, 2014, 17 pages.
International Preliminary Report on Patentability for PCT-US2014-014952 dated Aug. 11, 2015, 9 pages.
International Search Report and Written Opinion for PCT-US2014-066212 dated Apr. 22, 2015, 16 pages.
International Search Report and Written Opinion for PCT-US2014-032574 dated Oct. 31, 2014, 19 pages.
International Search Report and Written Opinion for PCT-US2014-045291 dated Nov. 6, 2014, 12 pages.
International Search Report and Written Opinion for PCT-US2014-013458 dated May 19, 2014, 12 pages.
International Preliminary Report on Patentability for PCT-US2014-013458 dated Jul. 28, 2015, 7 pages.
International Search Report and Written Opinion for PCT-US2013-068814 dated Jun. 9, 2014, 18 pages.
International Preliminary Report on Patentability for PCT-US2013-068814 dated May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570, 1 page.
International Search Report and Written Opinion for PCT-US2014-055710 dated Jul. 6, 2015, 19 pages.
International Search Report and Written Opinion for PCT-US2014-054420 dated Jul. 6, 2015, 21 pages.
The Preliminary Rejections from the Korean Intellectual Property Office for Application No. 30-2014-34959 received Aug. 7, 2015, is not translated into English. The document requests a renaming of the application to be in accordance with Korean patent law, 6 pages total.
The Preliminary Rejections from the Korean Intellectual Property Office for Application No. 30-2014-34959 received Apr. 7, 2015, is not translated into English. The document requests a revision of the drawings to be in accordance with Korean patent law, 6 pages total.
Certificate of Design Registration No. 30-809409 on Aug. 3, 2015 from the Korean Intellectual Property Office for Application No. 30-2015-11475, 2 pages.
Certificate of Design Registration No. 30-809410 on Aug. 3, 2015 from the Korean Intellectual Property Office for Application No. 30-2015-11476, 2 pages.
European Search Report for EP 14168875 dated Oct. 29, 2014, 9 pages.
International Search Report and Written Opinion for PCT/US2014/020894 dated Jun. 20, 2014, 12 pages.
International Preliminary Report on Patentability for PCT/US2014/020894 dated Sep. 8, 2015, 7 pages.
International Search Report and Written Opinion for PCT/US2014/041144 dated Dec. 10, 2014, 13 pages.
International Preliminary Report on Patentability for PCT/US2014/032574 dated Oct. 6, 2015, 11 pages.
International Search Report and Written Opinion for PCT/US2014/046238 dated Nov. 21, 2014, 17 pages.
Office Action received Oct. 8, 2015 from the German Patent and Trademark Office for Application No. 402015100191.2, regarding the title of the invention, 2 pages.
U.S. Appl. No. 13/829,601, filed Mar. 14, 2013, Non-Final Rejection dated Nov. 9, 2015, all pages.
U.S. Appl. No. 13/829,601, filed Mar. 14, 2013, Notice of Allowance dated Mar. 1, 2016, all pages.
U.S. Appl. No. 13/973,917, filed Aug. 22, 2013, Non-Final Rejection dated Jun. 30, 2015, all pages.
U.S. Appl. No. 13/973,917, filed Aug. 22, 2013, Final Rejection dated Jan. 4, 2016, all pages.
U.S. Appl. No. 13/973,917, filed Aug. 22, 2013, Notice of Allowance dated Jun. 6, 2016, all pages.

\* cited by examiner

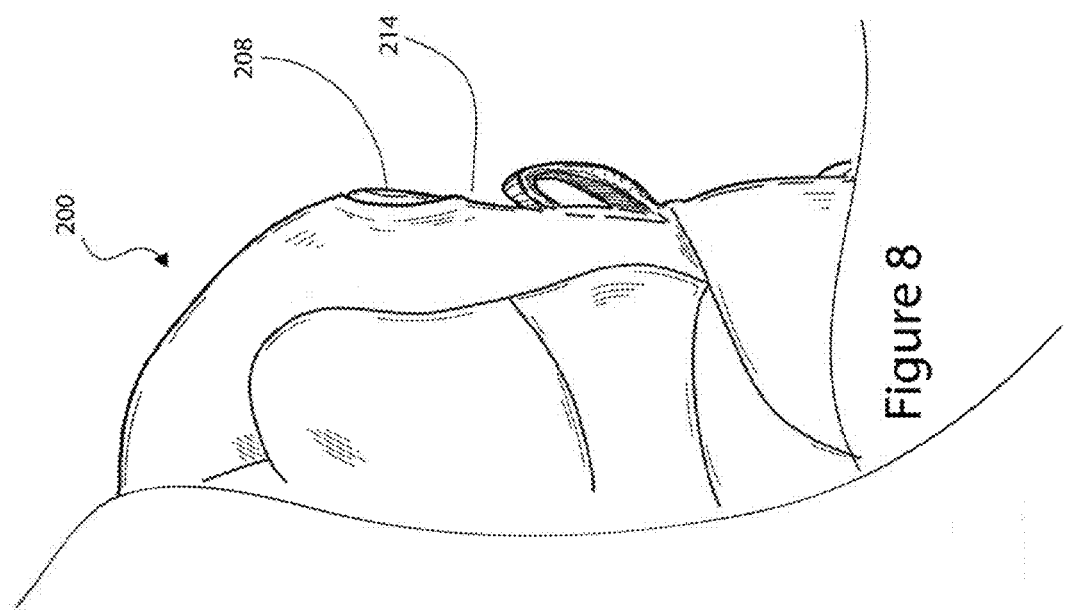
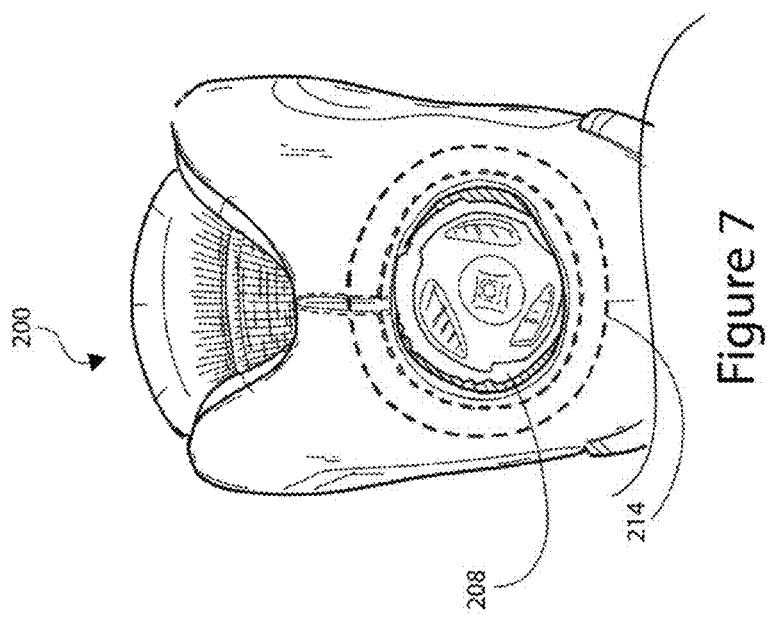

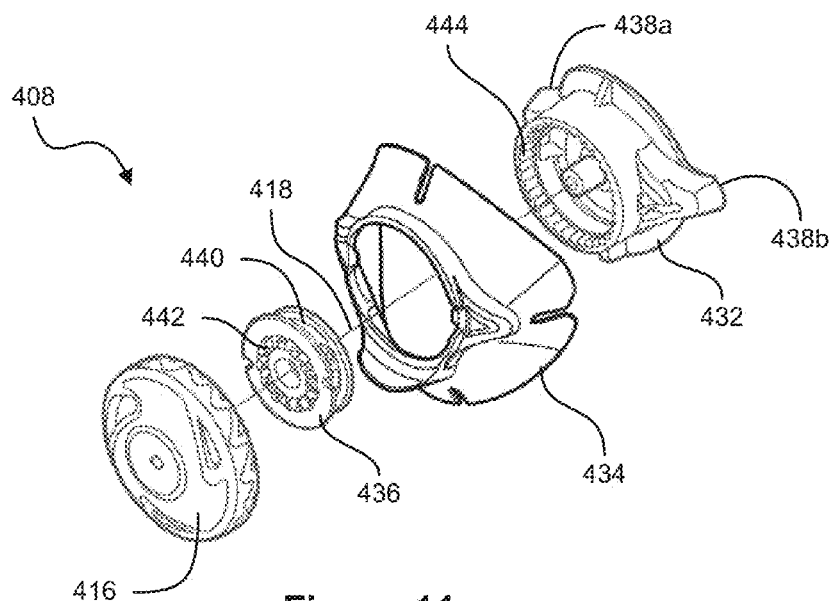
Figure 11
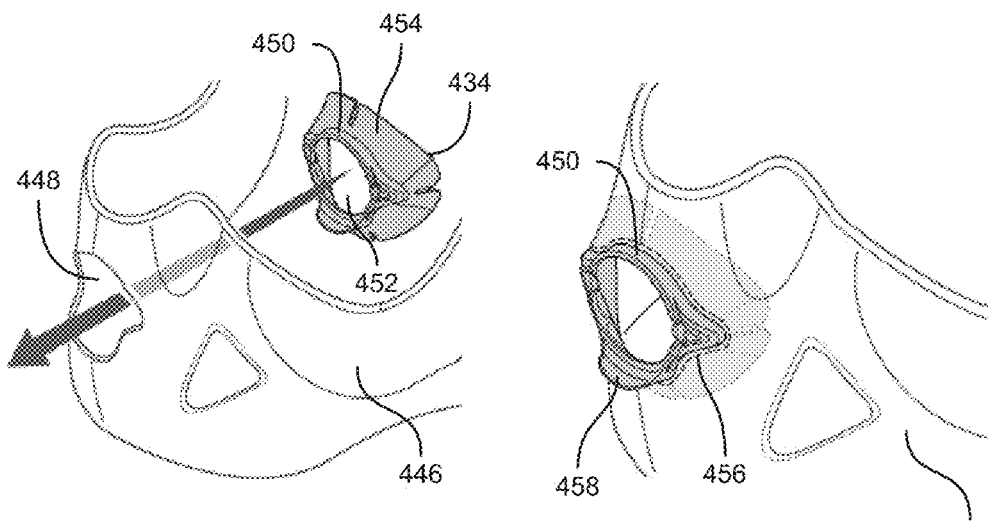
Figure 12
Figure 13

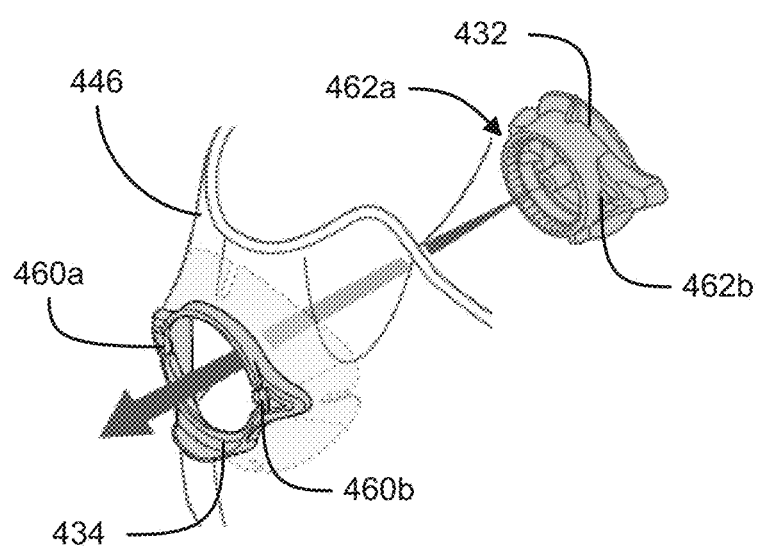
Figure 14
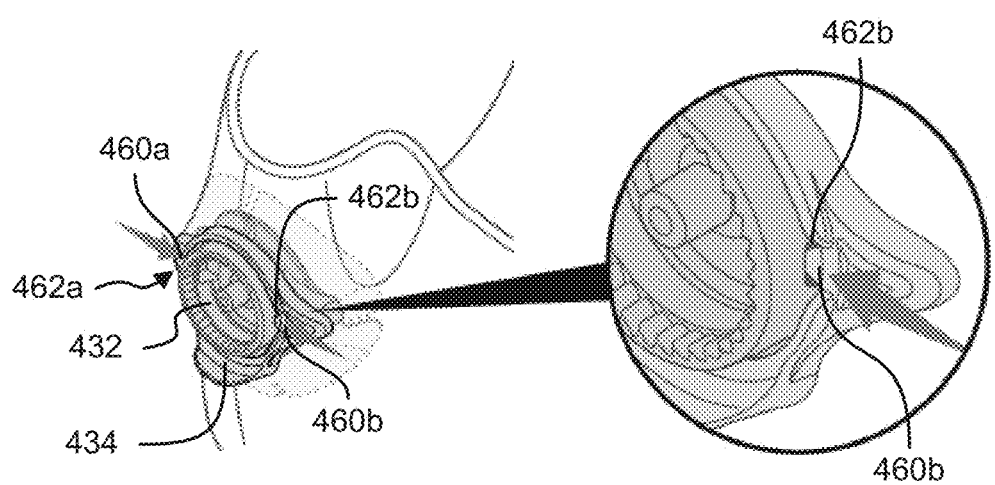
Figure 15                    Figure 16

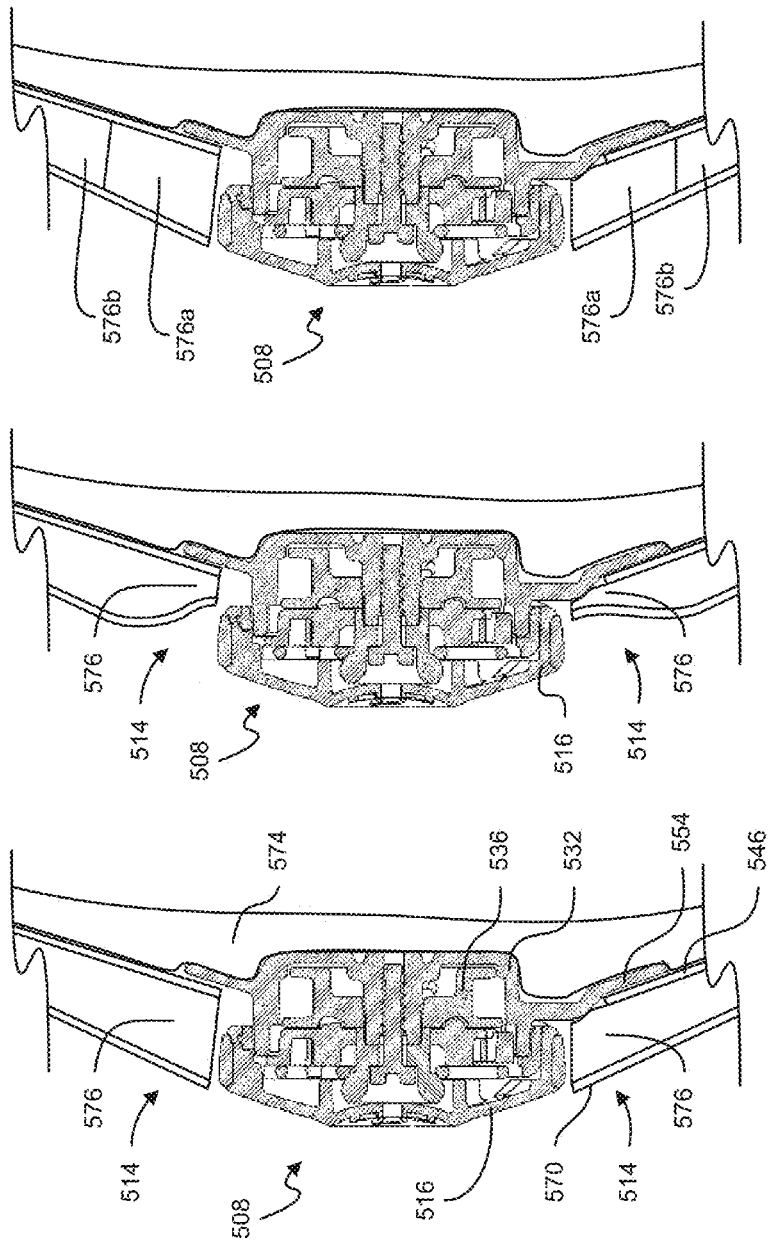

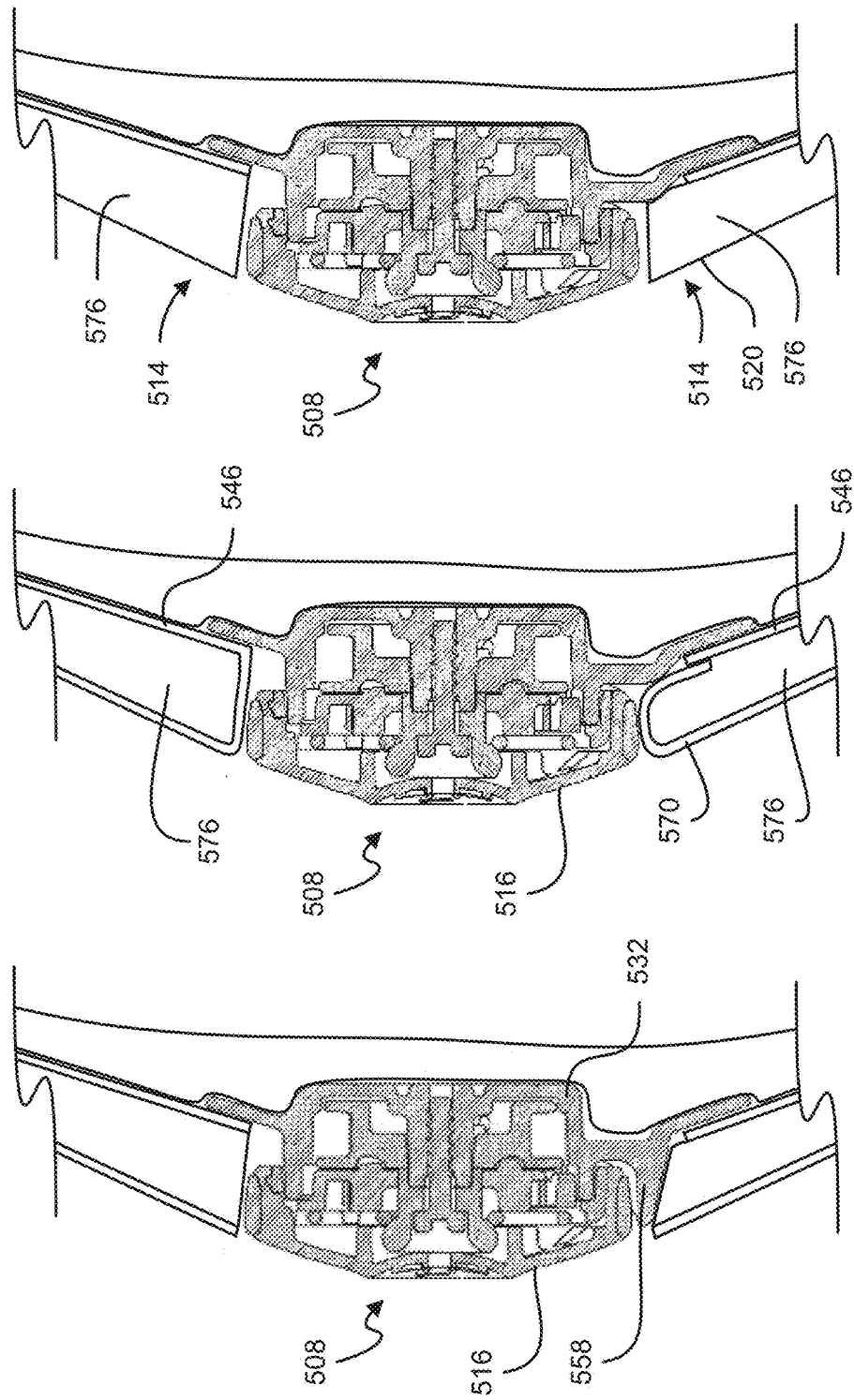

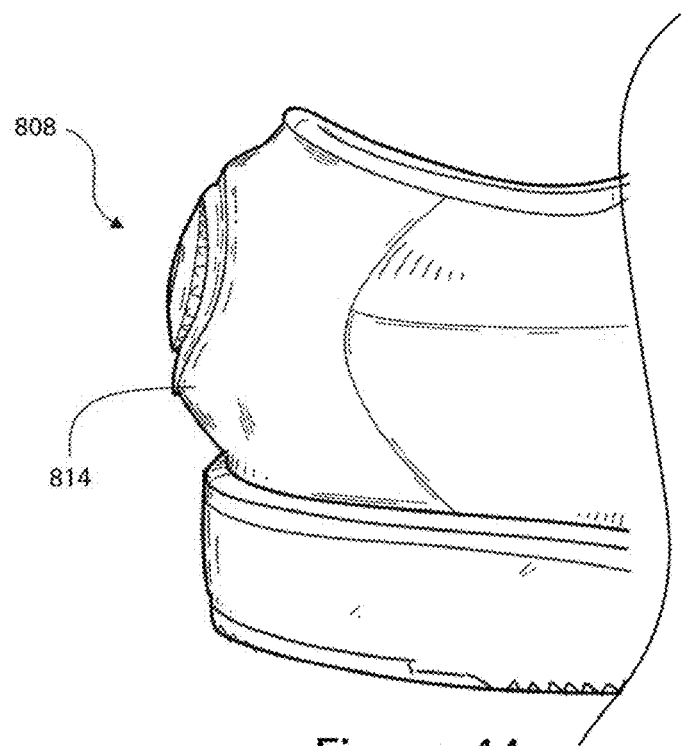
Figure 44
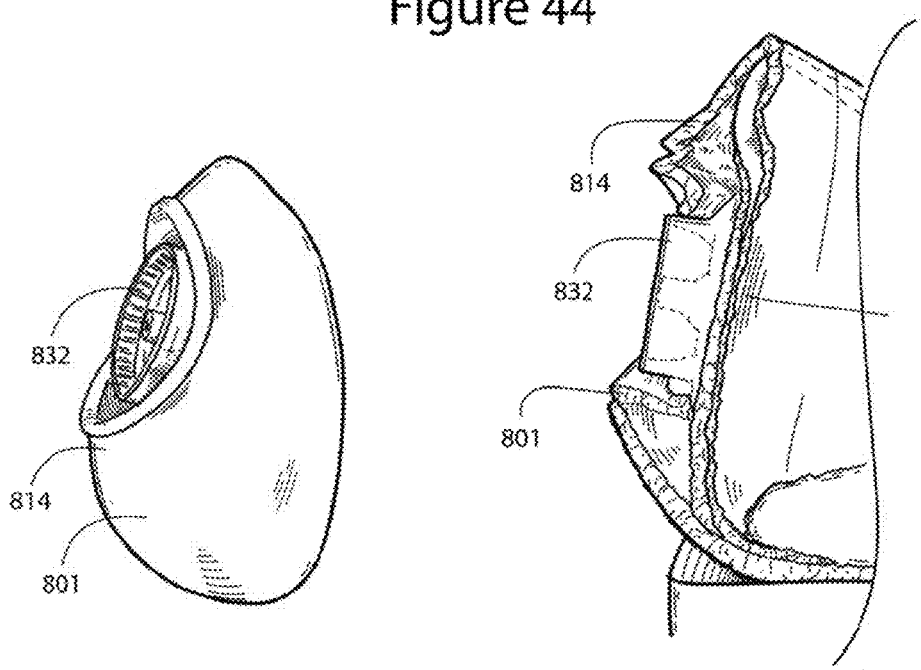
Figure 45
Figure 46

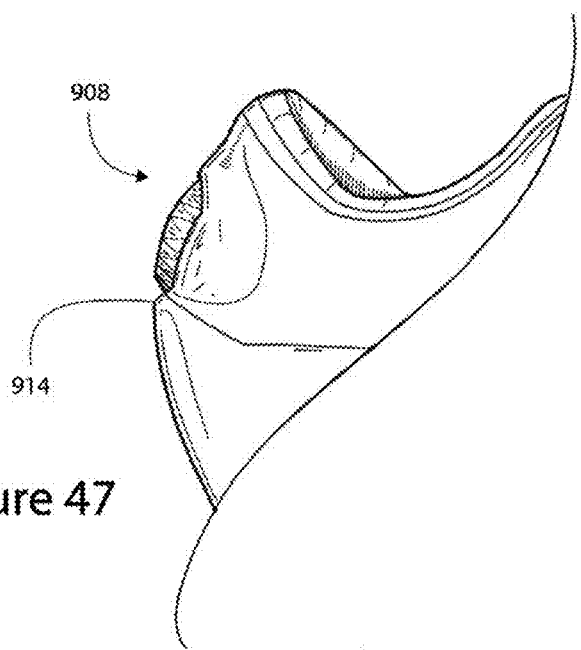
Figure 47
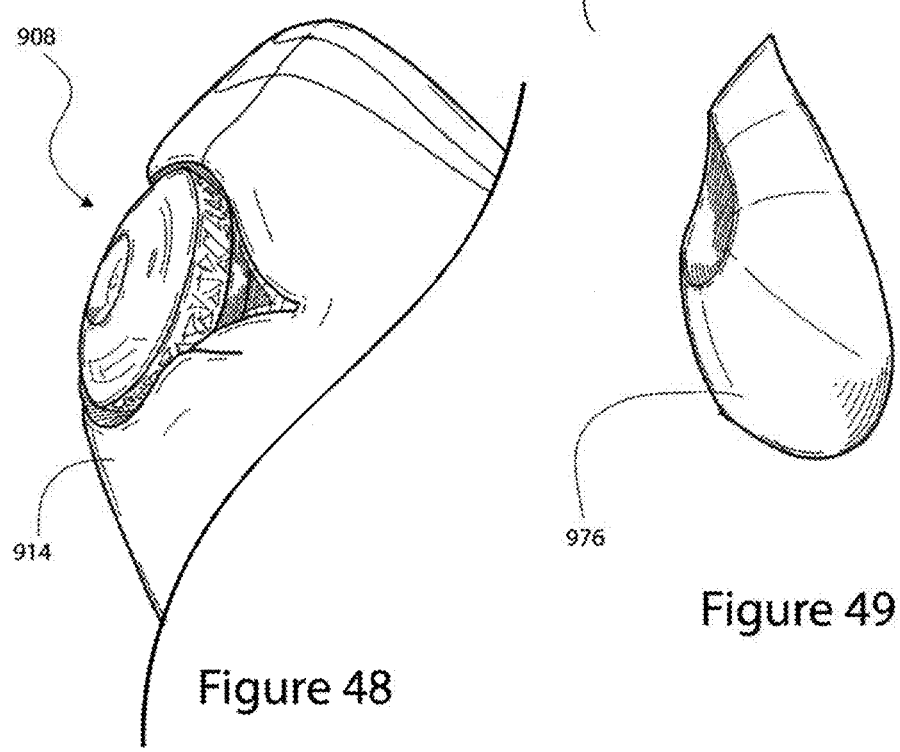
Figure 48
Figure 49

TIGHTENING MECHANISMS AND APPLICATIONS INCLUDING THE SAME

CROSS-REFERENCES TO RELATED APPLICATIONS

This application is a continuation-in-part of U.S. patent application Ser. No. 15/191,281, filed Jun. 23, 2016, entitled "Tightening Mechanisms and Applications Including the Same", which is a continuation of U.S. patent application Ser. No. 13/829,601, filed Mar. 14, 2013, entitled "Tightening Mechanisms and Applications Including the Same," which claims priority to Provisional U.S. Patent Application No. 61/611,418, filed Mar. 15, 2012, entitled "Tightening Mechanisms and Applications Including the Same." This application is also a continuation-in-part of U.S. patent application Ser. No. 13/973,917, filed Aug. 22, 2013, entitled "Reel Based Lacing System", which is a continuation of U.S. patent application Ser. No. 13/098,276, filed Apr. 29, 2011, entitled "Reel Based Lacing System", which claims priority to Provisional U.S. Patent Application No. 61/330,129, filed Apr. 30, 2010, entitled "Reel Based Lacing System." The entire disclosures of all aforementioned applications are hereby incorporated by reference, for all purposes, as if fully set forth herein.

BACKGROUND OF THE INVENTION

Field of the Disclosure

Some embodiments of the present disclosure relate to articles (e.g., shoes, boots, braces, and other wearable articles) that use tightening systems (e.g., lacing systems).

Description of the Related Art

Although various lacing systems are available for use in connection with various wearable articles, existing lacing systems suffer from various drawbacks. For example, some lacing systems include an exposed lace tightening mechanism, which can be visually unappealing. Also, during contact sports and some other uses, the exposed lace tightening mechanism can be damaged or unintentionally actuated (e.g., loosened). Accordingly, there persists a need for lacing systems that include a concealed or protected lace tightening mechanism.

BRIEF SUMMARY OF THE INVENTION

Various embodiments disclosed herein relate to an article that includes a base material and a tightening mechanism coupled to the base material. The tightening mechanism can include a rotatable knob, and rotation of the knob in a tightening direction can tighten the article. The article can include a concealing portion that can extend upward from the base material and can at least partially radially surround the tightening mechanism. At least a portion of the rotatable knob can be rearward or inward of an outer surface of the concealing portion. In some embodiments, a majority of the rotatable knob can be rearward or inward of the outer surface of the concealing portion. In some embodiments, substantially the entire rotatable knob can be rearward or inward of the outer surface of the concealing portion. In some embodiments, a top surface of the rotatable knob can be substantially flush with the outer surface of the concealing portion.

The concealing portion can include a compressible area, and compression of the compressible area can displace the outer surface of the concealing portion from a first position to a second position, and the second position can have a lower height than the first position. The compressible area can include compressible foam. The concealing portion can include a second foam material that is less compressible than the compressible foam, and the second foam material can at least partially radially surround the compressible foam. The compressible foam can be resilient and can facilitate return of the outer surface from the second position to the first position when a compressing force is not applied. The compressible area can include one or more collapsible recesses.

The base material can include a hole, and at least a portion of the tightening mechanism can extend through the hole in the base material.

In some embodiments, the concealing portion can radially surround the tightening mechanism by a full 360 degrees.

The concealing portion can include first and second areas on substantially opposite sides of the tightening mechanism from each other, and third and fourth areas on substantially opposite sides from each other. The heights of the first and second areas of the concealing portion can be greater than the heights of the third and fourth areas of the concealing portion such that the rotatable knob can be more exposed at the third and fourth areas than at the first and second areas.

In one embodiment, an article (e.g., shoe, boot, apparel, and the like) may include a base material (e.g., heel, tongue, outsole, and the like) and a tightening mechanism coupled to the base material. The tightening mechanism may include a rotatable knob, wherein rotation of the knob in a tightening direction tightens the article. A compressible material may be coupled with a body (e.g., a housing) of the tightening mechanism. The compressible material may be positioned under a top layer of the base material so as to provide a transition between the body of the tightening mechanism and the base material to conceal edges of the body from view of a user. A concealing portion may extend upward from the base material and at least partially radially surround the tightening mechanism. At least a portion of the rotatable knob may be positioned rearward of an outer surface of the concealing portion so as to conceal the portion of the knob or the entire knob.

In one embodiment, the compressible material may include a foam material having a durometer of between about 10 and about 25 Shore A. In some embodiments, a relatively rigid mounting component (e.g., a bayonet) may be coupled with the compressible material and the base material. The body of the tightening mechanism may be coupled with the mounting component to limit distortion of the compressible material as the knob is rotated in a tightening direction to tighten the article. In some embodiments, the body of the tightening mechanism may be integrally formed with one or more components of the base material. In a specific embodiment, the base material may comprise a shoe or a portion or component thereof, and the tightening mechanism and compressible material may be coupled with a heel portion of the shoe.

BRIEF DESCRIPTION OF THE DRAWINGS

Various embodiments are depicted in the accompanying drawings for illustrative purposes, and should in no way be interpreted as limiting the scope of the inventions.

FIG. 7 is a back view of an example embodiment of a boot having a tightening mechanism incorporated into the heel portion thereof.

FIG. 8 is a side view of the boot of FIG. 7.

FIG. 11 is an exploded isometric view of a tightening mechanism.

FIG. 12 shows a securing member and being coupled to an upper material of a shoe.

FIG. 13 shows the securing member stitched to the upper material.

FIG. 14 shows a housing being coupled to the securing member.

FIG. 15 shows the housing and the securing member in an engaged configuration.

FIG. 16 is a detailed view of the engagement members of the securing member and the housing.

FIG. 24 shows a schematic cross-sectional view of an example embodiment of a tightening mechanism at least partially surrounded by a concealing portion in an uncompressed state.

FIG. 25 shows a schematic cross-sectional view of a tightening mechanism with a concealing portion in a compressed state.

FIG. 26 shows a schematic cross-sectional view of a tightening mechanism with a concealing portion having areas with different levels of compressibility.

FIG. 30 shows a schematic cross-sectional view of a tightening mechanism with a shielding element.

FIG. 31 shows a schematic cross-sectional view of a tightening mechanism with a concealing portion that encloses a compressible material.

FIG. 32A shows a schematic cross-sectional view of a tightening mechanism with a concealing portion that includes an exposed compressible material.

FIG. 44 is a side view of a shoe having a tightening mechanism and a concealing portion at least partially surrounding the tightening mechanism.

FIG. 45 shows a shaping member with a housing of the tightening mechanism mounted thereto.

FIG. 46 is a cross-sectional view of the shoe of FIG. 44 showing the concealing portion and the housing coupled to the shoe.

FIG. 47 is a side view of a shoe having a tightening mechanism and a concealing portion at least partially surrounding the tightening mechanism.

FIG. 48 shows another view of the shoe of FIG. 47.

FIG. 49 shows a spacer that can be configured to provide the shape of the concealing portion of FIG. 47.

DETAILED DESCRIPTION OF THE INVENTION

Figure 1:
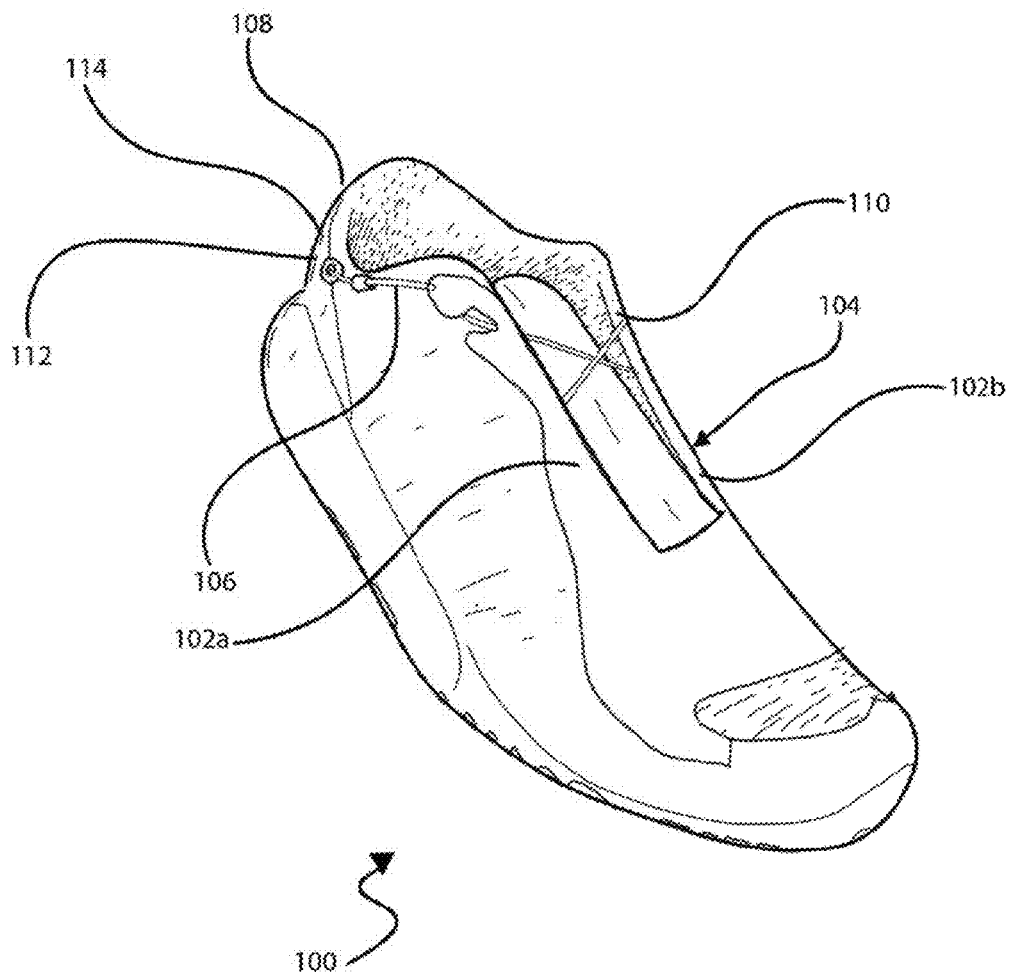
FIG. 1 is an isometric view of an example embodiment of a shoe that includes a reel-based tightening system

FIG. 1 is an isometric view of an example embodiment of a shoe 100 that includes a reel-based tightening system. Although many embodiments are discussed herein as relating to shoes or other footwear, the embodiments disclosed herein can also related to other types of wearable articles, and to other objects that can be tightened and/or loosened (e.g., boots, hats, belts, sandals, gloves, braces, backpacks, snowboard bindings). The shoe 100 of FIG. 1 can include a first portion 102a and a second portion 102b that can be drawn towards each other to tighten the shoe 100 and can be moved away from each other to loosen the shoe 100. The first and second portions 102a and 102b can be spaced apart forming a gap 104 therebetween, or, in some embodiments, the first and second portions 102a and 102b can touch or overlap. A tension member, such as a lace 106, can extend between the first and second portions 102a and 102b so that increased tension on the lace 106 can cause the first and second portions 102a and 102b to be drawn together, and so that reducing tension on the lace 106 can cause the first and second portions 102a and 102b to move apart from each other. The lace 106 can be coupled to a tightening mechanism 108 that is configured to adjust the tension on the lace 106 for tightening and/or loosening the shoe 100. The shoe 100 can include one or more lace guides 110 configured to direct the lace 106 along a lace path between the first and second portions 102a and 102b of the shoe 100. Although many embodiments are disclosed as using a lace 106, other tensioning members (e.g., a strap) can be used for the various embodiments disclosed herein.

The tightening mechanism 108 can be mounted onto the heel portion of the shoe 100, as shown in FIG. 1, or to various other portions of the shoe 100, such as, for example, to the tongue or to a side portion of the shoe 100. The shoe can also include one or more lace channels 112 configured to direct the lace 106 to the tightening mechanism 108, and the lace channels 112 can be positioned at least partially under an outer layer of the shoe 100 so that the lace channels 112 are at least partially hidden from view.

Figure 2:
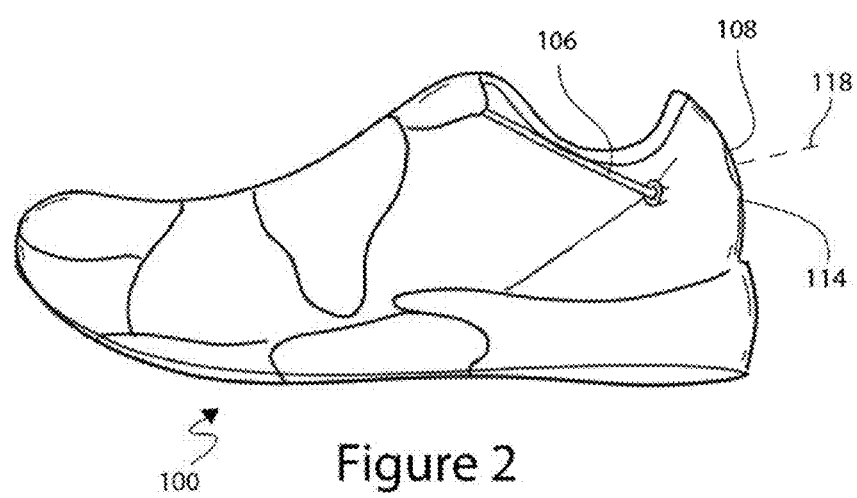
FIG. 2 is a side view of the shoe of FIG. 1 with the concealing portion of the shoe in a first or uncompressed position.
Figure 3A:
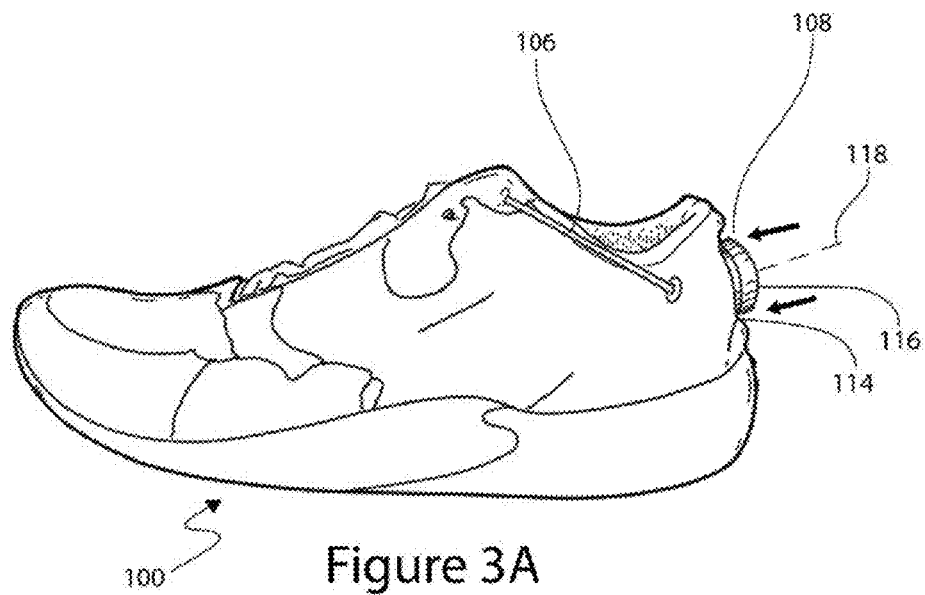
FIG. 3A is a side view of the shoe of FIG. 1 with the concealing portion of the shoe in a second or compressed position.
Figure 3B:
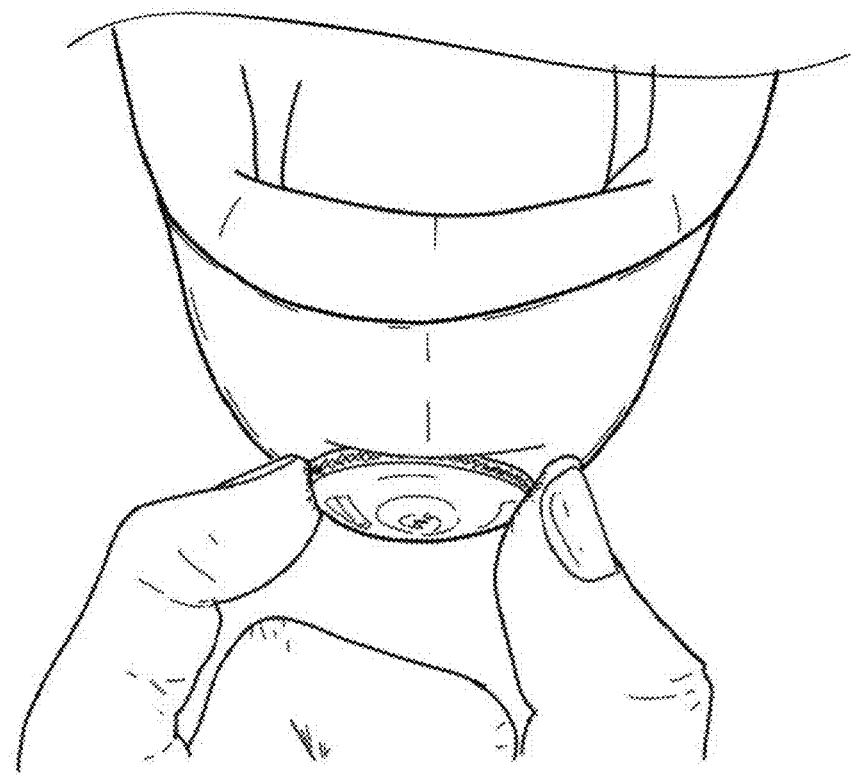
FIG. 3B shows another example implementation of a shoe with a concealing portion having compressible portions on the sides of a tightening mechanism.
Figure 3C:
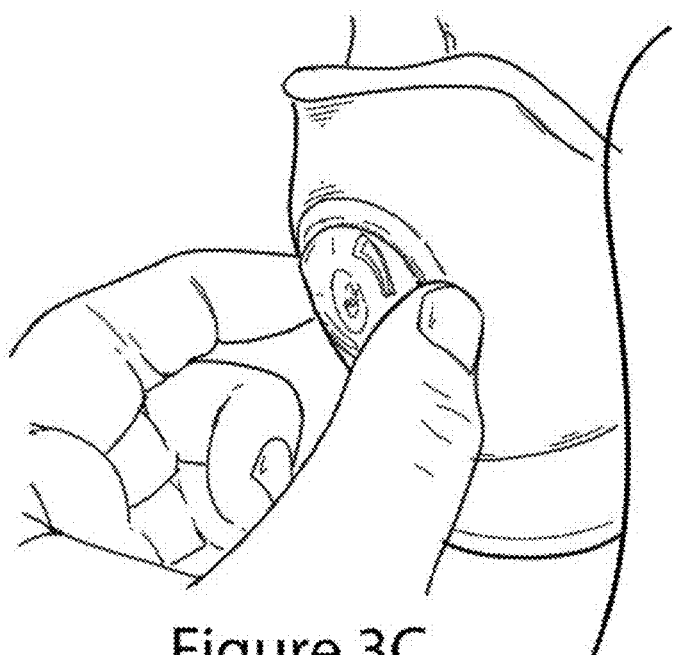
FIG. 3C is another view of the shoe of FIG. 3B.

The tightening mechanism 108 can be at least partially concealed or protected by a concealing portion 114 of the shoe 100 that at least partially surrounds the tightening mechanism 108. In come embodiments, the concealing portion 114 can include a compressible area that allows the concealing portion 114 to be transitioned between a first, uncompressed position, as shown in FIG. 2, to a second, compressed position, as shown in FIG. 3A. The concealing portion 114 can be compressible around substantially the full circumference of the tightening mechanism 108, or at only certain portions around the tightening mechanism. 108. For example, in some embodiments, the concealing portion 114 can be compressible on right and left sides (e.g., at 3- and 9-o'clock) of the tightening mechanism 108 and can be substantially incompressible at the areas below and/or above (e.g., at 6- and 12-o'clock) the tightening mechanism 108 (e.g., as shown in FIGS. 3B and 3C). In other embodiments, the concealing portion 114 can be compressible at the areas below and/or above (e.g., at 6- and 12-o'clock) the tightening mechanism 108 and can be substantially incompressible on right and left sides (e.g., at 3- and 9-o'clock) of the tightening mechanism 108. In the uncompressed position shown in FIG. 2, the concealing portion 114 of the shoe 100 can surround at least a portion of the tightening mechanism 108 to at least partially hide the tightening mechanism 108 from view, which can improve the visual appearance of the shoe 100. For example, for certain types of wearable articles (e.g., some golf shoes, running shoes, and casual shoes), the presence of an exposed tightening mechanism 108 can appear bulky or otherwise be inconsistent with the style of the article. Also, in some embodiments, the undesirable look of an exposed tightening mechanism 108 is further compounded on smaller sized shoes. By at least partially concealing the tightening mechanism 108, the concealing portion 114 of the shoe 100 can increase the aesthetic appeal of the shoe 100.

Protecting or partially concealing the tightening mechanism 108 with a substantially resilient concealing portion 114 can allow aesthetically pleasing incorporation of the tightening mechanism 108 with the article. For example, as shoe sizes change, there can be a substantial dimensional reduction in the mounting area in the heel portion of the shoe (e.g., the shoe sizes get smaller). A substantially resilient concealing portion 114 can be formed around various surfaces to produce a visually appealing final structure that may not be possible with an entirely rigid shielding mechanism. As discussed elsewhere herein, the concealing portion 114 can incorporate some rigid components while still permitting adaptation to different sized areas.

In some embodiments, the concealing portion 114 can protect the tightening mechanism 108 from damage and/or unintentional actuation. For example, an exposed tightening mechanism 108 can be unintentionally actuated when, for example, the tightening mechanism 108 is struck during contact sports. In some embodiments, unintentional actuation of the tightening mechanism 108 can unintentionally loosen the lace 106 or can over-tighten the lace 106, which can cause discomfort and can degrade the performance of an athlete. By at least partially concealing the tightening mechanism 108, the concealing portion 114 of the shoe 100 can protect the tightening mechanism 108 from being unintentionally actuated or damaged.

When a compressing force (shown schematically by arrows in FIG. 3A) is applied to the concealing portion 114, the collapsible area can collapse thereby transitioning the concealed portion 114 to the second or collapsed position, thereby increasing the amount of the tightening mechanism 108 that is exposed. The tightening mechanism 108 can include a rotatable knob 116 that is configured to be rotatable about an axis 118. Rotation of the knob 116 in a tightening direction (e.g., clockwise) can tighten the shoe 100, for example, by gathering lace 106 around a rotatable spool (not shown). In some embodiments, rotation of the knob 116 in a loosening direction (e.g., counterclockwise) can loosen the shoe 100, for example, by releasing lace 106 from the spool. In some embodiments, the knob can be rotated between 60° and 180° degrees in the loosening direction to release the lace 106 from the spool. In some embodiments, the knob 116 can be configured to be pulled axially outwardly along the direction of the axis 118 to release tension on the lace 106. In some embodiments, actuation of the knob 116 (e.g., rotation in the loosening direction or pulling in axial direction) can allow the spool to rotate freely independent of the knob 116, which can allow for rapid loosening of the shoe 100. In some of these rapid loosening embodiments, it can be especially advantageous to protect the knob 116 to prevent accidental actuation, which can cause accidental rapid loosening.

In the compressed position, the concealing portion 114 of the shoe 100 can expose a sufficient portion of the knob 116 to allow a user to actuate the knob 116, such as by rotating the knob 116 in a tightening direction, or in a loosening direction, or by pulling the knob 116 axially outwardly. The compressible area can be configured to compress (e.g., axially in the direction of the axis 118) under pressure applied by the fingers of the user, and in some embodiments, the compressible area can have sufficient resistance to protect against unintentional actuation of the knob 116. The compressible area can be resilient such that the concealing portion 114 returns to the first or uncompressed position when the compressing force is removed.

Figure 4:
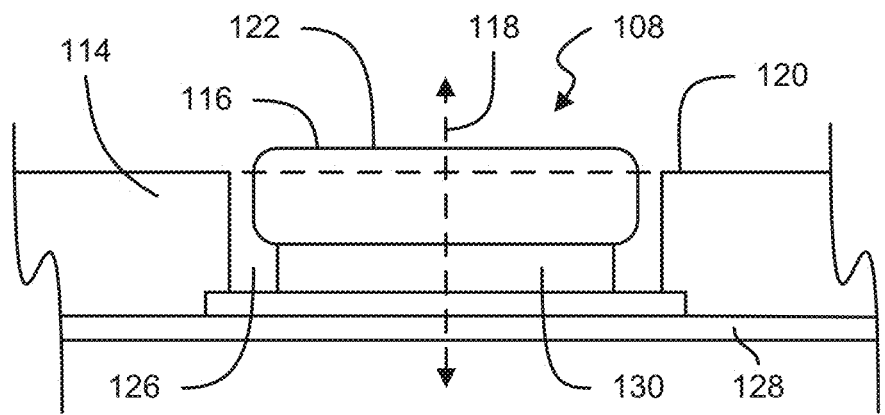
FIG. 4 is a schematic cross-sectional view of an example embodiment of a tightening mechanism incorporated into an article and at least partially surrounded by a concealing portion.
Figure 5:
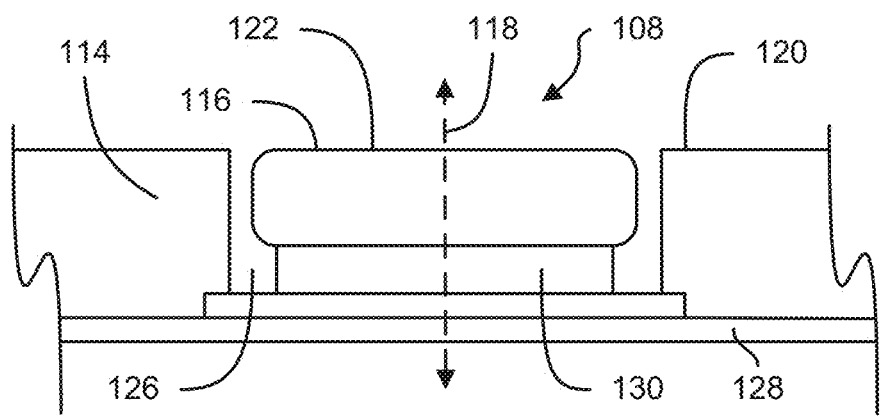
FIG. 5 is a schematic cross-sectional view of another example embodiment of a tightening mechanism incorporated into an article and at least partially surrounded by a concealing portion.
Figure 6A:
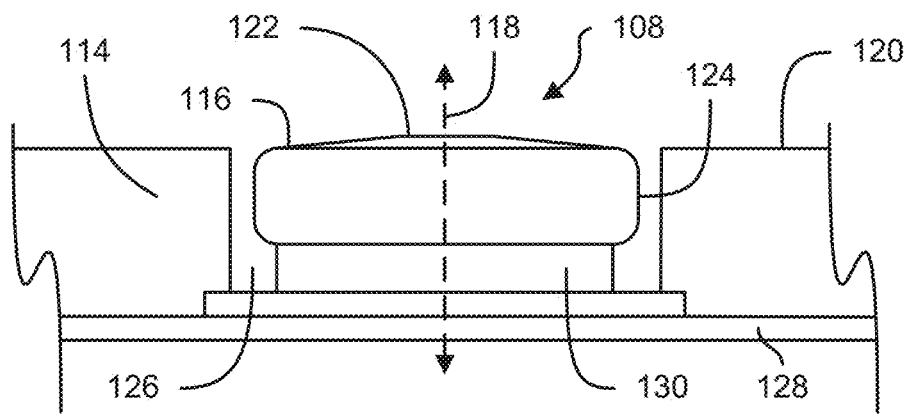
FIG. 6A is a schematic cross-sectional view of another example embodiment of a tightening mechanism incorporated into an article and at least partially surrounded by a concealing portion.

The concealing portion 114 of the article (e.g., the shoe 100) can radially surround at least a portion of the knob 116. As shown schematically in FIG. 4, when the concealing portion 114 is in the uncompressed position, at least a portion of the knob 116 can be disposed axially rearward of an outer surface 120 of the concealing portion 114 in the direction of the axis 118. As used herein the term "rearward" is used broadly to mean that one object, or portion thereof, is displaced back from another object, or portion thereof, even if the first object, or portion thereof, is not positioned directly behind the other object, or portion thereof. Also, in many instances, the terms "rearward," "forward," "inward," "upward," "top," "bottom," and the like can be used to describe locations or directions based on the orientation of the tightening mechanism, regardless of the orientation that the tightening mechanism has to article or the surrounding environment. Thus, at least a portion of the knob 116 can be disposed axially rearward of the outer surface 120 of the concealing portion 114 even when the concealing portion 114 does not cover the top surface 122 of the knob 116. The top surface 122 of the knob 116 can be uncovered, for example, such that the top surface 122 of the knob 116 is visible when viewed from the top down. In some embodiments, a majority of the knob 116 can be disposed rearward of the outer surface 120 of the concealing portion 114. In some embodiments, the entire, or substantially the entire, knob 116 can be disposed rearward of the outer surface 120 of the concealing portion 114. For example, in some embodiments, the top surface 122 of the knob 116 can be substantially flush with the outer surface 120 of the concealing portion 114, as shown in FIG. 5. The concealing portion 114 can extend upward at least as far as the top of the sides 124 of the knob 116, or at least past the lower surface of the knob 116. In some embodiments, the sides 124 of the knob 116 can be partially, entirely, or substantially entirely, rearward of the outer surface 120 of the concealing portion 114. In some cases, a portion of the top 122 of the knob 116 can extend forward of the outer surface 120 of the concealing portion 114 (e.g., due to a generally frusta-conical shape, a curved shape, or other contours, of the top 122 of the knob 116), as shown in FIG. 6A. Various configurations are possible. For example, in some embodiments, at least about 95%, at least about 90%, at least about 85%, at least about 80%, or at least about 75% of the rotatable knob 116 (or of the entire tightening mechanism 108) can be disposed rearward of the outer surface 120 of the concealing portion 114.

The concealing portion 114 can have a recess 126, and the tightening mechanism 108 can be disposed in the recess 126. In some embodiments, the recess 126 can extend only partially through the article. For example, a base layer 128 of the article can be located at the bottom of the recess 126, and the tightening mechanism 108 can be secured to the base layer 128. A housing 130 of the tightening mechanism 108 can be attached to the base layer 128, for example, by stitching, rivets, adhesive, or other suitable manner. The concealing portion 114 can be attached to the base layer 128. In some embodiments, the concealing portion 114 can be one or more additional layers applied to the outside of an otherwise completed article, while in other embodiments, the concealing portion 114 can be formed as an integral portion of the article. In some embodiments, the recess 126 can extend through the article (e.g., through the heel wall, or side wall, of the shoe 100.

Figure 6B:
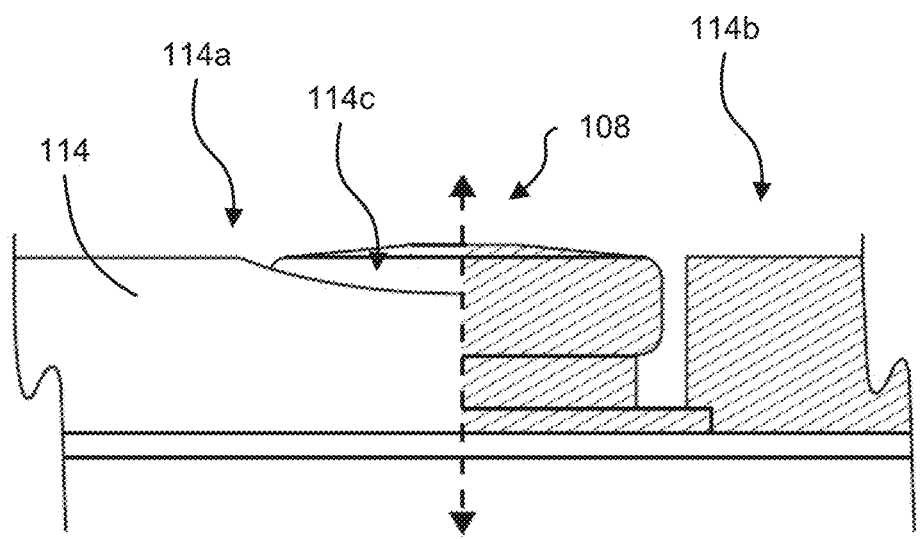
FIG. 6B is a schematic partially cross-sectional view showing an example embodiment of a concealing portion having recesses or cutouts formed to allow a user to operate a tightening mechanism.

FIG. 6B is a schematic partially cross-sectional view showing an example embodiment of a concealing portion 114 having recesses or cutouts formed to allow a user to operate a tightening mechanism 108. The left side of FIG. 6B shows a side view of the tightening mechanism 108 and concealing portion 114. The right side of FIG. 6B shows a cross-sectional view through a center of the tightening mechanism 108, and the cross-sectional portion of FIG. 6B is shown having cross-hatching to emphasize the cross-sectional portion. As can be seen in FIG. 6B, and as discussed elsewhere herein, the concealing portion 114 can have areas 114a and 114b that extend higher than other areas 114c of the concealing portion 114. More of the tightening mechanism 108 can be exposed at the lower areas 114c of the concealing portion 114, for example, to allow a user to grip the sides of the tightening mechanism 108 (e.g., during tightening or loosening of the system). In some embodiments, a recesses, cutout, or scalloped area, etc. can form the lower portions 114c of the concealing portion 114. In some embodiments, the higher areas 114a and 114b of the concealing portion 114 can provide more protection and/or concealment than the lower areas 114c. In some embodiments, the higher areas 114a and 114b can be positioned above and below the tightening mechanism 108 (e.g., at 6- and 12-o'clock), while the lower portions 114c can be positioned on the sides of the tightening mechanism 108 (e.g., at 3- and 9-o'clock). In some embodiments, the concealing portion 114 can be compressible at the lower portions 114c, and can be substantially uncompressible at the higher portions 114a and 114b. In some embodiments, the concealing portion 114 (including the areas 114a, 114b, and 114c) can be substantially uncompressible, and the lower portions 114c can allow the user to actuate the tightening mechanism 108 without displacement of the concealing portion 114. For example a rigid material (e.g., a rigid foam or plastic) can surround at least part of the tightening mechanism 108 to form the shape of the concealing portion 114.

FIG. 7 is a back view of an example embodiment of a boot 200 having a tightening mechanism 208 incorporated into the heel portion thereof. FIG. 8 is a side view of the boot 200. The boot 200 can have features similar to, or the same as, the shoe 100, or the other embodiments described herein. The tightening mechanism 208 can be positioned at or near the collar of the boot 200. The concealing portion 214 can completely surround the tightening mechanism 208 by a full 360 degrees, as shown in FIG. 7, or the concealing portion 214 can surround only a portion of the tightening mechanism 208 (e.g., by at least about 90 degrees, at least about 180 degrees, at least about 270 degrees, at least about 300 degrees, or at least about 330 degrees). In some embodiments, the concealing portion 114 can surround the areas of the tightening mechanism 208 that are most susceptible to being struck during use (e.g., the below the tightening mechanism 208 between the tightening mechanism and the sole of the shoe).

Figure 9:
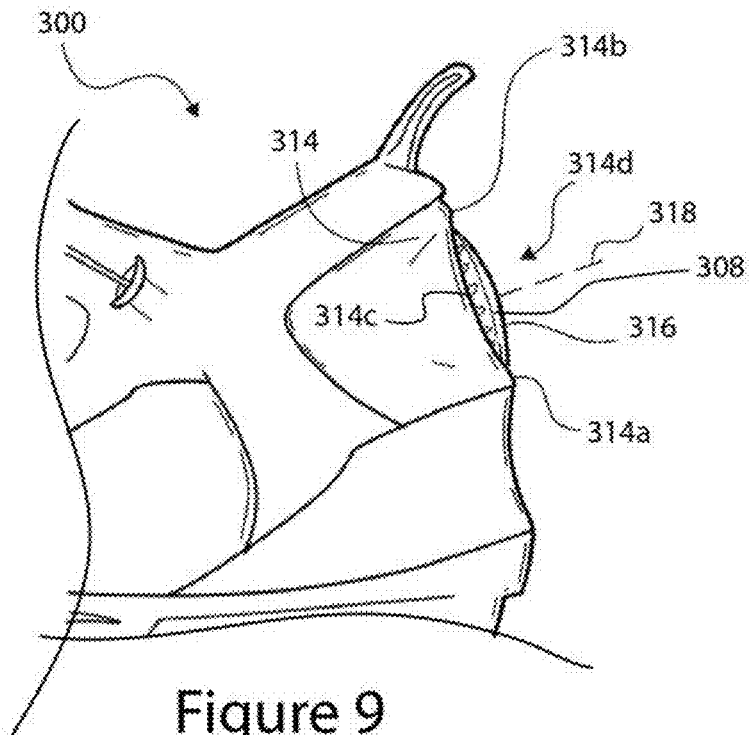
FIG. 9 shows a side view of an example embodiment of a shoe with a concealing portion in an uncompressed position.
Figure 10A:
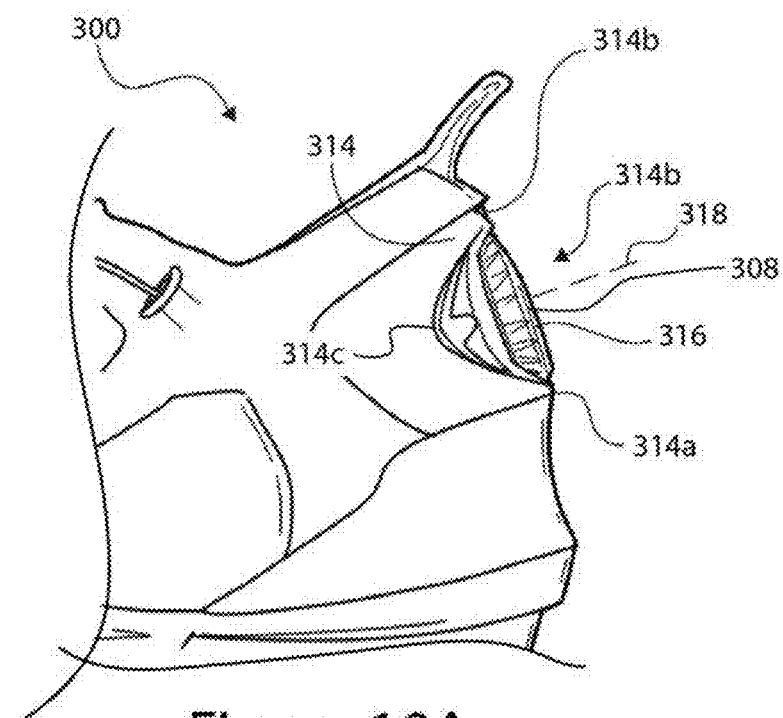
FIG. 10A shows the shoe of FIG. 9 with the concealing portion in a compressed position
Figure 10B:
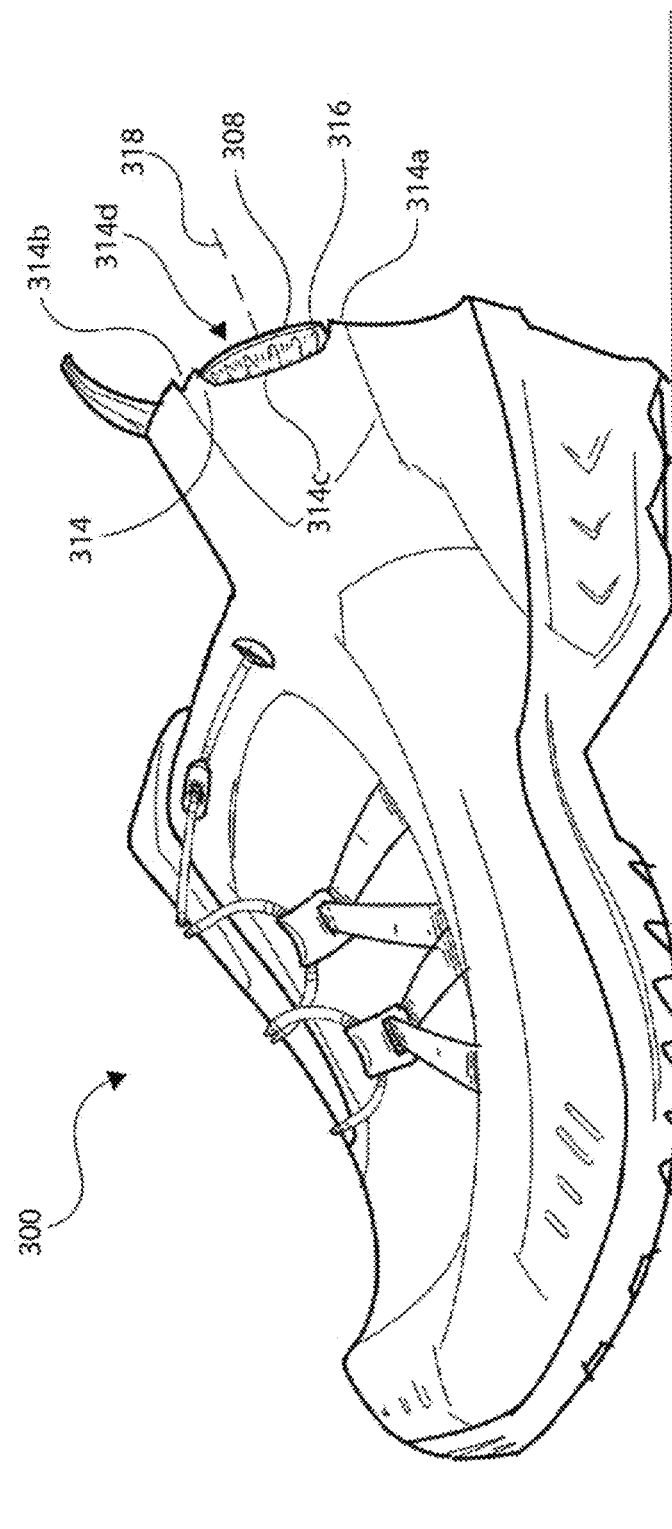
FIG. 10B shows another example implementation of a shoe with a concealing portion.
Figure 17:
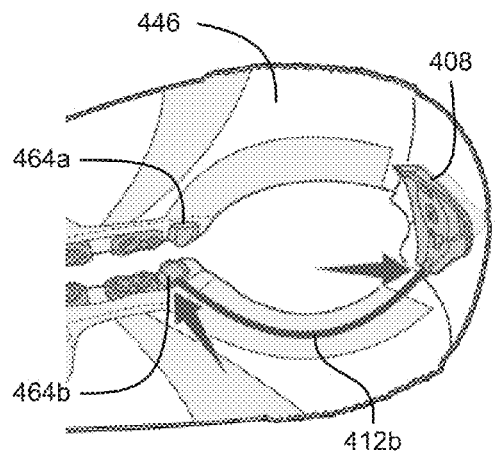
FIGS. 17-20 shows lace channels being applied to the upper material of the shoe.
Figure 18:
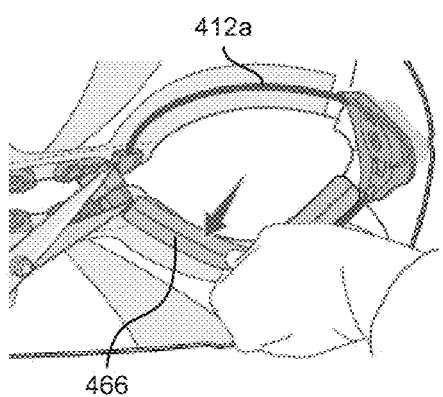
Figure 19:
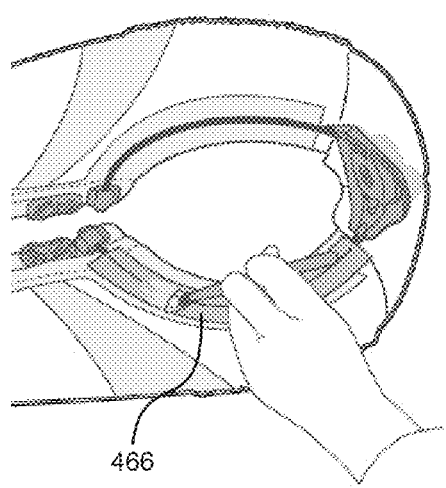
Figure 20:
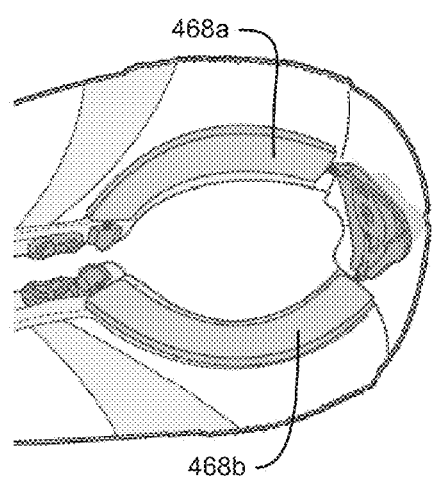

FIGS. 9 and 10 shows side views of an example embodiment of a shoe 300, which can have features similar to the shoe 100, the boot 200, or the other embodiments disclosed herein. FIG. 9 shows a concealing portion 314 in an uncompressed position, and FIG. 10A shows the concealing portion 314 in a compressed position. A tightening mechanism 308 can be mounted onto the heel portion of the shoe 300. As can be seen in FIG. 9, the concealing portion 314 can cover, or substantially cover, the sides of the knob 316 at a first area 314a (e.g., below the tightening mechanism 308 or between the tightening mechanism 308 and the sole of the shoe 300) and/or at a second area 314b (e.g., above the tightening mechanism 308 or between the tightening mechanism 308 and the collar of the shoe 300). The second area 314b can be positioned generally on an opposite side of the tightening mechanism 308 from the first area 314a. Thus, in some embodiments, a cross-sectional view of the shoe 300 taken through the axis 318 and in the plane of the page can be similar to FIGS. 5-6 with respect to the positioning of the knob 316 and the concealing portion 314. Accordingly, the discussion of FIGS. 5-6 can be applied to the shoe 300, in some embodiments.

With further reference to FIG. 9, the concealing portion 314 can cover only a portion of the sides of the knob 316 at a third area 314c (e.g., on a left side of the tightening mechanism 308) and/or at a fourth area 314d (e.g., on a right side of the tightening mechanism 308 (hidden from view in FIG. 9)). The fourth area 314d can be positioned generally on an opposite side of the tightening mechanism 308 from the third area 314c. Thus, in some embodiments, a cross-sectional view of the shoe 300 taken through the axis 318 and transverse to the plane of the page can be similar to FIG. 4 with respect to the position of the knob 316 and the concealing portion 314. Accordingly, the discussion of FIG. 4 can be applied to the shoe 300, in some embodiments. A portion of the knob 316 can be partially exposed, for example, on the right and left sides at the areas 314c and 314d. The partially exposed knob 316 can facilitate gripping of the knob 316 when the user actuates the knob 316.

With reference to FIG. 10A, are least portions of the concealing portion 314 can be compressible to a compressed position to increase the amount of the knob 316 that is exposed, thereby facilitating the gripping of the knob 316 when the user actuates the knob 316. In some embodiments, the areas 314c and/or 314d can be more compressible than the areas 314a and/or 314b. For example, in some embodiments, one or both of the areas 314a and/or 314b can be substantially uncompressible, for example, having a rigid protective member disposed therein to protect the tightening mechanism 308 from being struck near the areas 314a and/or 314b. In some embodiments, the shoe 300 can be configured to have the open-side configuration shown in FIG. 10B when at rest, without the concealing portion 314 being compressed. In some embodiments, the concealing portion 314 (including the areas 314a-d) can be substantially incompressible. The at least partially open sides of the embodiment shown in FIG. 10B can allow a user to manipulate the tightening mechanism 308 without displacing the concealing portion 314.

FIG. 11 is an exploded isometric view of a tightening mechanism 408, which can be used with the shoe 100, the boot 200, the shoe 300, or the other embodiments disclosed herein. The tightening mechanism 408 can include a housing 432, a securing member 434, a spool 436, and a knob 416. The spool 436 can be mounted into the housing 432 such that the spool 436 is rotatable about the axis 418. The housing 432 can have one or more lace holes 438a and 438b configured to receive the lace into the housing 432, so that the lace can be coupled to the spool 436 so that rotation of the spool 436 in a tightening direction gathers the lace into a channel 440 in the spool 432. The spool 436 can include teeth 442 configured to engage teeth (hidden from view) on an underside of the knob 416, so that rotation of the knob 416 can cause rotation of the spool 436, thereby allowing a user to tighten the lace by rotating the knob 416. The housing can include teeth 444 that are configured to engage pawls (hidden from view) on the underside of the knob 416 such that the knob 416 is prevented from rotating in a loosening direction and permitted to rotate in a tightening direction. In some embodiments, the knob 416 can be lifted axially away from the housing 432 to a disengaged position that allows loosening of the lace. Many other configurations can be used for the tightening mechanism 408.

With reference now to FIGS. 12 and 13, the securing member 434 can be secured to the article. For example, an upper material 446 of a shoe can have a hole 448 formed in the heel portion thereof. The securing member 434 can be inserted into the hole 448 from the inside of the upper material 446 back towards the heel portion thereof, as shown in FIG. 12. The securing member 434 can have side walls 450 that surround an opening 452. In some embodiments, the side walls 450 can extend through the hole 448, and in some cases can stretch the upper material 446 to fit around the side walls 450. The securing member 434 can have a securing flange 454, which can remain on the inside of upper material 446 (shown in phantom lines in FIG. 13). The securing flange 454 can be secured upper material 446, such as by stitching 456, or by rivets, or an adhesive, or any other suitable manner. The securing member can include a shield element 458 configured to extend out to cover a side portion of the knob 416, when the tightening mechanism 408 is assembled. The shield element 458 can be positioned on a lower side of the tightening mechanism 408 so that the shield element 458 is positioned between the knob 416 and the sole of the shoe once assembled. Thus, the shield element 458 can provide protection against striking the knob 416 from below (e.g., such as may occur when walking down stairs or during contact sports).

With reference now to FIGS. 14-16, the housing 432 can be attached to the securing member 434. For example, the securing member 434 can have one or more engaging members 460a and 460b that are configured to engage with one or more corresponding engaging members 462a and 462b on the housing 432. The engaging members 460a and 460b can engage the engaging members 462a and 462b by a snap-fit connection, a friction-fit connection, a clasp, or any other suitable manner. For example, the engaging members 460a and 460b on the securing member 343 can include protrusions that fit into notches 462a and 462b in the housing 432 to snap the housing into the secured position. Other configurations are possible. In some embodiments, the housing 432 can be removably attached to the securing member 434 so that the housing 432 can be removed, for example, if the tightening mechanism 408 is to be repaired or replaced or cleaned.

With reference to FIGS. 17-20, which show the upper material 446 from a bottom view, lace channels 412a and 412b can be installed to direct the lace to the tightening mechanism 408. The lace channels 412a and 412b can be positioned inside the upper material 446 so that they are hidden from view once the shoe is fully assembled. Lace ports 464a and 464b can be positioned to receive the lace, for example, at an end of the gap between the first and second portions of the shoe. The lace channel tubes 412a and 412b can be coupled to the lace ports 464a and 464b and to the lace holes 438a and 438b, for example, by inserting the tubes 412a and 412b into the lace ports 464a and 464b and into the lace holes 438a and 438b. Adhesive backing tape 466 can be placed over the tubes 412a and 412b to hold them in place. An adhesive can be applied over the lace channel tubes 412a and 412b (e.g., onto the backing tape 466), and padding strips 468a and 468b can be adhered over the lace channel tubes 412a and 412b by the adhesive. The padding strips 468a and 468b can reduce discomfort caused by the tubes 412a and 412b pressing on the foot of a wearer when in use, and can also hide the shape of the tubes 412a and 412b. In some embodiments, the lace channels 412a and 412b can extend only partially across the collar of the shoe so that the lace can exit at locations on the side of the collar (e.g., at or near the midpoint of the collar). For example, FIGS. 1-3A show an example embodiment in which the lace extend outside the shoe across a portion of the collar and then enters the lace channels that guide the lace under the shoe material to the tightening mechanism. This configuration can allow for collar compression, simplified assembly, flexibility, and can eliminate pressure points, in some embodiments.

Figure 21:
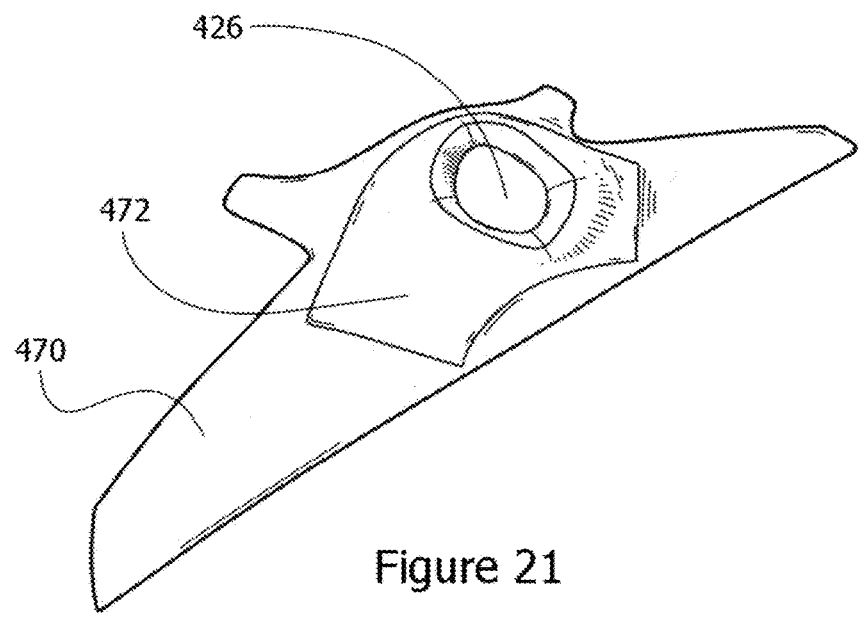
FIG. 21 shows a foxing layer of the show with a foam spacer applied thereto.
Figure 22:
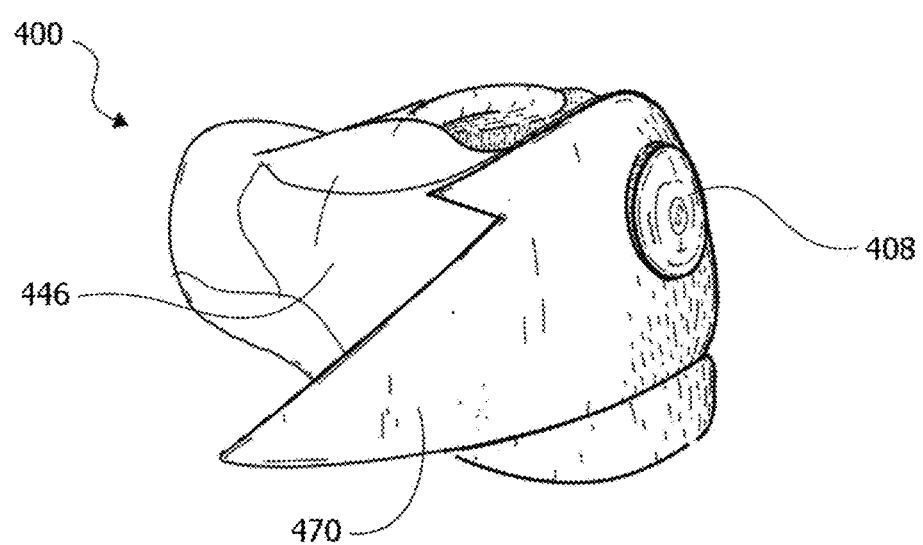
FIG. 22 shows the foxing layer being applied to the shoe.

With reference now to FIGS. 21 and 22, the concealing portion 416 of the shoe can be formed to conceal and/or to protect the tightening mechanism 408. In some embodiments, a foxing or outer layer 470 can be cut to a shape that is suitable to fit the contours of the article (e.g., the heel portion of the shoe 400). A compressible material, such as a foam 472 can be applied to the inside surface of the outer layer 470, such as by applying an adhesive, such as a polyurethane thermoplastic adhesive (e.g., Bemis brand 3206D polyurethane thermoplastic adhesive (e.g., 6 mil (0.006 inches), although other thicknesses can be used depending on the materials used and the intended use of the article)). Other adhesives can be used depending on the materials used and the intended use of the article. The outer layer 470 can be applied to the shoe 400, as shown in FIG. 22, for example. An adhesive can be applied (e.g., sprayed on) to the inside surface of the outer layer 470 and the outer layer 470 can be pressed against the underlying portions of the article (e.g., to the upper material 446). In some embodiments, a single application of an adhesive to the inside surface of the outer layer 470 can be used for adhering the foam 472 to the layer 470 and to adhere the layer 470 to the shoe 400. In other embodiments, separate adhesives and/or separate applications of the adhesive can be used for attaching the foam 472 and for attaching the layer 470 to the shoe 400. In some embodiments, the foam 472 can be attached (e.g., adhered) to the shoe 400 directly (e.g., over the upper material 446), and in some cases the layer 470 can then be applied over the top of the foam 472.

A hole 426 can extend through the layer 470 and the foam 472 and can be configured to receive the tightening mechanism 408 therein when the layer 470 is applied to the shoe 400. If a spray adhesive is applied to the inside surface of the layer 470, the hole can be masked off during application of the adhesive. Also, the foam 472 and/or the layer 470 surrounding the hole 426 can be colored (e.g., painted or dyed) so that it resembles the color and/or style of the outer appearance of the shoe 400. The foam 472 and/or the layer 470 can come in the color that matches or resembles the color of the shoe 400, or can be color matched, e.g., using dye additives. Also, the knob 416 or other components of the tightening mechanism 408 can have a color that is the same as, or similar to, the color and/or style of the outward appearance of the shoe 400 (e.g., to deemphasize the visual appearance of the tightening mechanism 408). The layer 470 can also be stitched to the shoe 400, or attached to the shoe 400 by other suitable manners.

The outer layer 470 and the foam 472 can have different shapes for different sizes and styles of shoes and for different types of articles. The foam 472 can have a shape and thickness configured to raise the outer layer 470 away from the underlying layer 446 by a height that is sufficient to cover part of, a majority of, substantially all of, or all of the sides of the knob 416, as discussed herein. In some embodiments, the layer 470 can be made from a polyurethane-backed nylon fabric, such as polyurethane-backed Cordura® fabric, which can have a low friction nylon interface that allows the user's fingers to slide easily across the surface of the layer 470 when turning the knob 416. Other low friction materials can also be used. In some embodiments, materials can be modified to add a low friction interface around the perimeter of the tightening mechanism. For example, direct injection molding, radio frequency welding, or debossing can be used to create the low friction interface. In some embodiments, a cover piece can be disposed around at least a portion of the tightening mechanism and can secure the fabric of the cover layer 470 (e.g., to the tightening mechanism). For example, a ring made of plastic (or other suitable material) can surround at least a portion of the tightening mechanism, and, in some embodiments, can form a low friction interface to allow a user's fingers to slide smoothly when operating the tightening mechanism.

Figure 23A:
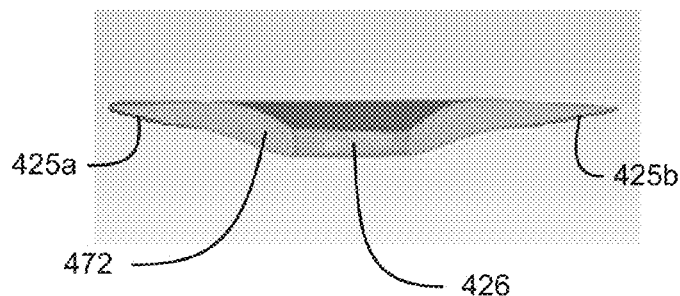
FIG. 23A shows a cross-sectional view of the foam spacer.
Figure 23B:
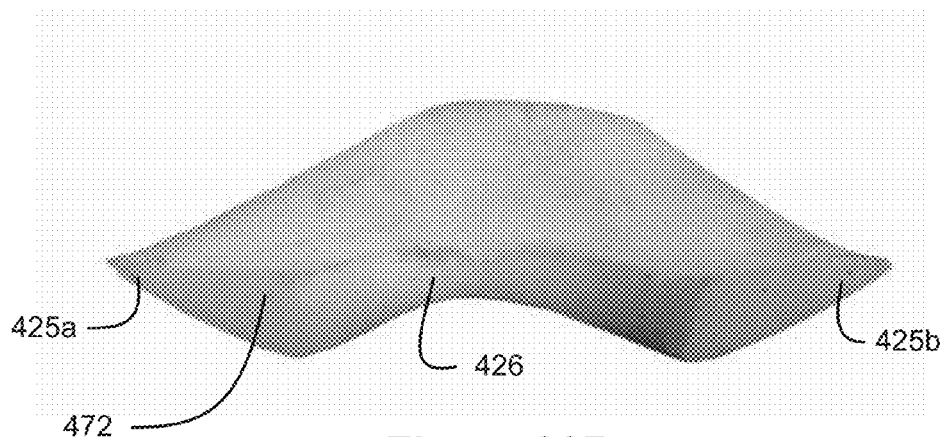
FIG. 23B shows a cross-sectional view of another example embodiment of a foam piece that can be used with some embodiment discussed herein.
Figure 23C:
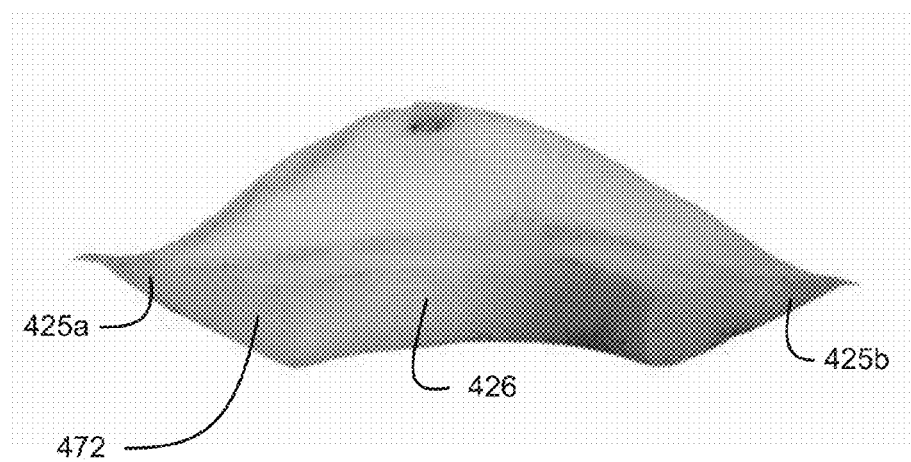
FIG. 23C shows a cross-sectional view of another example embodiment of a foam piece that can be used with some embodiment discussed herein.

FIG. 23A is a cross-sectional view of an example embodiment of a compressible member or foam piece 472 that can be used with some embodiments. The sides 425a and 425b of the foam piece 472 can be configured to wrap around the heel of the shoe and onto the side portions of the shoe. The sides 425a and 425b can be tapered to form a smooth transition at the ends of the foam piece 472 when mounted onto the shoe. The foam piece 472 can include the hole 426 therein. In some embodiments, the inside of the ring can chamfer outward to account for the curvature of the heel of the shoe 400. The foam piece 472 can be made from a variety of materials, such as, for example, Rubberlite V0525 Viso-Cel® slow rebound foam. Other open celled polyurethane foams can also be used, as well as other compressible materials. FIG. 23B shows a cross-sectional view of another example embodiment of a foam piece that can be used with some embodiment discussed herein. FIG. 23C shows a cross-sectional view of another example embodiment of a foam piece that can be used with some embodiment discussed herein. Various shapes of spacers (e.g., foam pieces 472) can be used depending on the shape and size of the article. For example, the embodiments of FIGS. 23B and 23C can have shorter side portions 425a and 45b than the embodiment of FIG. 23A, and the embodiment of FIG. 23C can have thinner ends on the side portions 425a and 425b than the embodiment of FIG. 23B.

FIG. 24 is a cross-sectional view of an example embodiment of a tightening mechanism 518 incorporated into an article, such as the shoe 100, the boot 200, the shoe 300, the shoe 400, or the other embodiments disclosed herein. The tightening mechanism 508 can include a housing 532, a spool 536, and a knob 516, similar to the tightening mechanism 408 described herein. The housing 532 can be mounted to a base material 546, such as the heel counter or upper material of a shoe. In some embodiments, the housing 532 can be attached directly to the base material 546 (as shown in FIG. 24), such as by stitching through a securing flange 554 of the housing 532, or by rivets, or by an adhesive, or other suitable manner. In some embodiments, the housing 532 can be coupled to the article using a securing member (e.g., similar to the securing member 434 discussed herein). In some embodiments, the base material 546 can include a hole therein for receiving the housing 532, such that a portion of the housing 532 is disposed rearward of the base material 546, thereby reducing the height by which the tightening mechanism 508 extends forward of the base material 546, which can facilitate the concealment of the tightening mechanism 508, and can reduce the height of the concealing area 514, which can improve the visual appearance of the article.

In some embodiments, padding 574 can be positioned rearward of the tightening mechanism 508 to provide comfort to the wearer and to prevent the tightening mechanism 508 from pressing against the portion of the wearer's body that contacts the article. For example, the tightening mechanism 508 can be incorporated into the tongue of a shoe or into a padded strap of a backpack or into other padded portions of wearable articles. In some embodiments, liners and other layers can be disposed rearward of the tightening mechanism 508, but are not shown in FIG. 24 for simplicity.

A concealing portion 514 can at least partially surround the tightening mechanism 508. The concealing portion 514 can include a compressible area 576, which can be a foam material, as discussed herein. FIG. 24 shows the concealing portion 514 in an uncompressed position, and FIG. 25 shows the concealing portion 514 in a compressed position in which the compressible area is compressed (e.g., by a compressing force applied by a user's fingers) to expose the knob 516. In some embodiments, the compressible area 576 can be disposed between the base material 546 and an outer layer 570. In some embodiments, some or all of the area surrounding the tightening mechanism 508 can be substantially incompressible. For example, the area 576 of FIG. 24 can include a substantially incompressible material (e.g., a rigid plastic material or a rigid foam material).

In FIG. 26, the concealing portion 514 can include a first area 576a that is more compressible than a second area 576b. The more compressible area 576a can be positioned radially inward from the less compressible area 576b. For example, the more compressible area 576a can surround at least a portion of the tightening mechanism 508, and the less compressible area 576b can surround at least a portion of the more compressible area 576a. In some embodiments, both the first compressible area 576a and the second compressible area 576b can include compressible foam, and the foam of the first compressible area 576a can be of a lower density and higher compressibility than the foam of the second compressible area 576b. In some embodiments, the second area 576b is substantially not compressible. The first compressible area 576a can have a radial width of at least about 5 mm, at least about 10 mm, at least about 15 mm, no more than about 20 mm, between about 5 mm and 15 mm, and/or about 10 mm. In some embodiments, the first compressible area 576a can be wide enough to allow a user's fingers to compress the first compressible area 576a without directly applying a compressing force onto the second area 576b. In some embodiments, the first compressible area 576a can have a width that is small enough that a compressing force applied by a user's finger directly applies a compressing force to both the first area 576a and the second area 576b.

Figure 29:
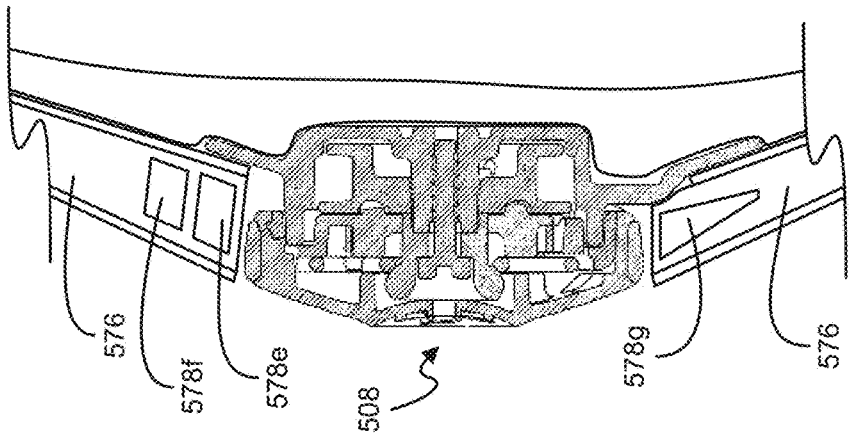
FIG. 29 shows a schematic cross-sectional view of a tightening mechanism with a concealing portion having cavities formed therein.
Figure 28:
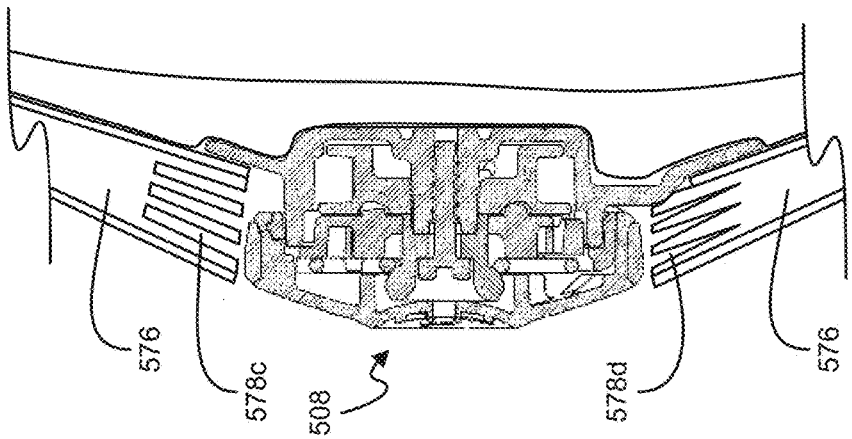
FIG. 28 shows a schematic cross-sectional view of a tightening mechanism with a concealing portion having grooves formed therein.

In some embodiments, the compressible area 576 can include a recess 578a configured to facilitate compression of the compressible area 676. In some embodiments, the recess 578a can be disposed directly behind a layer of the compressible material (e.g., foam), so that when a compressing force is applied, the layer of the compressible material can collapse down into the recess 578a to expose the tightening mechanism 508. In some embodiments, the recess 578b can be tapered (e.g., as shown in the lower portion of FIG. 27) so that a portion of the collapsible area 576 nearer to the tightening mechanism 508 can collapse more easily and/or further than a portion of the collapsible area 576 that is radially further from the tightening mechanism 508. In some embodiments, the recess can include one or more cutouts or grooves 578c formed in the compressible material (as shown in FIG. 28). Multiple grooves 578c can be included such that one or more extensions of the compressible material can extend between the grooves 578C. In some embodiments, the grooves 578d can be tapered (e.g., as shown in the lower portion of FIG. 28) so that a portion of the collapsible area 576 nearer to the tightening mechanism 508 can collapse more easily and/or further than a portion of the collapsible area 576 that is radially further from the tightening mechanism 508. In some embodiments, the recess can include a cavity 578e that is a volume surrounded on all sides by the compressible material (e.g., foam). In some embodiments, the recess can include multiple cavities 578e and 578f (as shown in the upper portion of FIG. 29). In some embodiments, the size or distribution of the plurality of cavities 578e and 578f can vary such that a portion of the collapsible area 576 nearer to the tightening mechanism 508 can collapse more easily and/or further than a portion of the collapsible area 576 that is radially further from the tightening mechanism 508. Although the upper portion of FIG. 29 shows only two cavities 578e and 578f for simplicity of illustration, some embodiments can include a larger number of cavities formed in the compressible material. In some embodiments one or more individual cavities 578g can be tapered (as shown in the lower portion of FIG. 29), so that a portion of the collapsible area 576 nearer to the tightening mechanism 508 can collapse more easily and/or further than a portion of the collapsible area 576 that is radially further from the tightening mechanism 508

Figure 27:
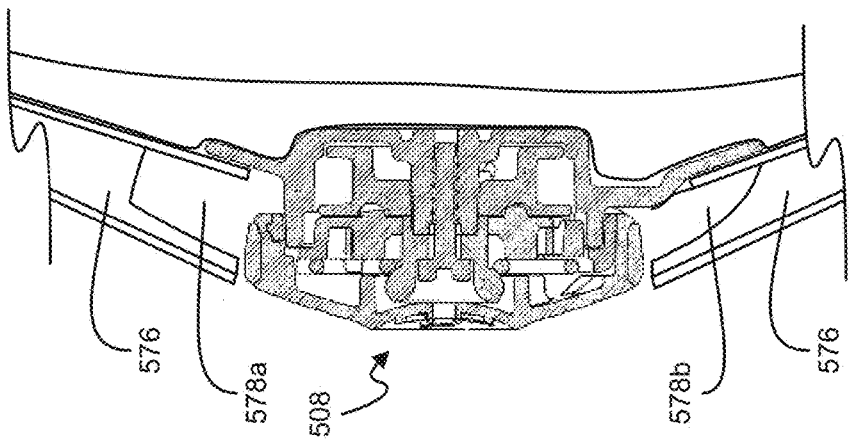
FIG. 27 shows a schematic cross-sectional view of a tightening mechanism with a concealing portion having a recess formed therein.

The various recess types 578a-578g shown in FIGS. 27-29 can be used individually or can be combined with others of the recess types 578a-578g to provide various alternative configurations. In some embodiments, a recess structures 578a-578g can extend rotationally to form arcuate recesses that at least partially surround the tightening mechanism 508.

In some embodiments, the tightening mechanism 508 can include one or more shield elements 558. The shield element 558 can be, for example, integrally formed with the housing 532, or the shield element 558 can be a separate component from the housing 532. The shield element 558 can be a rigid extension that covers at least part of the side of the knob 516. The shield element 558 can be configured to protect to the knob 516, as discussed elsewhere herein. Various embodiments disclosed herein (e.g., the embodiments of FIGS. 24-29 and 31-32) can be modified to include a shield element 558 similar to that described in connection with FIG. 30. In some embodiments an additional shield element can be positioned generally opposite the shield element 558 shown in FIG. 30. For example, shield elements 558 can be positioned at about 6-o'clock and at about 12-o'clock, to provide protection to the tightening mechanism 508, as discussed herein.

In some embodiments, the compressible material 576 can be enclosed. For example, as shown in the upper portion of FIG. 31, the base material 546 can wrap around the compressible material 576 such that the compressible material 567 is sandwiched between portions of the base material 546. In some embodiments, an outer layer 570 can extend around the compressible material 576 and can be coupled to the base material 546, as shown in the lower portion of FIG. 31, or the base material 546 can extend around the compressible material and can be coupled to the outer layer 570. The base material 546 and outer layer 570 can be coupled together, for example, by stitching, or rivets, or an adhesive, or any other suitable manner. In some embodiments, a layer separate from the base material 546 and the outer layer 570 can extend between the outer layer 570 and the base material 546 between the compressible material 576 and the knob 516, and the layer can be flexible so that it can be collapsed or displaced to expose the knob 516 (e.g., when a user applied a compressing force). The flexible layer can be positioned between the compressible material 576 and the knob 516, thereby separating the knob 516 from the compressible material 576, which can prevent the compressible material 576 from contacting the knob 516 when the compressible material 576 is deflected in the compressed state. If the deflected compressible material 576 contacts the rotatable knob it can interfere with rotation of the knob 516 and in some cases can become pinched by the knob 516. Thus, the layer separating the compressible material 576 from the knob 516 can prevent the compressible material 576 from interfering with operation of the knob 516.

In some embodiments, the compressible material 576 can be uncovered, as shown in FIG. 32A. In some embodiments, slow recovery memory foam can be used as the flexible material 576, although various other compressible materials can also be used. In some embodiments, the top of the compressible material 576 can define the outer surface 520 of the concealing portion 514. The outer surface 520 of the compressible material 576 can be colored or patterned to coordinate with the color and/or styling of the article, thereby visually deemphasizing the concealing area 514.

Many variations can be made to the embodiments disclosed herein. For example, in some embodiments, substantially incompressible guarding members (e.g., rigid plastic strips) can be insert molded into a compressible material to add rigidity and additional guarding to certain areas of the concealing portion 514 (e.g., the area below and/or above the tightening mechanism). For example, with reference to FIG. 26, in some embodiments, the first area 576a surrounding the tightening mechanism 508 can be substantially incompressible. For example, the first area 576a can include a guarding member (e.g., made of a rigid plastic material), which can be, for example, insert molded into the foam to create guards that protect and/or conceal the tightening mechanism 508.

Figure 32C:
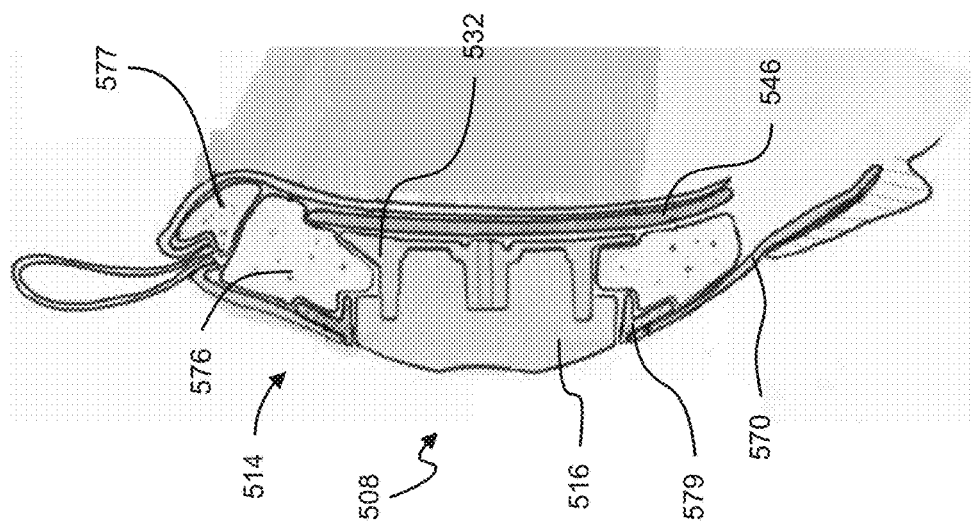
FIG. 32C shows yet another example implementation of a tightening mechanism 508 and concealing portion.
Figure 32B:
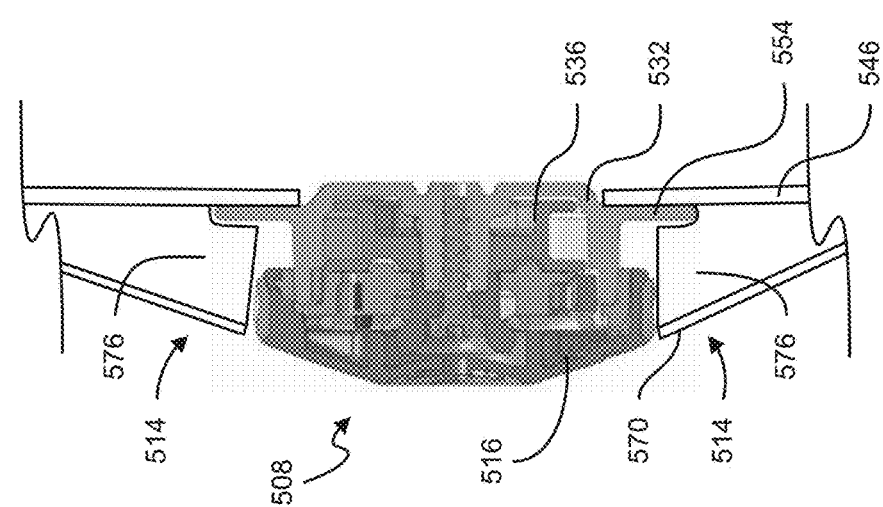
FIG. 32B shows an example implementation of a tightening mechanism and concealing portion.

FIG. 32B shows an example implementation of a tightening mechanism 508 and concealing portion 514, which can have features similar to, or the same as, the embodiments shown in FIGS. 24-32A. In FIG. 32B, the tightening mechanism 508 can include a securing flange 554 that is flatter than those shown in FIGS. 24-32A. The size and shape of the securing flange 554, as well as the other features of the tightening mechanism 508 can vary depending on the size and shape of the article with which the tightening mechanism 508 is applied. For example, in FIG. 32B, the base material 546 can be, for example, a heel counter of a shoe, and the base material 546 can have a hole that receives a portion of the tightening mechanism 508 (e.g., a bottom of the housing 532) therein. In some embodiments, the base material 546 (e.g., heel counter) can be substantially flush with the bottom surface of the housing 532, as shown in FIG. 32B. Although not shown in FIG. 32B, padding or lining layers can be positioned rearward of the tightening mechanism 508, for example, to separate the tightening mechanism 508 from the wearer. The embodiment shown in FIG. 32B can be modified to incorporate the features shown and discussed in connection with FIGS. 24-32A.

FIG. 32C shows another example implementation of a tightening mechanism 508 and concealing portion 514, which can have features similar to, or the same as, the embodiments shown in FIG. 24-32B. A housing 532 can be mounted onto a base material 546 (e.g., heel counter). In some embodiments, the base material 546 (e.g., heel counter) does not include a hole that receive a portion of the housing 532 therein. The housing 532 can be secured (e.g., stitched or adhered) to the outside of the base material 546. An outer material 570 can be elevated at the concealing portion 514, e.g., by a spacer 576, which can be a foam or plastic material, and can be compressible or substantially uncompressible, as discussed herein. In some embodiments, additional foam can be used around the spacer 576, such as collar foam 577 that surrounds a collar portion of a shoe. In some embodiments, a grommet 579 can surround all or a portion of the tightening mechanism 508. The grommet 579 can be a ring. The grommet 579 can be positioned between the spacer 576 and the outer material 570. In some embodiments, the outer material 570 can be stitched, adhered, or otherwise secured or coupled to the grommet 579. The grommet 579 can be rigid or generally rigid, so that when the user presses down on the grommet 579, it compresses an area of the concealing portion 514 positioned under the grommet 579, which in some cases can be a full 360° area surrounding the tightening mechanism 508, or a portion thereof.

Figure 33:
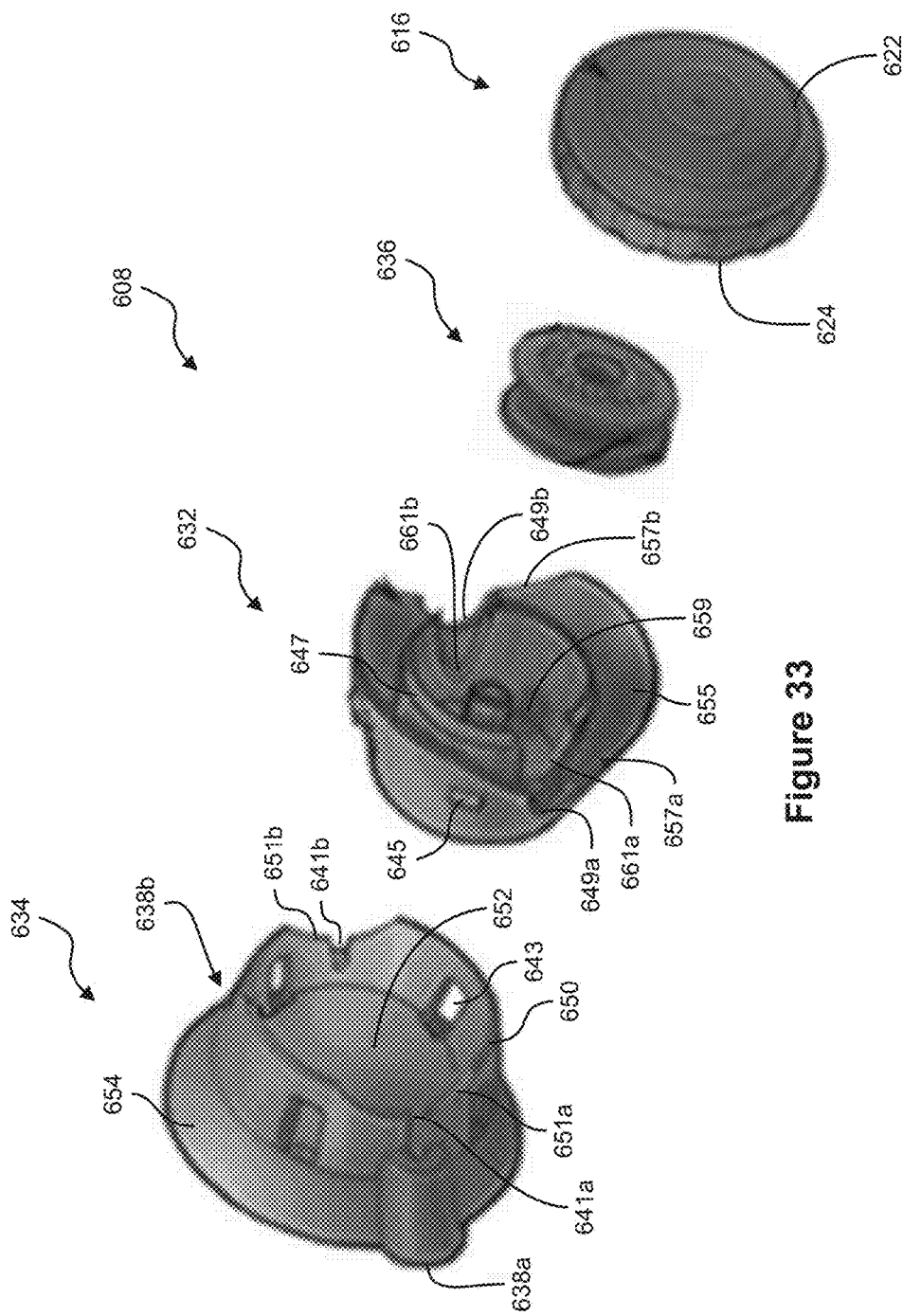
FIG. 33 is an exploded isometric view of a tightening mechanism.

FIG. 33 is an exploded isometric view of a tightening mechanism 608, which can be used with an article (e.g., the shoe 100, the boot 200, the shoe 300, or other embodiments disclosed herein). The tightening mechanism 608 can include a housing 632, a securing member 634, a spool 636, and a knob 616. The spool 636 can be mounted into the housing 632 such that the spool 636 is rotatable with respect to the housing 632. A lace can be coupled to the spool 636 so that rotation of the spool 636 in a tightening direction gathers the lace onto the spool 636. The spool 636 can engage the knob 616, so that rotation of the knob 616 can cause rotation of the spool 636, thereby allowing the lace to be tightened by rotating the knob 616. The knob 616 can include a top surface 622 and sides 624. In some embodiments, the spool 636 and the knob 616 can be configured similarly to the spool 436 and knob 416 discussed above. Many other configurations can be used for the tightening mechanism 608.

The securing member can have side walls 650 that surround a recess 652. The side walls 650 can have a first indented portion 651a and a second indented portion 651b, which can be position on generally opposite sides of the securing member 634 (e.g., on the right and left sides thereof). One or more holes or notches 641a and 641b can allow a lace to pass from outside the securing member 634 into the recess 652. For example, notches 641a and 641b can be formed in the indented portions 651a and 651b of the side walls 650. The securing member 634 can include engagement features (e.g., slots 643) which can be configured to engage with engagement features (e.g., teeth 645) on the housing 632 to allow the housing 632 to be secured to the securing member 634 (e.g., by a snap-fit engagement). The securing member 634 can include a securing flange 654, which can extend radially outwardly from the base of the side walls 650. In some embodiments, lace holes 638a and 638b are formed on the securing member 634 (e.g., on the bottom thereof), and lace channels can lead from the lace holes 638a and 638b to the notches 641a and 641b or holes that allow the lace to enter the recess 652.

The housing 632 can include side walls 655 and indented portions 657a and 657b which can align generally with the indented portions 651a and 651b of the securing member 634. In some embodiments, internal side walls 647 surround a recess 659. A gap can be formed between the side walls 655 and the internal side walls 647. One or more notches 649a and 649b or holes can be formed in the side walls 655 (e.g., at the base of the indented portions 657a and 657b), and one or more notches 661a and 661b or holes can be formed in the internal side walls 647. The notches or holes can allow the lace to pass into the recess 659, and for example, can align with the holes or notches 641a and 641b formed in the securing member 634.

Figure 34:
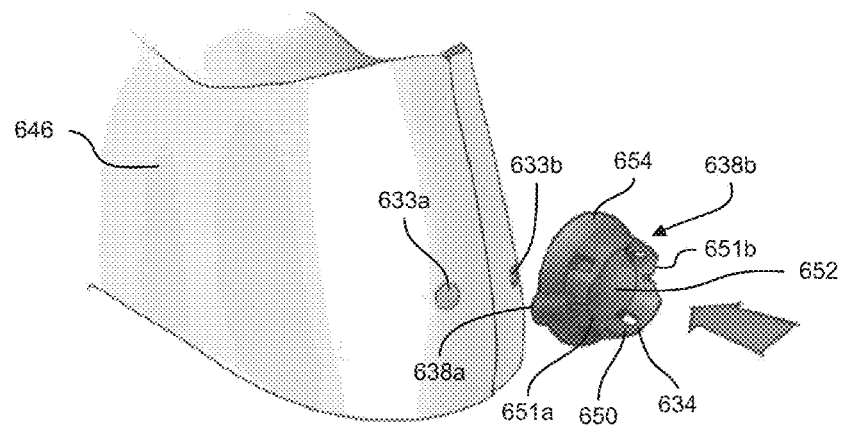
FIG. 34 shows a securing member being coupled to an upper material of a shoe.
Figure 35A:
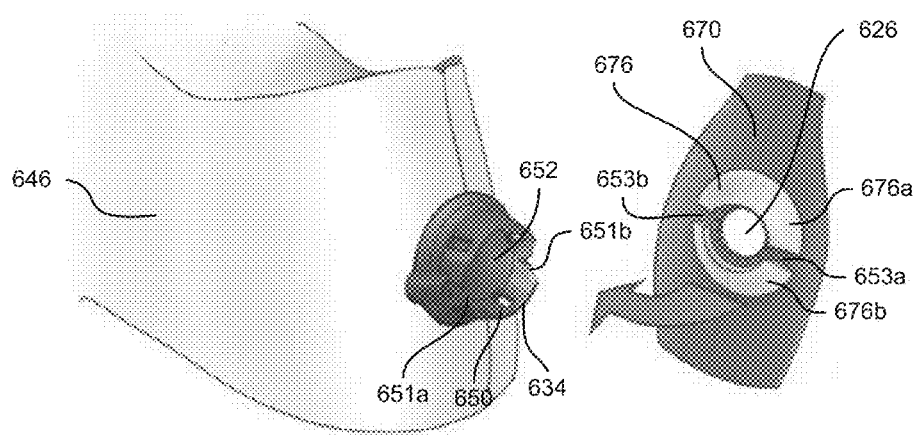
FIG. 35A shows a foxing layer and spacer being applied over the securing member.
Figure 35B:
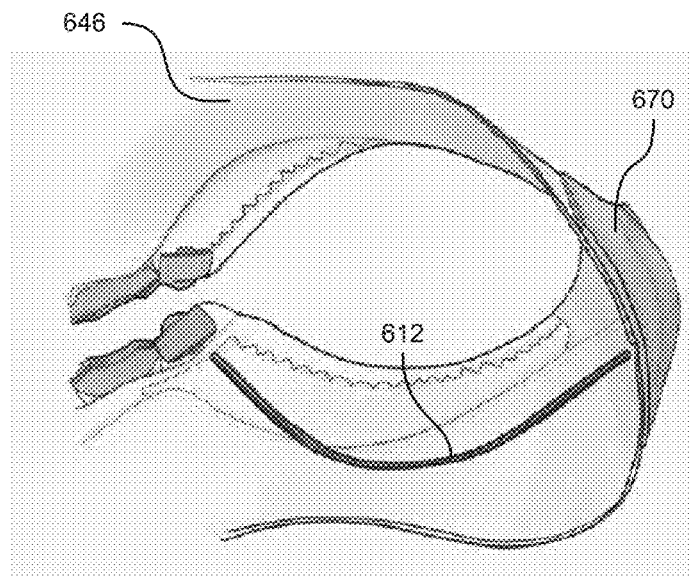
FIG. 35B shows a lace channel being applied to the upper material.

With reference to FIGS. 34 and 35A, a securing member 634 can be secured to the article (e.g., to an upper material 646 of a shoe). For example, securing flange 654 can be stitched to the upper material 646, or secured thereto by other suitable securing mechanisms. The upper material 646 can include one or more lace holes 633a and 633b which can align with the lace holes 638a and 638b on the securing member 634. As shown in FIG. 35B, lace channels 612, similar to those discussed in connection with FIGS. 17-20, can be applied inside the upper material 646 and can direct the lace to the lace holes 633a and 633b and to the securing member 634. In some embodiments, the tightening mechanism 608 is disposed outside the upper material 646, and the upper material 646 does not include a hole that allows a portion of the tightening mechanism to be disposed rearward of the upper material 646.

Figure 35C:
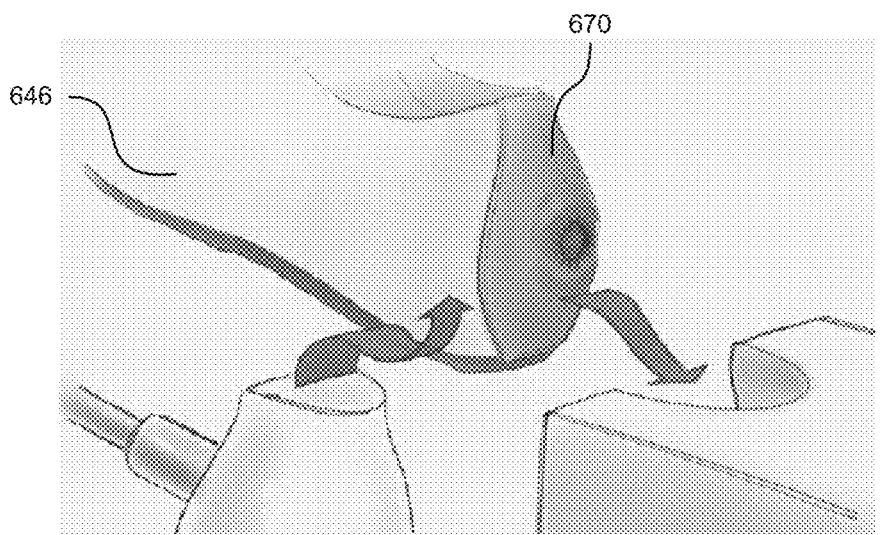
FIG. 35C shows the assembly being back-part molded.

A foxing or outer layer 670 can be positioned over the securing member 634. A spacer 676 can attach to the underside of the layer 670 (e.g., using an adhesive). The spacer 676 can be a compressible material, a rigid material, or a semi-rigid material. The spacer 676 can have a first or upper portion 676*a* and a second or lower portion 676*b* separated by gaps 653*a* and 653*b* or thinner portions of the spacer 676. A hole can extend through the outer layer 670 and through the spacer 676. The spacer 676 can be configured to fit around the outside of the side walls 650 of the securing member 634 when the layer 670 is mounted onto the article, and the gaps 653*a* and 653*b* in the spacer 676 can align with the indented portions 651*a* and 651*b* of the side walls 650 on the securing member 634. In some embodiments, the gaps 653*a* and 653*b* can provide paths for the lace to pass through. In some embodiments, the spacer 676 can extend a full 360 degrees around the opening 626, and the gaps 653*a* and 653*b* can be omitted. The hole 626 through the layer 670 and spacer 676 can align over the recess 652 when the layer 670 is mounted onto the article. In some embodiments, the assembly can be back part molded, as shown, for example, in FIG. 35C.

Figure 36:
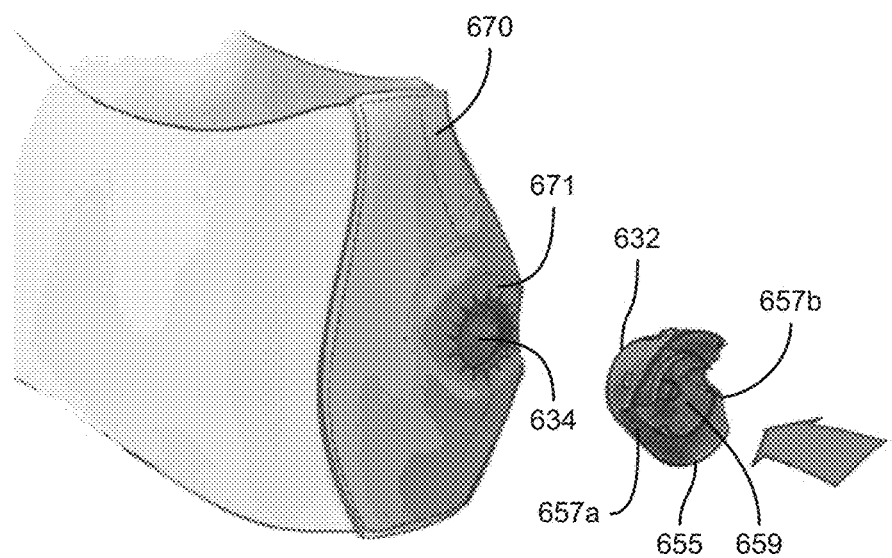
FIG. 36 shows a housing being coupled to the securing member.

As can be seen in FIG. 36, the housing 632 can be mounted onto the securing member 634. In some embodiments, a portion 671 of the foxing or outer layer 670 surrounding the hole 626 can extend over the securing member 634 so that the portion 671 of the layer 670 is pressed down into the recess 652 of the securing member 634 when the housing 632 is inserted therein. In some embodiments, because the portion 671 of the layer 670 is be pinched between the housing 632 and the securing member 634, there is no gap between the edges of the foxing layer 670 and the tightening mechanism 608, which can prevent debris from entering a space around the tightening mechanism 608.

As discussed above, the housing 632 and the securing member 634 can include corresponding engagement features that are configured to secure the housing 632 to the securing member 634, such as, for example, by a snap fit, a friction fit, etc. In some embodiments, the housing 632 can be removably attachable to the securing member 634, so that the housing 632 can be removed (e.g., for repair, replacement, or cleaning). Because the housing 632 is inserted over the foxing layer 670, the housing 632 can be removed from the securing member 634 without removing or cutting the foxing layer 670.

Figure 37A:
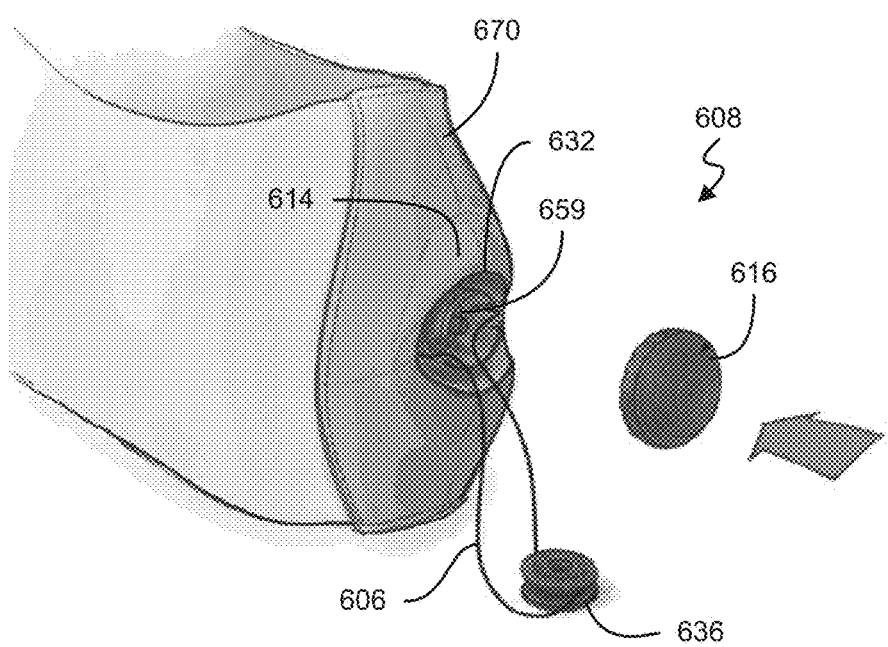
FIG. 37A shows a spool and knob being coupled to the housing.

As shown in FIG. 37A, the spool 636 can receive a lace 606 and can be rotatably supported in the recess 659 of the housing 632. The knob 616 can be rotatably mounted onto the housing 632 and can be configured such that rotating the knob 616 can tighten the lace 606 by causing the spool 636 to rotate. In some embodiments, the side walls 655 and/or the side walls 650 can surround at least a portion of the side 624 of the knob 616, thereby forming rigid shielding elements that can protect the knob 616 from accidental actuation. The indented portions 657*a* and 657*b* and/or 651*a* and 651*b* can expose portions of the side 624 of the knob 616, to allow a user to grip the sides 624 of the knob 616 (e.g., for tightening). A concealing portion 614 of the article can at least partially surround the sides 624 of the knob 616 to conceal or protect the tightening mechanism 608. For example, the spacer 676 can press the foxing layer 670 up around the tightening mechanism 608. In some embodiments, the concealing portion 614 can be higher at some areas surrounding the tightening mechanism 608 than at other surrounding areas.

Figure 37B:
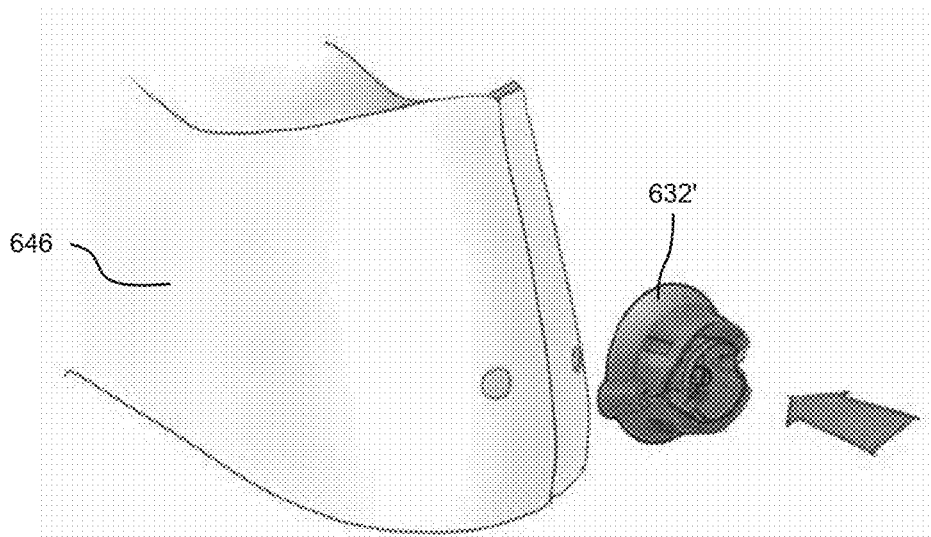
FIG. 37B shows an example embodiment having a single piece that incorporates a securing member and a housing.
Figure 37C:
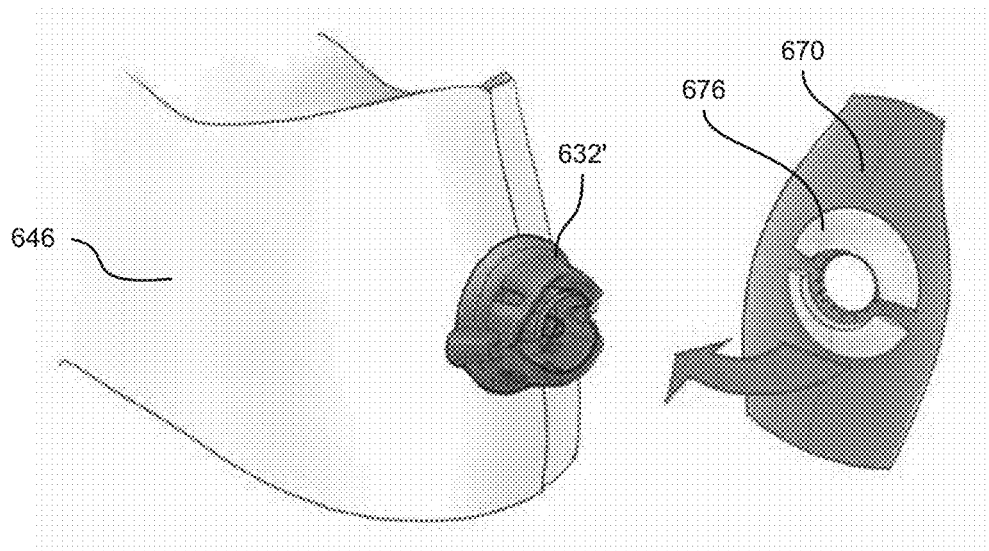
FIG. 37C shows a foxing layer being applied over the single piece that incorporates the securing member and the housing.

Many variations are possible. For example, with reference to FIG. 37B, in some embodiments, the housing 632 can be incorporated into the securing member 634, for example, as a single integrally formed piece 632' that can be attached directly to the article. The housing piece 632' can combine the features of the housing 632 and the securing member 634 discussed above. Because the housing piece 632' can be a single integral piece, the engagement features of the securing member 634 and housing 632 can be omitted in the housing piece 632'. As shown in FIG. 37C, the outer layer (e.g., foxing) 670 can be applied over the housing piece 632', in a manner similar to that discussed in connection with FIG. 35A.

Figure 38:
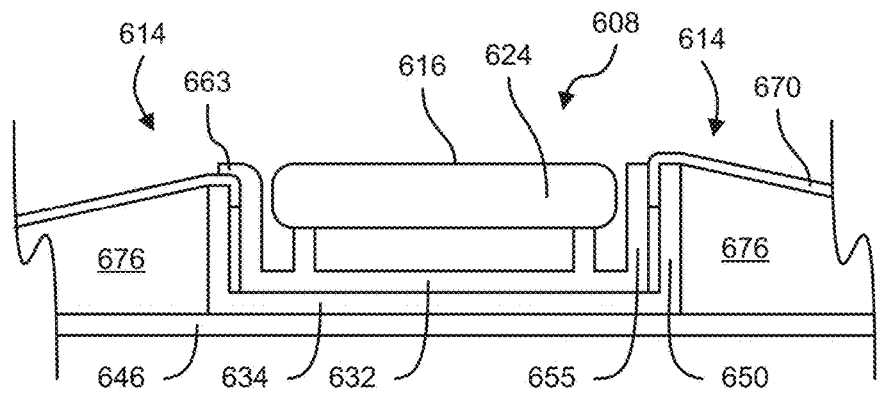
FIG. 38 is a schematic cross-sectional view of a tightening mechanism and concealing portion taken in a plane that intersects shielding elements.

FIG. 38 is a schematic cross-sectional view of the tightening mechanism 608 and concealing portion 614 taken in a plane (e.g., a vertical plane) that intersects the shielding elements (e.g., the side walls 650 and/or 655). One or both of the side walls 650 and 655 can extend upward at least as far as the sides 624 of the knob 616 in the plane of FIG. 38, such that the sides 624 of the knob 616 can be partially, mostly, entirely, or substantially entirely covered by the concealing area 614 (similar to the discussion above, e.g., of FIGS. 4-6). In some embodiments, both the side wall 650 of the securing mechanism and the side wall 655 of the housing 632 can extend upward at least as far as to the top of the knob side 624 (e.g., to substantially the same height, as shown on the right side of FIG. 38). In some embodiments, the side wall 655 of the housing 632 can extend higher than the side wall 650 of the securing mechanism 634 (as shown on the left side of FIG. 38). In some embodiments, the side wall 655 of the housing 632 can have a flange portion 663 that extends radially outwardly over at least a portion of the side wall 650. The flange 663 can clamp the foxing layer 670 down against the side wall 650.

Figure 39:
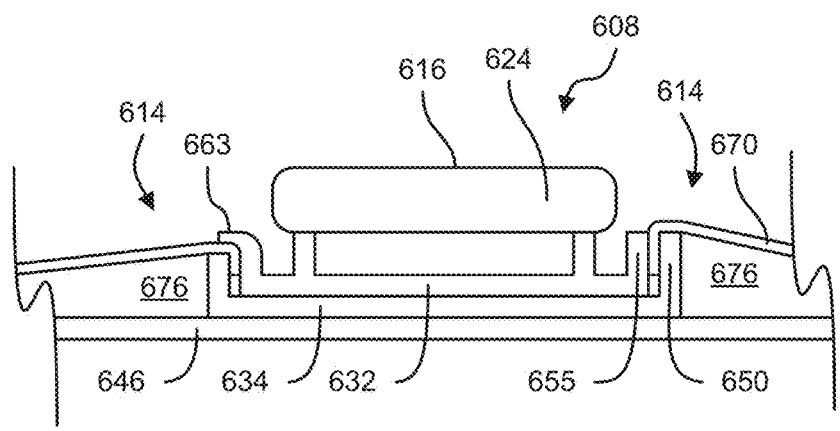
FIG. 39 is a schematic cross-sectional view of the tightening mechanism and concealing portion taken in a plane in which the concealing portion has a reduced height that is lower than in the plane of FIG. 38.

FIG. 39 is a schematic cross-sectional view of the tightening mechanism 608 and concealing portion 614 taken in a plane in which the concealing portion 614 has a reduced height that is lower than in the plane of FIG. 38. For example, FIG. 39 can be taken in a plane (e.g., a horizontal plane) that intersects the indented portions 657*a* and 657*b* and/or 651*a* and 651*b*. One or both of the side walls 650 and 655 can extend upward to a location rearward of the knob 616, such that the sides 624 of the knob 616 can be partially, mostly, entirely, or substantially entirely exposed from a side direction. The side walls 650 and 655 can extend upward to substantially the same height (as shown on the right side of FIG. 39). In some embodiments, the side wall 655 of the housing 632 can extend higher than the side wall 650 of the securing mechanism 634 (as shown on the left side of FIG. 39). The flange portion 663 can clamp the foxing layer 670 down against the indented portions 651*a* and 651*b* of the side wall 650, which can prevent the layer 670 from obstructing the reduced height portions of the concealing area 614. The spacer 676 can have a greater height for the portions in the plane of FIG. 38 than for the portions of the spacer 676 in the plane of FIG. 39.

Figure 40:
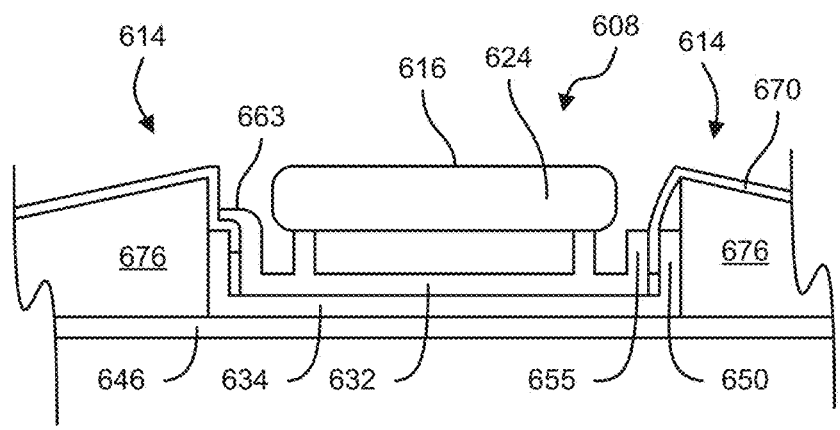
FIG. 40 is a schematic cross-sectional view of the tightening mechanism and concealing portion in which the concealing portion can be compressed.

FIG. 40 is a schematic cross-sectional view of the tightening mechanism 608 and concealing portion 614 in which the concealing portion 614 can be compressed to allow a user to actuate the knob 616. For example, the cross-section of FIG. 40 can be taken in a plane (e.g., a horizontal plane) that intersects the indented portions 657*a* and 657*b* and/or 651*a* and 651*b*. The configuration shown in FIG. 40 can be similar to, or the same as, the configuration of FIG. 39 in many regards. The spacer 676 can have a height that is greater than the height of the side walls 650 and/or 655. In the uncompressed state, shown in FIG. 40, the concealing portion 614 can extend upward at least as far as the sides 624 of the knob 616 such that the sides 624 of the knob 616 can be partially, mostly, entirely, or substantially entirely covered by the concealing area 614 (similar to the discussion above, e.g., of FIGS. 4-6). The spacer 676 material can be a compressible so that the concealing portion 614 can be compressed to a compressed state (not shown). In the compressed state, the concealing portion 614 can have a reduced height similar to that shown and discussed in connection with FIG. 39, such that the user can actuate the knob 616. The left side of FIG. 40 shows a configuration in which the side wall 655 includes a flange 663, as discussed above, and the right side of FIG. 40 shows a configuration that does not include the flange 663. In some embodiments, the compressible areas of the concealing portion 614 can extend around the tightening mechanism 608 by a full 360 degrees, instead of having a portion with rigid shield elements (as shown in FIG. 38).

Figure 41:
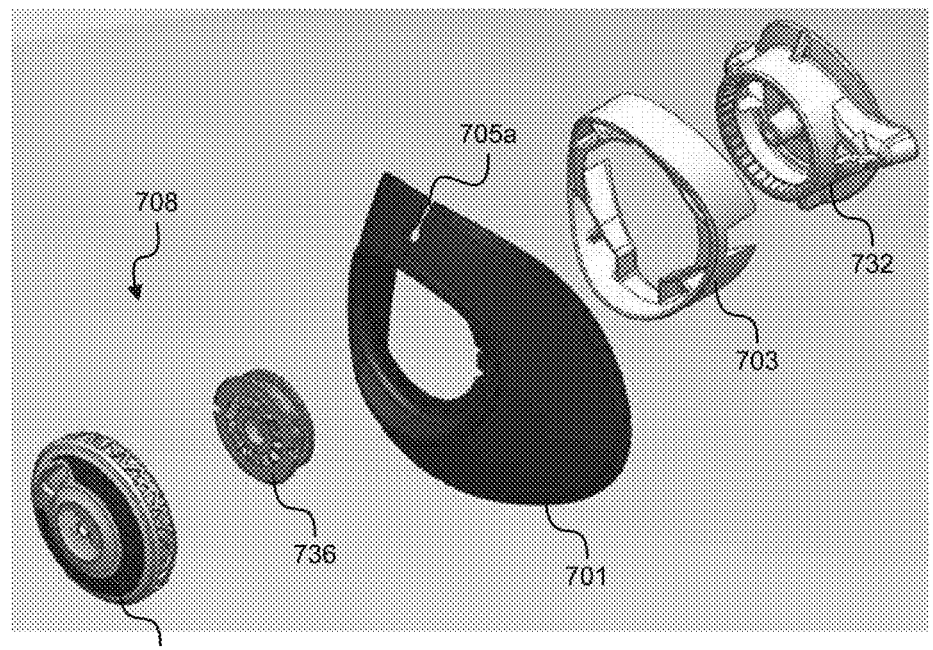
FIG. 41 is an exploded view of an example implementation of a tightening mechanism and a concealing portion.
Figure 42:
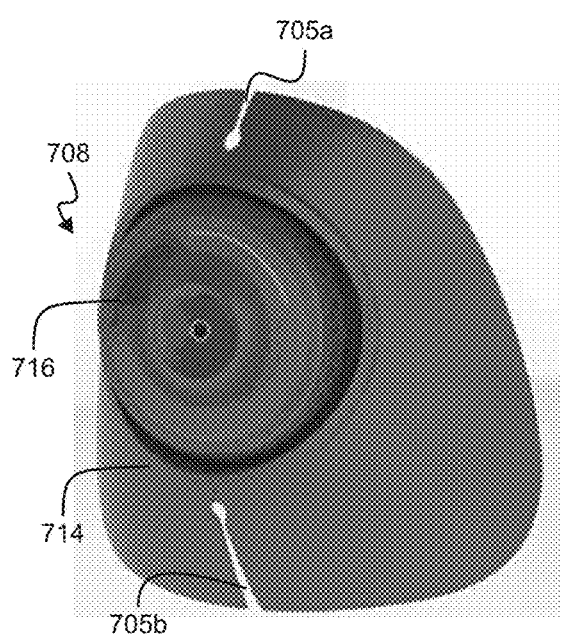
FIG. 42 shows the assembled tightening mechanism and concealing portion of FIG. 41.
Figure 43:
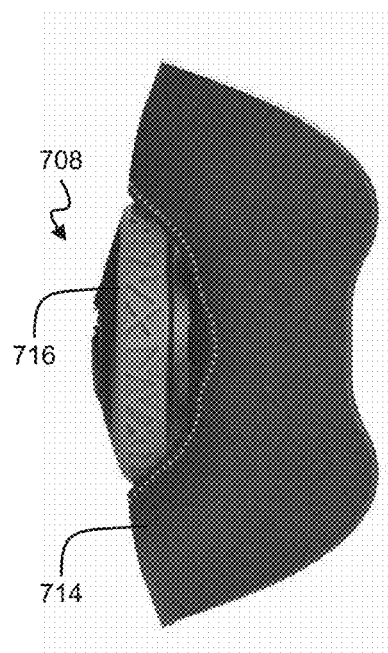
FIG. 43 is a side view of the tightening mechanism and concealing portion of FIG. 41.

FIG. 41 is an exploded view of an example implementation of a tightening mechanism 708 and a concealing portion 714, which can be used in connection with various embodiments disclosed herein. FIG. 42 shows the assembled tightening mechanism 708 and concealing portion 714. FIG. 43 is a side view of the tightening mechanism and concealing portion 714. The tightening mechanism 708 can include a housing 732, a spool 736, and a knob 716, which can have features similar to, or the same as the housing 432, spool 436, and knob 416 described above. A shaping member 701 can be disposed over the housing 732 to conceal and/or protect the tightening mechanism 708 (e.g., to protect the knob 716) as discussed herein. The shaping member 701 can be shaped according to the size and shape of the article (e.g., a heel of a shoe) to integrate the tightening mechanism 708 into the appearance of the article. In some embodiments, an outer material (e.g., a foxing) can be disposed over the shaping member 701, such that the shaping member 701 acts as a spacer to elevate the outer material as discussed herein. In some embodiments, the shaping member 701 can be rigid and can be configured to engage with the housing 732 to position the shaping member 701 and housing 732 at appropriate locations on the article. In some embodiments, an air gap can be formed under the shaping member 701, e.g., between shaping member 701 and the housing 732. In some embodiments, the shaping member 701 can be flexible or somewhat flexible, e.g., to allow the shaping member 701 to conform to the particular contours of an article. A supporting member 703 can be disposed between the housing 732 and the shaping member 701, in some embodiments, to provide support to the shaping member 701 (e.g., to maintain the shape of a flexible shaping member 701). In some embodiments, the supporting member 703 can be omitted. In some embodiments, the shaping member 701 can include one or more cutouts 705a and 705b (e.g., slits) to facilitate bending of the shaping member 701 to conform to the shape of the article. In some embodiments, the shaping member 701 and/or the supporting member 703 can be configured to conceal and/or protect the tightening mechanism 708 more at some locations than at other locations surrounding the tightening mechanism 708, as discussed herein. The concealing portion 714 can have recesses, cutouts, or scalloped areas, etc. that can provide open portions where the side of the knob 716 is exposed, thereby allowing a user to actuate the knob 716, as discussed herein.

FIG. 44 is a side view of a shoe having a tightening mechanism 808 and a concealing portion 814 at least partially surrounding the tightening mechanism 808. In some embodiments, the tightening mechanism 808 can be similar to the tightening mechanism 708 discussed above, although other embodiments disclosed herein can also relate thereto. FIG. 45 shows a shaping member 801, which can be similar to the shaping member 701 discussed above, with a housing 832 of the tightening mechanism 808 mounted thereto. The knob 816 is not shown in FIG. 45. FIG. 46 is a cross-sectional view of the shoe of FIG. 44 showing the housing 832 coupled to the shoe and the concealing portion 814. As discussed in connection with various embodiments herein, the concealing portion 814 an provide areas (e.g., on the sides) in which the tightening mechanism 808 is exposed sufficiently to allow a user to actuate the tightening mechanism 808.

FIG. 47 is a side view of a shoe having a tightening mechanism 908 and a concealing portion 914 at least partially surrounding the tightening mechanism 908. FIG. 48 shows another view of the shoe of FIG. 47. FIG. 49 shows a spacer 976, which can be configured to provide the shape of the concealing portion 914 of FIGS. 47 and 48. As discussed in connection with various embodiments herein, the concealing portion 914 can provide areas (e.g., on the sides) in which the tightening mechanism 908 is exposed sufficiently to allow a user to actuate the tightening mechanism 908.

Figure 50:
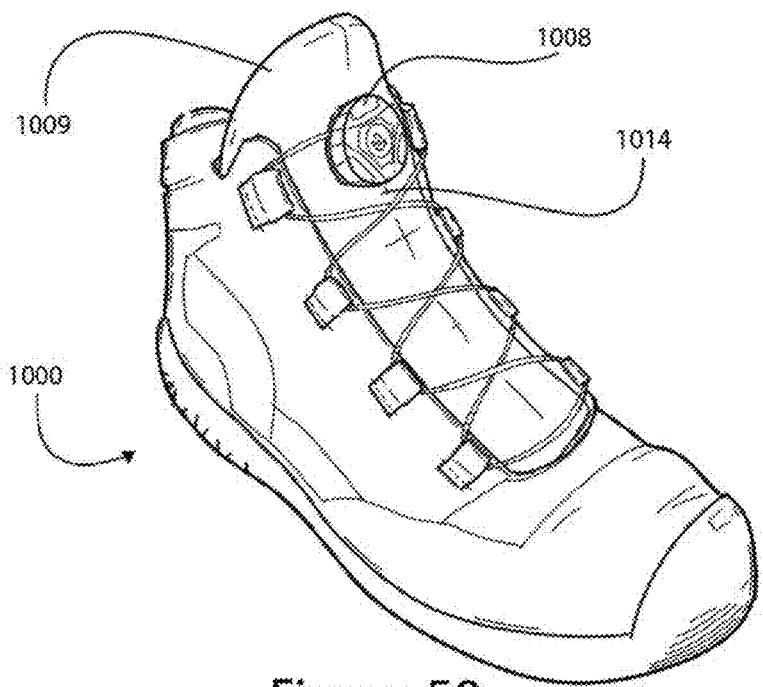
FIG. 50 is an isometric view of a boot having a tightening mechanism mounted onto the tongue of the boot and a concealing portion at least partially surrounding the tightening mechanism.
Figure 51:
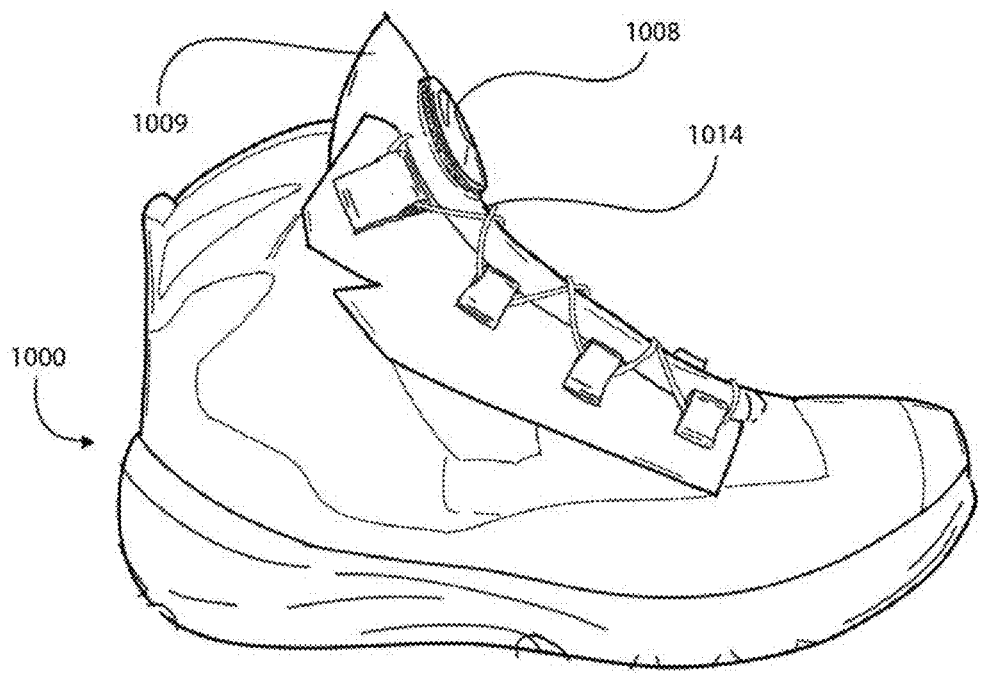
FIG. 51 is a side view of the boot of FIG. 50.
Figure 52:
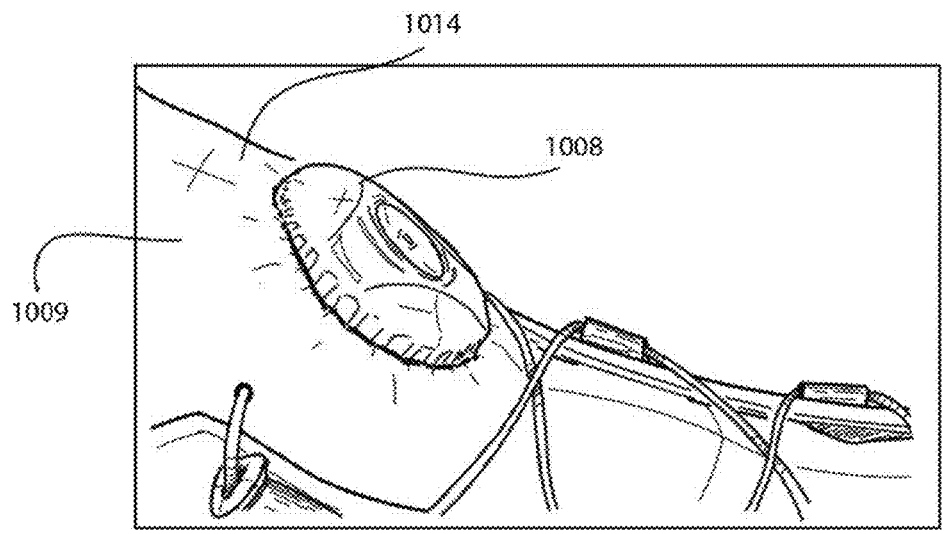
FIG. 52 is a detailed view of the concealing portion and tightening mechanism on the boot of FIG. 50.
Figure 53:
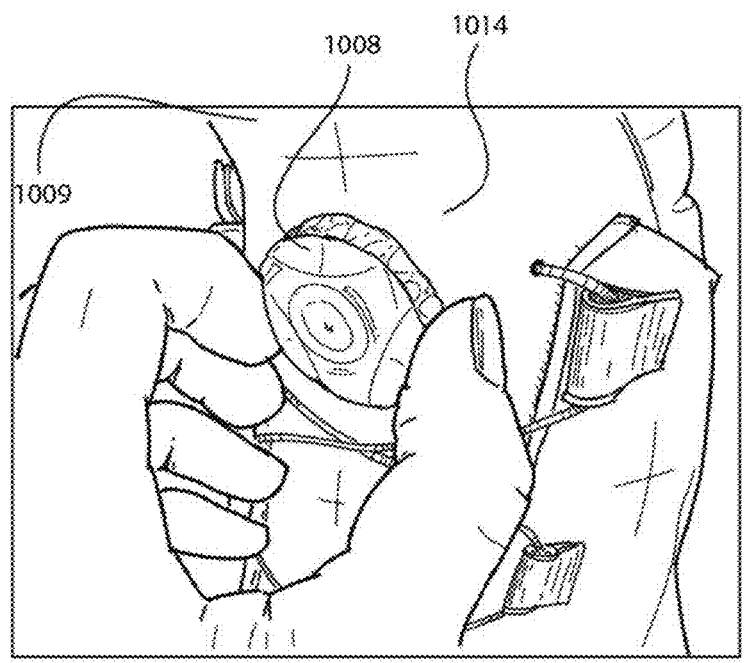
FIG. 53 shows a user actuating the tightening mechanism of the boot of FIG. 50.

Although many embodiments are discussed in connection with a tightening mechanism mounted onto the heel of a shoe or other footwear, many other configurations are possible. FIG. 50 is an isometric view of a boot 1000 having a tightening mechanism 1008 mounted onto the tongue 1009 of the boot 1000 and a concealing portion 1014 at least partially surrounding the tightening mechanism 1008. FIG. 51 is a side view of the boot 1000. FIG. 52 is a detailed view of the concealing portion 1014 and tightening mechanism 1008 on the boot 1000. FIG. 53 shows a user actuating the tightening mechanism 1008 of the boot 1000. Similar configurations are possible for shoes (including high-top shoes and low-top shoes) and other footwear having a tongue. Also, the tightening mechanism 1008 can be mounted onto other portions of the footwear (e.g., on the side thereof).

Figure 54:
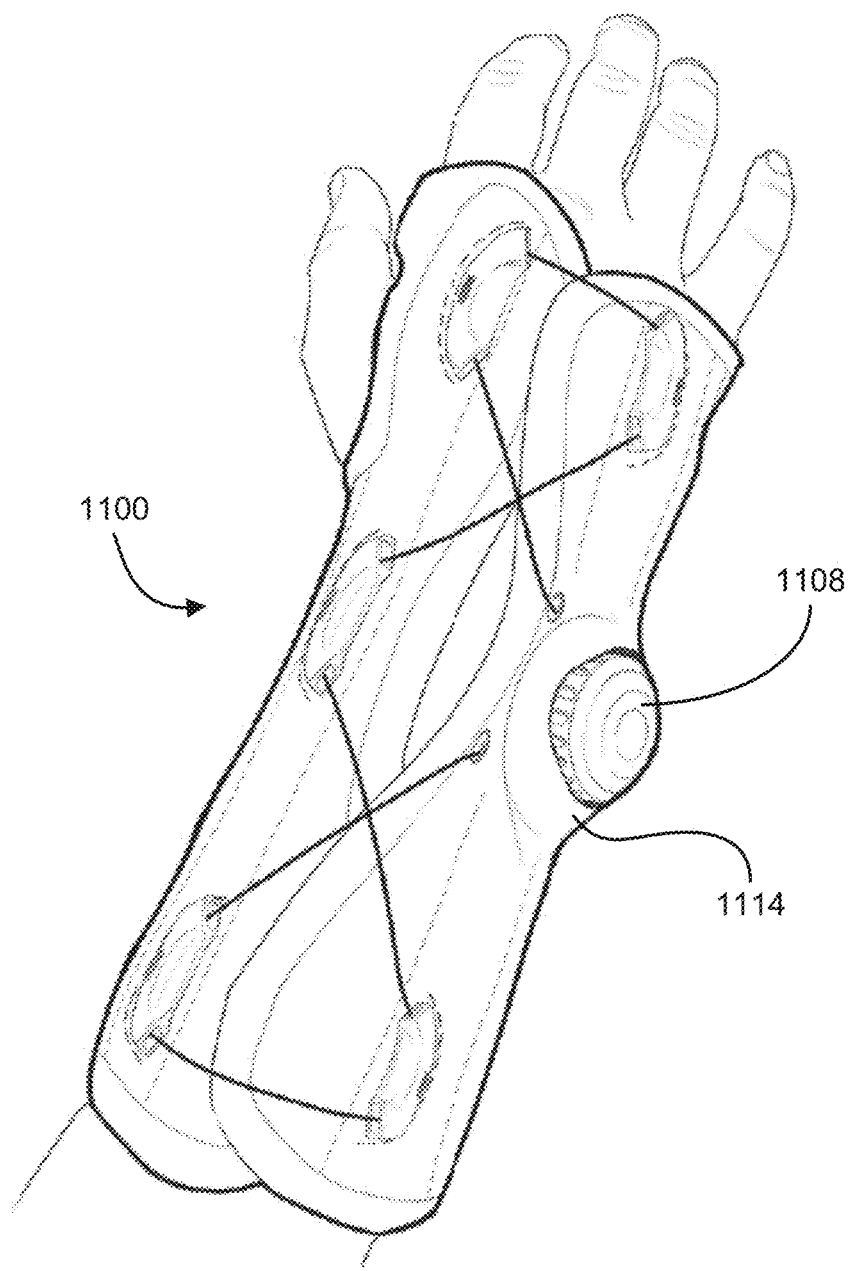
FIG. 54 shows a wrist brace having a tightening mechanism and a concealing portion at least partially surrounding the tightening mechanism.

As mentioned above, the embodiments described herein can be applied to various articles. For example, FIG. 54 shows a wrist brace 1100 having a tightening mechanism 1108 and a concealing portion 1114 at least partially surrounding the tightening mechanism 1108.

Figure 55A:
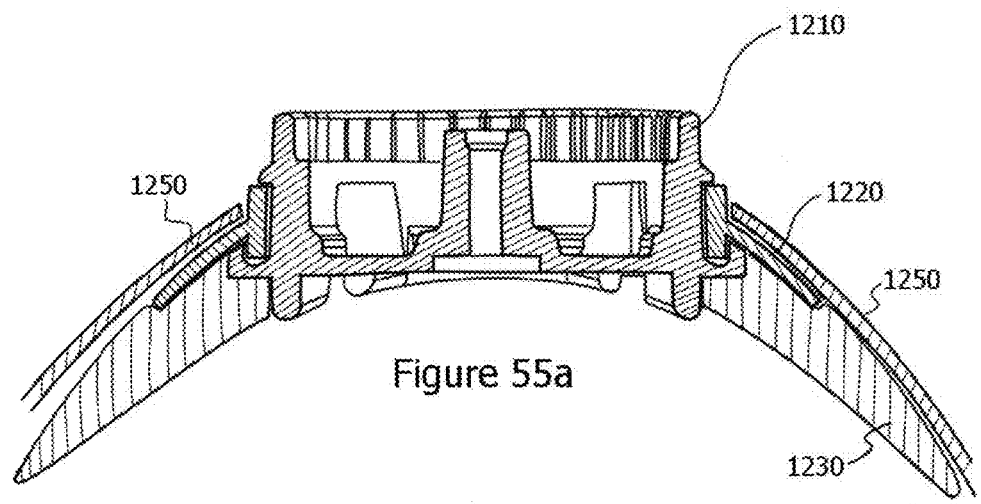
FIGS. 55a-c show a housing of a tightening mechanism being coupled with a foam backing material, which is in turn coupled with a shoe or other apparel.
Figure 55B:
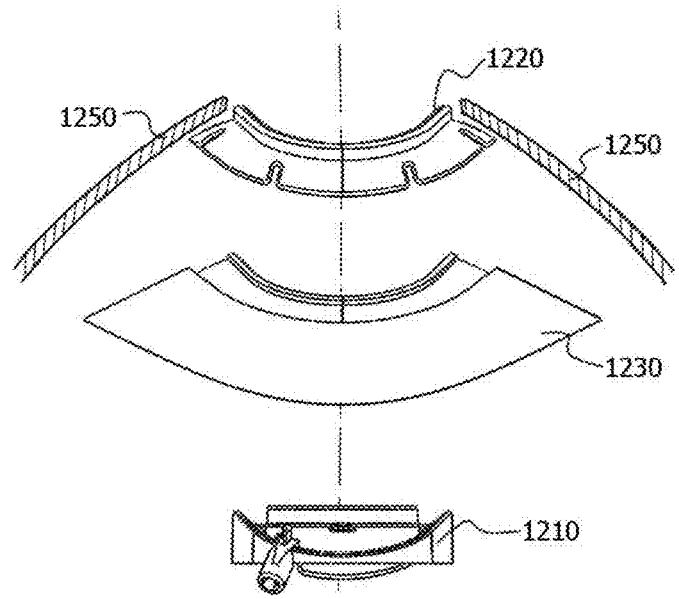
Figure 55C:
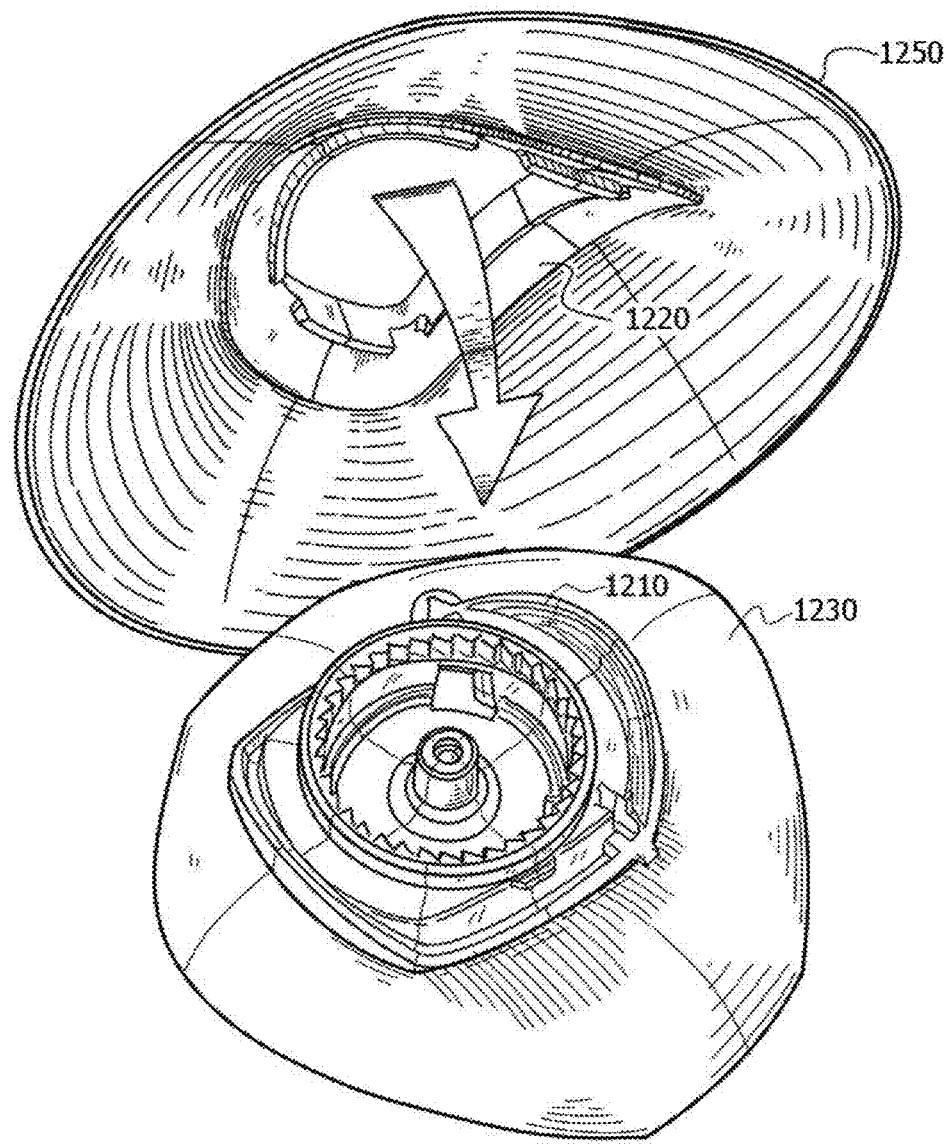

FIGS. 55a-c show a body or housing 1210 of a tightening mechanism being coupled with a compressible material 1230, such as a foam backing material. The backing material could be foam of various densities and of materials such as polyurethane or latex rubber, or a non-foam but compliant material such as a polymer gel. The combination of the three parts shown in FIG. 55b is typically coupled to a shoe upper after assembly but before lasting in various potential sequences of assembly and using various assembly methods. Specifically, the body or housing 1210 (hereinafter housing) may be coupled with a foam backing 1230 and then affixed to the rear of a shoe typically with adhesive or by stitching or by RF welding. While being affixed, tubing (not shown) previously mounted between upper layers, may be plugged at its end into tube ports on the housing 1210 through which lace is routed from the front of the shoe to the housing 1210. Various other embodiments do not use tubing and can allow the tube ports of a housing designed for this purpose to penetrate the shoe surface immediately for the lace coming from the housing 1210 which is then routed externally on the shoe and sometimes with intermediate guiding elements. A relatively rigid mounting component or bayonet 1220 (hereinafter bayonet) is typically joined to a textile or molded overlay known in the shoe industry as a foxing 1250. These components may be joined by stitching, RF welding, insert molding or by other means. This assembly of bayonet 1220 and overlay may then be affixed to the shoe upper and the bayonet 1220 snapped into receiving elements of the housing 1210. Often in shoe manufacturing, a subsequent step would involve "back part molding" where the textile upper is placed inside a foot shaped form known as a lasting form and is then heated, and then in this machine the fabric may be pulled and or pushed around the heel shape to somewhat thermoform the heel shape into the materials. The rigid bayonet 1220 firmly holds the perimeter of the housing 1210 hole in the foxing 1250 so that it is not pulled away leaving unsightly gaps between housing 1210 and foxing. This is a key purpose of the relatively rigid bayonet 1220 to resist deformation during back part molding of the hole in the foxing while it is being formed and also to create a neat edge banding with minimal gaps to the material of the foxing 1250.

In some embodiments, the foam backing 1230 may be molded onto or otherwise coupled with the housing 1210 (e.g. adhered with adhesive or insert molded) so that the foam backing 1230 and housing 1210 appear to be a single or integral piece or component. The foam backing 1230 may be used as a transition component between the tightening mechanism and the shoe to hide any visual defects that may result from attaching the tightening mechanism with the shoe. The foam backing 1230 is relatively compliant material that facilitates in masking or hiding the appearance of marks in the shoe from any underlying components of the tightening mechanism. The foam backing 1230 is able to mask the components by conforming to the specific shape and size of the shoe. For example, when relatively rigid backing materials are used and positioned under the surface of the material of the shoe, the edges of the backing material may be visible or the rigid material may cause the shoe's material to buckle or otherwise deform, which can be visually unappealing. The appearance of underlying components within the shoe is commonly known as ghosting. Ghosting is greatly reduced since foam backing 1230 is compliant and able to adapt and conform to the shape and size the shoe. Specifically, the foam backing 1230 may be able to adapt to the shape and size of the heel counter.

The compliant foam backing 1230 is also capable of adapting to various different shapes and sizes of shoes. This adaptability of the foam backing results in a reduction in the number of backing components that must be manufactured, thereby reducing part count. Foam backing 1230 is adaptable to the various shaped and sized shoes by being insertable and compressible between layers of the shoe. Further, the compliance of foam backing 1230 allows the foam backing 1230 to be easily wrapped around the heel counter or another component of the shoe regardless of the shoes contour, size, or shape. The foam backing 1230 may be matched to an existing profile of a shoe. For example, the foam piece may be formed to match surrounding surfaces of the article of application (e.g., shoe) so as to provide a seamless visually appealing look.

In some embodiments, the foam backing 1230 may have trimmable parts that allow the shape and/or size of the foam backing 1230 to be adjusted to fit the shape and size of the shoe, such as for example, to particularly adapt to smaller shoe sizes with associated shorter distances from sole to shoe collar. In one embodiment, foam backing 1230 may include a plurality of material layers coupled together in a stacked arrangement, similar to the layers of an onion. Each of the layers may be stripped or peeled away so as to reduce the overall thickness of the foam backing 1230 as desired. In another embodiment, the foam backing 1230 may have perforated portions or regions that allow sections of the foam backing 1230 to be cut or torn away as desired to reduce the size of the foam backing. Similarly, the durometer of the foam may be varied to provide a desired compressibility of the foam material. In some embodiments, the durometer of foam backing 1230 may vary between about 10 and 25 Shore A. By adjusting the durometer of the foam, removing sections, and/or stripping or peeling away various layers of the foam backing 1230, the foam backing 1230 may be adjusted to conform to a specifically designed shoe. In some embodiments, the foam backing 1230 may include a thermoset material to resist permanent deformation when heated and pressured during back part molding.

In another embodiment, a shim may be positioned under the foam backing 1230 to help the foam backing 1230 conform to and/or adapt to different sized and shaped shoes. For example, when a relatively large thickness of foam backing 1230 is needed or otherwise desired, such as when foam backing 1230 is coupled with a large shoe, a shim may be placed under foam backing 1230 to increase the overall thickness of foam backing 1230. The shim may comprise any shape or size as desired and may be made of a variety of materials, such as urethane, rubber, an elastomer, and the like. In another embodiment, the foam backing 1230 may include multiple pieces of foam or another material and/or may be unattached to bayonet 1220.

Bayonet 1220 includes a flange positioned partially or fully around the perimeter of bayonet 1220. The flange allows the bayonet 1220 to be sewn, adhered, or otherwise coupled with the shoe or other apparel. Housing 1210 couples with bayonet 1220 in a relatively rigid manner. In some embodiment, housing 1210 may be removably coupled with bayonet 1220 so that housing 1210 may be removed for replacement, repair, and the like. In one embodiment, housing 1210 and bayonet 1220 may be coupled together by snapping together mating portions of the housing 1210 and bayonet 1220. In another embodiment, bayonet 1220 may include bosses that snap or otherwise couple with apertures of the housing 1210, or vice versa. Cleats may also be used to couple housing 1210 with bayonet 1220; or the bayonet 1220 may be welded (e.g. heat, RF, ultrasonic, and the like), adhered, or coupled with housing 1210 using any method known in the art. Coupling or interlocking of the housing 1210 with bayonet 1220 using any fastening means described herein (e.g., bosses, cleats, mating components, welding, adhesive bonding, and the like), may facilitate in transferring rotational force from the housing 1210 to the bayonet 1220 as the tightening mechanism is operated. Bayonet 1220 may likewise transfer such force to the shoe or apparel. In this manner, the rotational force is not transferred to foam backing 1230, which rotational force may cause foam backing 1230 to deform (e.g. become oblong and the like) and/or become visible through a top layer of the shoe or apparel.

Figure 56A:
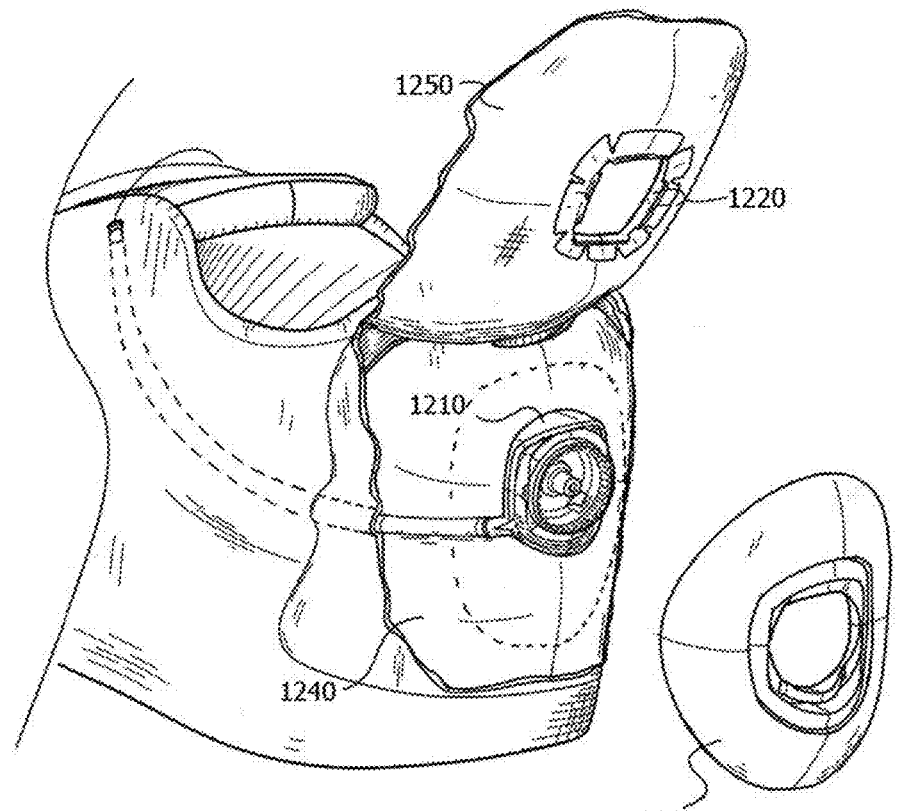
FIGS. 56a-b show a housing of a tightening mechanism being an integral component of a heel counter of a shoe.
Figure 56B:
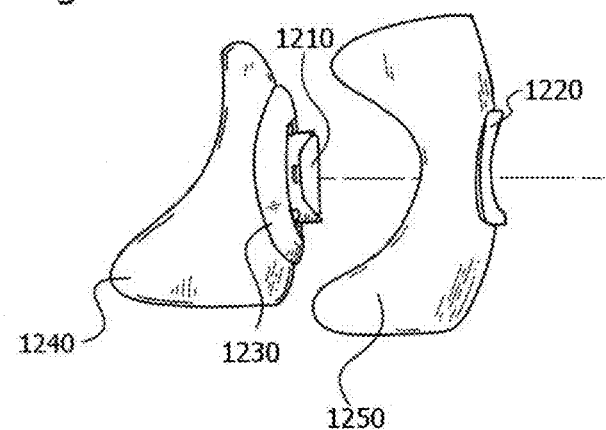
Figure 57A:
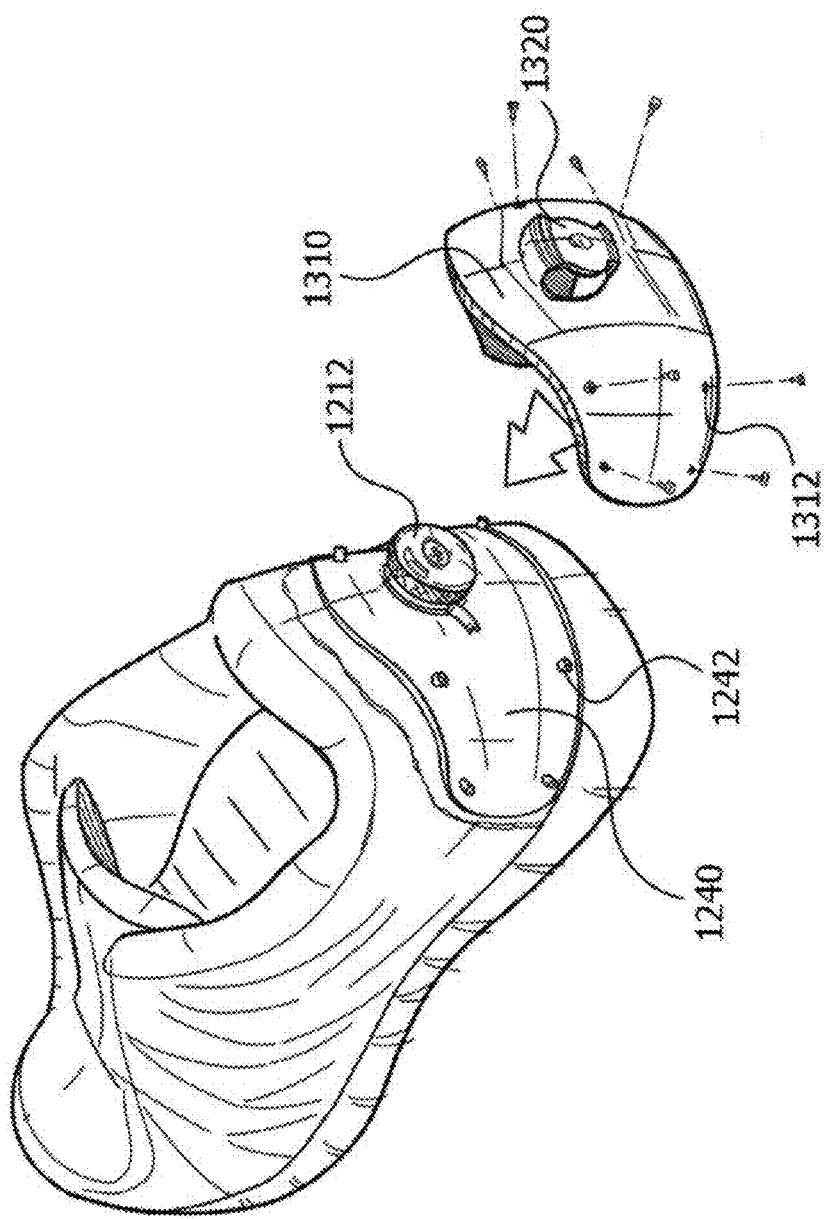
FIGS. 57a-d show a cover plate that is positionable over a housing and knob of a tightening mechanism.
Figure 57B:
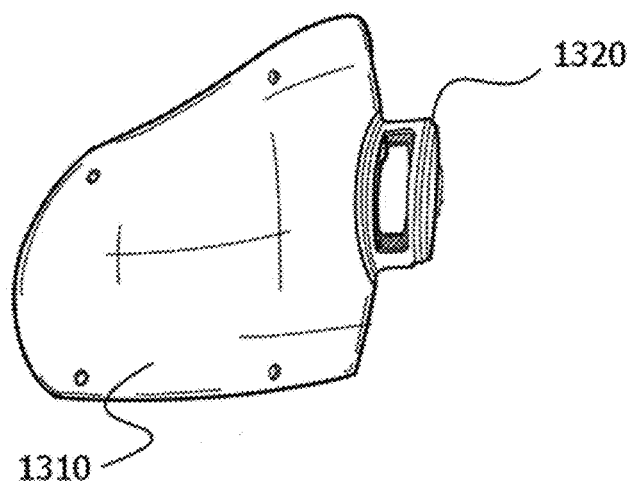
Figure 57C:
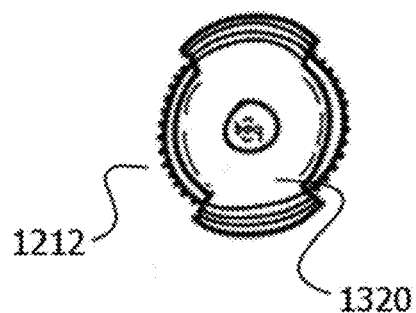
Figure 57D:
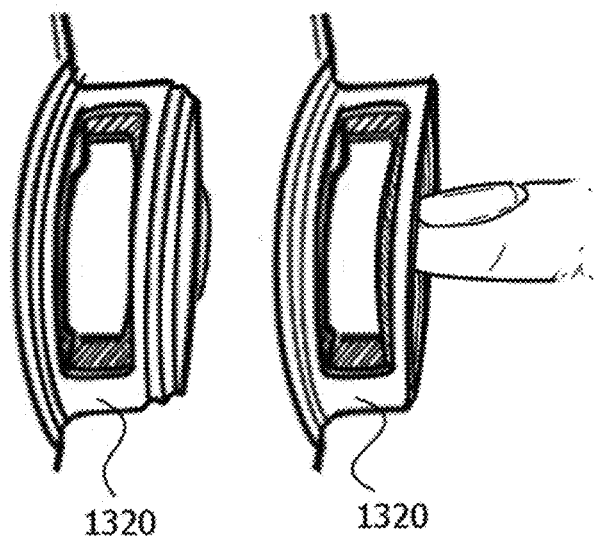

FIGS. 56*a-b* show the housing 1210 of a tightening mechanism being an integral component of a heel counter 1240 of a shoe. FIGS. 56*a-b* are similar to FIGS. 55*a-c* except that housing 1210 is molded onto the heel counter 1240 so that heel counter 1240 and housing 1210 are essentially a single component or piece. The single piece heel counter 1240 and housing 1210 may be installed in the shoe as a single unit to eliminate the risk of deformation during construction thereof. Various sizes of these may be molded. In another approach the wings of the heel counter are essentially flat and may be post trimmed via steel rule dies or other method and then pre-thermoformed to an appropriate curvature for the size of shoe intended. In some embodiments, the bayonet 1220 and foam backing 1230 may be fit over and coupled with housing 1210 as described with respect to FIGS. 55*a-c*. The material of the shoe 1250, such as padding, foxing, and the like, may be positioned over the heel counter 1240 and housing 1210 to cover these components and/or to provide padding for the shoe. In this manner housing 1210 may be coupled with the shoe and hidden from view. Often this heel counter/housing combination would be sandwiched between shoe inner liner materials and the outer quarters of the shoe.

Referring now to FIGS. 57*a-d*, in some embodiments, a cover plate 1310 may be positioned over the housing 1210 of the tightening mechanism. The cover plate 1310 may include a dial cover 1320 that is configured to fit over the knob 1212 of the tightening mechanism so as to cover and hide the knob 1212. In some embodiments, opposing sides of the dial cover 1320 may be opened so that the sides of knob 1212 are exposed to allow a user to operate the knob 1212 to wind lace about a spool (not shown) of the tightening mechanism as described herein. In some embodiments, the cover plate 1310 may be fit over a foam backing 1230 and bayonet 1220 that are coupled with the housing 1210 as described herein. In other embodiment, the foam backing 1230 and/or bayonet 1220 may not be used and the cover plate 1310 may be fit directly over the knob 1212.

Heel counter 1240 may include bosses 1242 that allow cover plate 1310 to be coupled with heel counter 1240, such as by inserting screws through apertures 1312 of cover plate 1310 that correspond with bosses 1242. In other embodiments, cover plate 1310 may be sewn, adhesively bonded, welded (e.g. heat, ultrasonic, and the like), and the like to heel counter 1240.

The dial cover 1320 may be a relatively resilient or compliant component that allows the cover plate 1320 to be laterally adjusted relative to cover plate 1310. Stated differently, the dial cover 1320 may be laterally repositioned relative to cover plate 1310 by stretching dial cover 1320 laterally outward. The adjustability of dial cover 1320 with respect to cover plate 1310 may act on the tightening knob of the reel to allow the tightening mechanism (e.g. knob 1220) to be pulled axially outward relative to the shoe so as to release a tension on the lace and unwind the lace from a spool of the tightening mechanism as described herein. In this manner, the knob 1220 may be rotated to wind the lace about a spool of the tightening mechanism and subsequently pulled axially outward to unwind the lace from the lace as described herein. In some embodiments, the dial cover 1320 may apply an axial pressure to knob 1220 when the knob 1220 is pulled axially outward so that when a user releases knob 1220, the knob is biased or forced axially inward and able to be rotated to wind the lace about the spool of the tightening mechanism. In another embodiment, knob 1220 may be rotated in a first direction (e.g., clockwise) to wind lace about the spool and may be rotated in a second direction (e.g., counterclockwise) to unwind lace therefrom. In a specific embodiment, rotation of the spool in a second direction by a defined amount (e.g., between 15 and 90 degrees), may release the tension on the lace and allow the lace to be quickly unwound from the spool.

In some embodiments, the dial cover 1320 may have axial clearance for knob 1212 such that the knob may be grasped through side openings in 1312 such that the knob may stay in the axial outward and released position. Then the compliant and overlaid dial cover 1320 may function as a button so that pressing a top surface of the dial cover 1320 axially inward causes the dial cover 1322 to displace axially between a first position, in which the dial cover 1320 is adjacent the outer surface of the shoe, and a second position, in which dial cover 1320 is positioned axially offset from the shoe. Pressing the dial cover 1320 in this manner may also cause the knob 1212 to axially displace between the first and second position in which the lace may either be wound around the tightening mechanisms spool or unwound therefrom as described herein.

In some embodiments, the cover plate 1310 may include one or more channels (not shown) positioned on an interior surface thereof that define lace paths for the lace of the tightening system. The channels on the interior surface of cover plate 1310 may replace tubing (not shown) which is commonly used to channel and run lace between various regions or areas of the shoe, such as from the heel to the tongue of the shoe. In another embodiment, tubing (not shown) may be integrated with cover plate 1310 such as being coupled (e.g. adhesively bonded, snapped and the like) with an interior or exterior surface of cover plate 1310. Cover plate 1310 may be made of a durometer in the range of 20 to 50 Shore A to allow it to conform to various shoe shapes and may also include one or more relief cuts or slots that allow the cover plate 1310 to be flexed so as to accommodate and conform to various shaped and sized shoes. Cover plate 1310 may be a relatively hard plastic material, or a relatively soft, resilient, and flexible material.

Figure 58:
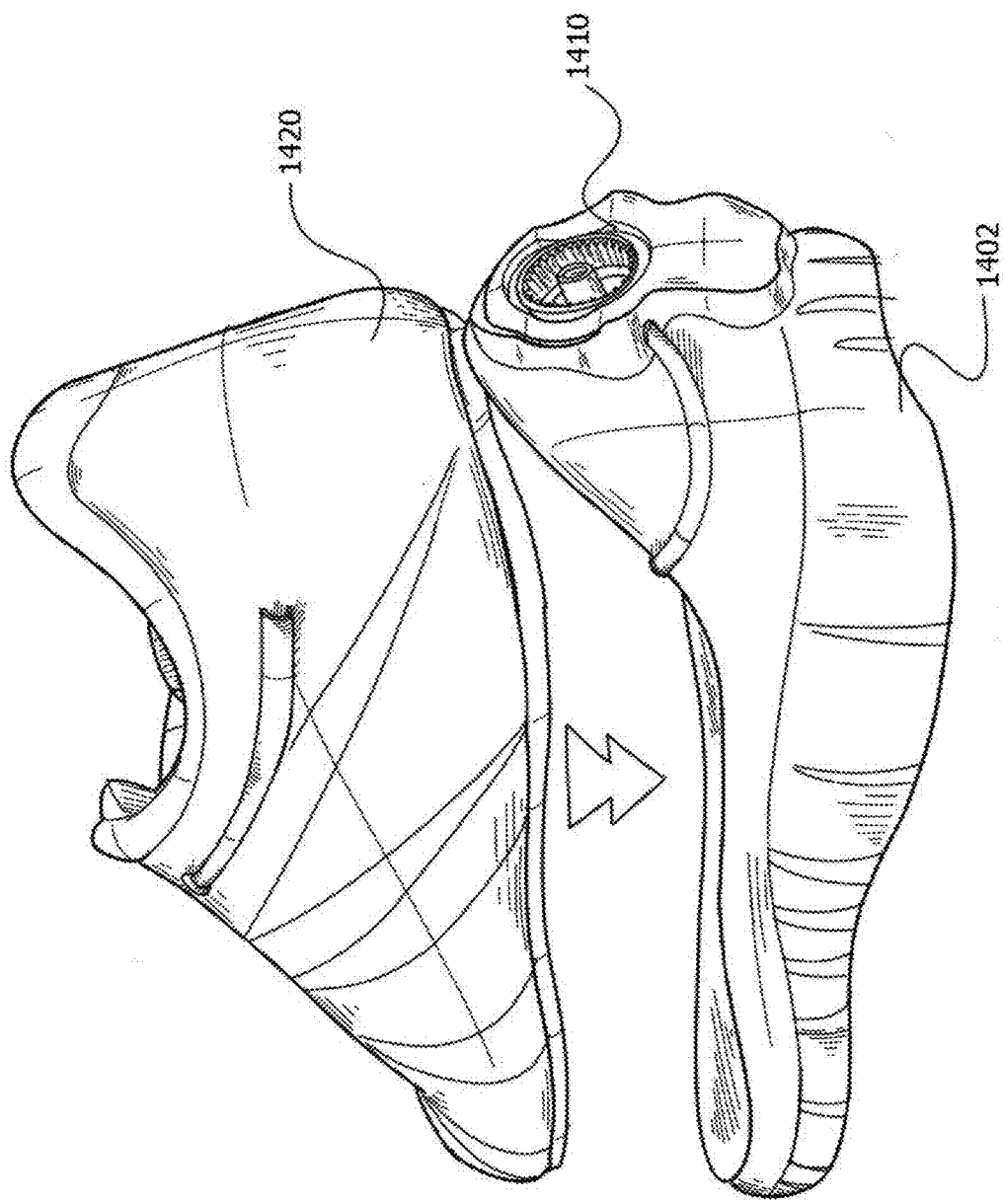
FIG. 58 shows a housing of a tightening mechanism integrally formed with an outsole of a shoe.

Referring now to FIG. 58, illustrated is another embodiment of coupling a housing 1410 with a shoe. Specifically, the housing 1410 may be integrally formed with an outsole 1402 that is subsequently coupled with the upper material 1420 of the shoe. In one embodiment, the housing 1410 may be insert molded with the outsole 1402. In another embodiment, the housing may be sewn, adhesively bonded, welded, and the like with outsole 1402. Since housing 1410 is integrally formed with outsole 1402, the use of other components to couple the housing 1410 with the shoe (e.g. a bayonet and the like) may not be needed. Likewise, the use of a foam backing may not be needed since ghosting and/or other issues may not be as prevalent. In another embodiment, the housing 1410 may be coupled with the midsole of the shoe that is coupled with the upper material 1420 and/or outsole 1402. In some cases, tubing for routing lace may be plugged into corresponding housing tube ports. In other cases, the lace may be routed through channels and then along the outside surface of the shoe toward the shoe tongue. In other embodiments, the housing 1410 may be stitched, bonded, glued to the upper and an outsole 1402 may be direct injected to surround the housing 1410.

Figure 59A:
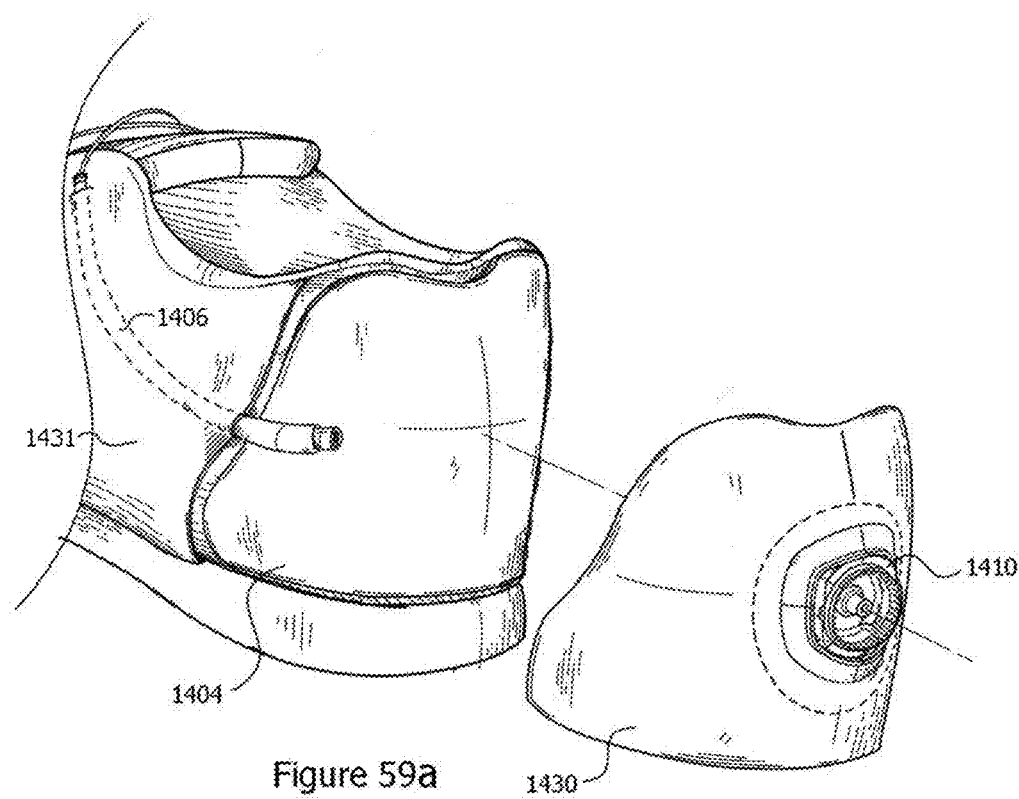
FIGS. 59a-b show a housing of a tightening mechanism integrally formed with an outer material that is coupled with a shoe.
Figure 59B:
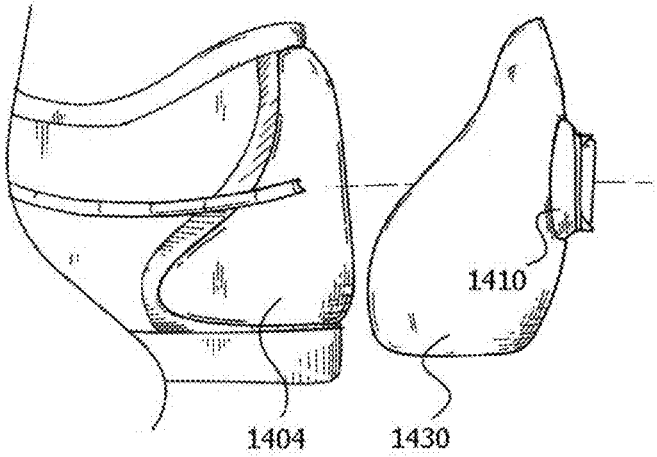

Referring to FIGS. 59*a-b*, illustrated is another embodiment of coupling the housing 1410 to a shoe. Specifically, the housing 1410 may be integrally formed with an outer material 1430 that is subsequently coupled with this shoe, such as heel counter 1404. Rather than have the quarters of the shoe sides 1431 overlay the heel counter, in this instance the sides are cut away and do not overlap in order to make a lighter and thinner heel form. The housing 1410 may be pre-attached to the foxing or outer material 1430 via sewing, adhesive bonding, molding, and the like. The foam backing may be sandwiched between the housing 1410 and outer material 1430 during this process. Attaching the housing 1410 to the outer material 1430 in this manner may eliminate the need for one or more other components to be used, such as a bayonet, and the like. Attaching the housing 1410 to the outer material 1430 also allows the housing and tightening mechanism to easily conform to the shape and size of the shoe. The outer material 1430 also covers one or more other components of the tightening mechanism, such as tubing 1406 so that these components are hidden from view of the user. The outer material 1430 may include one or more holes (not shown) and/or channels through which the lace is inserted so that the lace may pass from tubing 1406, which is positioned on the under surface of outer material 1430, to the tightening mechanism, which is positioned on the outer surface of outer material 1430.

Figure 60A:
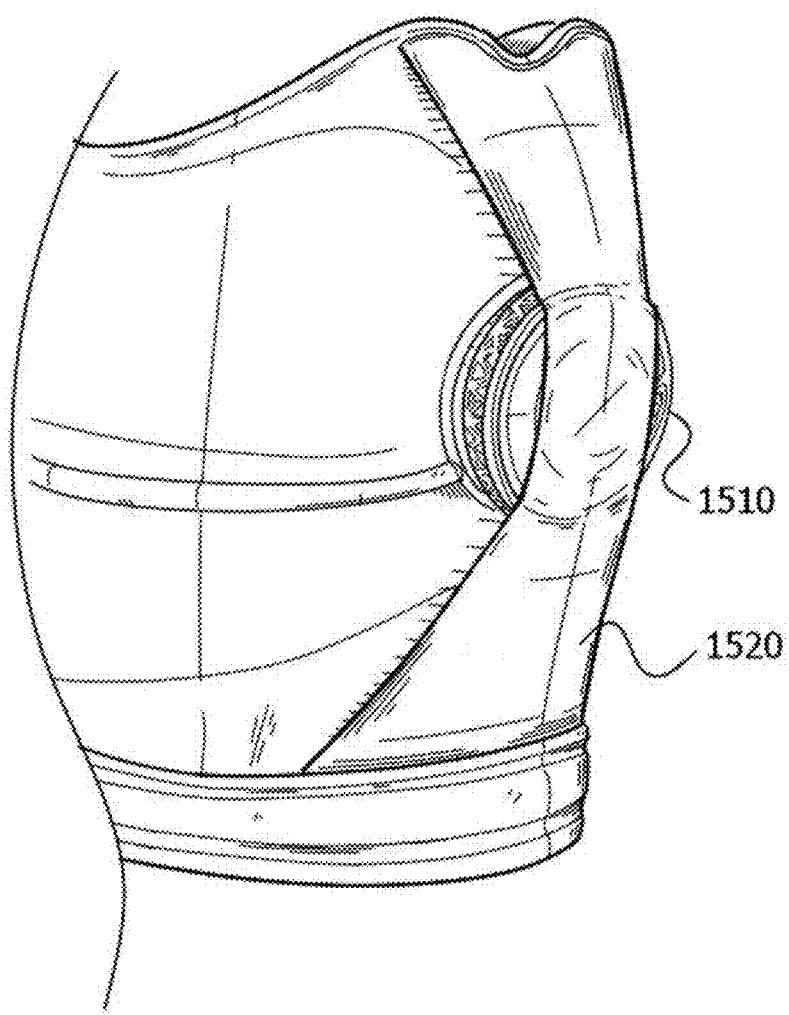
FIGS. 60a-c show a flexible strip of material coupled with a shoe so as to be positioned over a tightening mechanism to hide a portion of the tightening mechanism from view of a user.
Figure 60B:
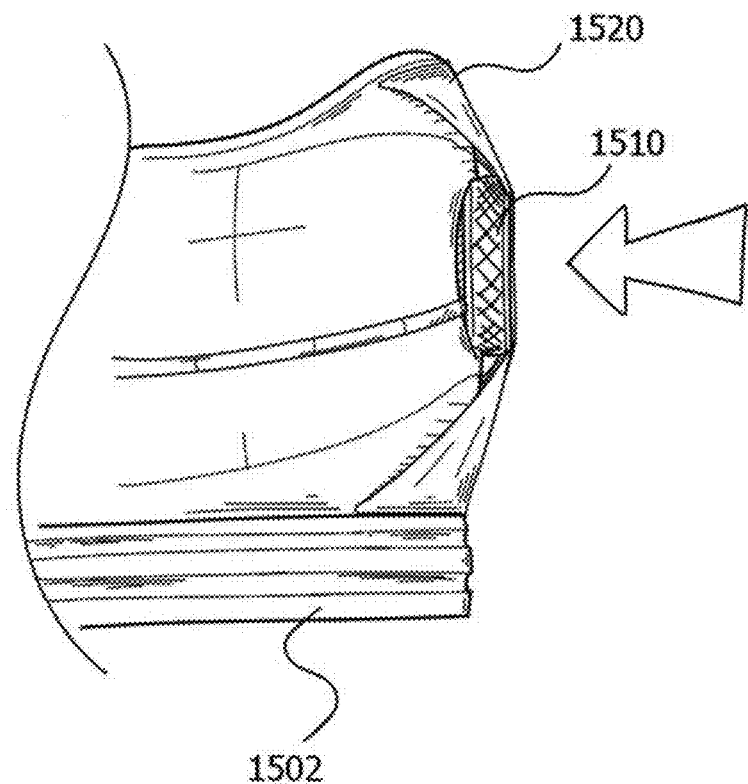
Figure 60C:
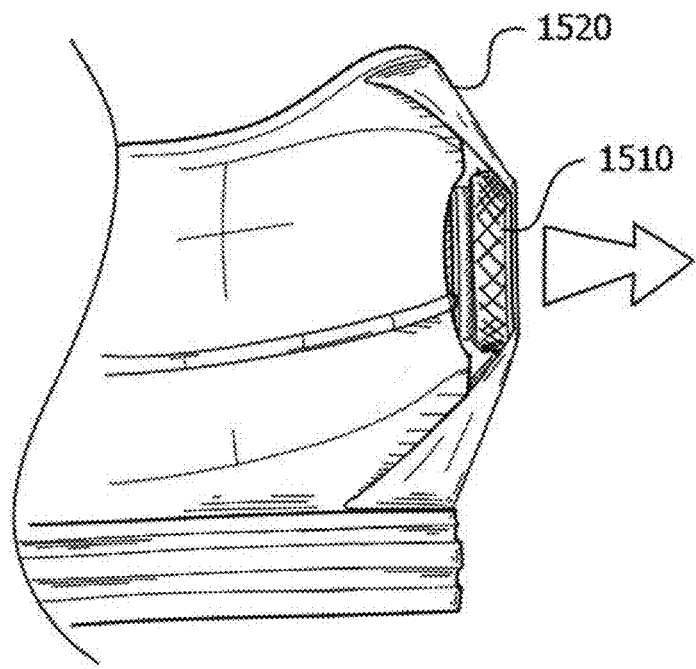

Referring now to FIGS. 60*a-c*, illustrated is another embodiment of coupling a tightening mechanism 1510 with a shoe 1502. Specifically, a flexible strip of material 1520 may be coupled over the tightening mechanism 1510 to hide a portion of the tightening mechanism 1510 from view of a user and/or for various other functional reasons, such as to define an outer contour of a heel of the shoe or to provide axial pressure to the tightening mechanism 1510. In one embodiment, the strip of flexible material 1520 may be positioned over tightening mechanism 1510 so that opposing sides of the tightening mechanism 1510 are exposed and able to be grasped and rotated by a user. In some embodiments, the strip of flexible material 1520 may include a resilient material that allows the tightening mechanism 1510 to be pulled axially outward so that lace may be unwound from a spool of the tightening mechanism. The flexible material strip 1520 may apply an axial force to tightening mechanism 1510 to cause the tightening mechanism 1510 to return to a position axially inward relative to the shoe after lace is unwound from the spool of the tightening mechanism. The flexible material strip 1520 may provide a relatively visual pleasing appearance to the shoe as well as providing any of the functional aspects described herein.

Figure 61:
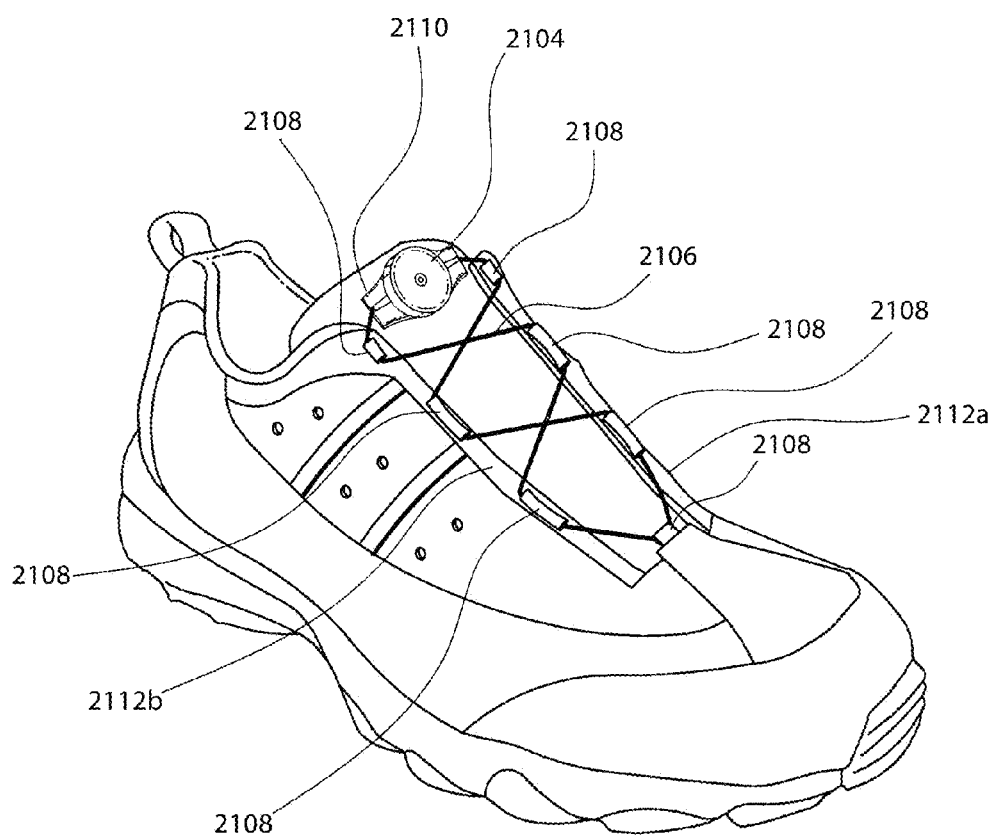
FIG. 61 is a perspective view of an embodiment of a lacing system in use with a sport shoe.

FIG. 61 is a perspective view of a lacing system 2100 used for tightening a sport shoe 2102. The sport shoe can be a running shoe, a basketball shoe, and ice skating boot, or snow boarding boot, or any other suitable footwear that can be tightened around a wearer's foot. The lacing system 2100 can be used to close or tighten various other articles, such as, for example, a belt, a hat, a glove, snow board bindings, a medical brace, or a bag. The lacing system can include a reel 2104, a lace 2106, and one or more lace guides 2108. In the illustrated embodiment, the reel 2104 can be attached to the tongue 2110 of the shoe. Various other configurations are possible. For example, the reel 2104 can be attached to a side of the sport shoe 2102, which can be advantageous for shoes in which the shoe sides 2112*a-b* are designed to be drawn closely together when tightened leaving only a small portion of the tongue 2110 exposed. The reel 2104 can also be attached to the back of the shoe 6102, and a portion of the lace 2106 can pass through the shoe 2102 on either side of the wearer's ankle such that the lace 2106 can be engaged with the reel 2104 when back-mounted.

Figure 62:
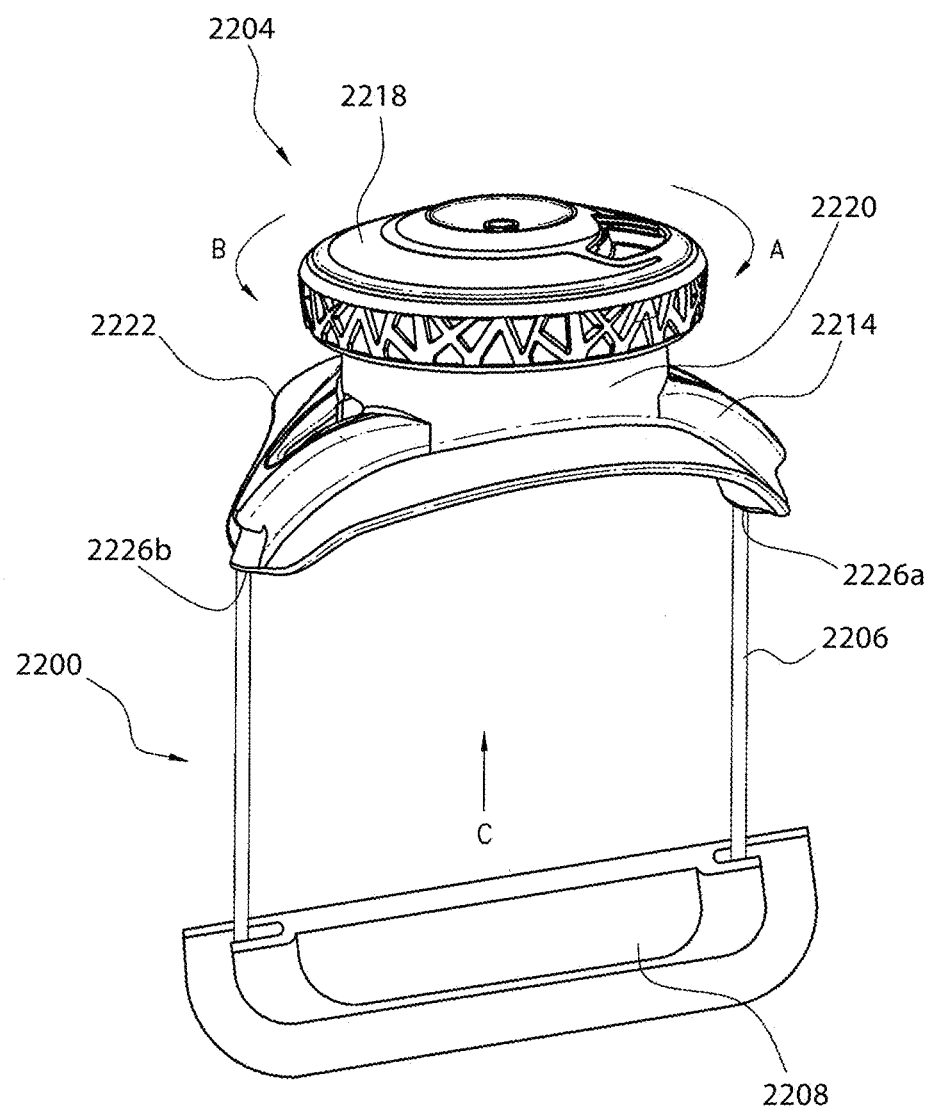
FIG. 62 is a perspective view of an embodiment of a lacing system.
Figure 63:
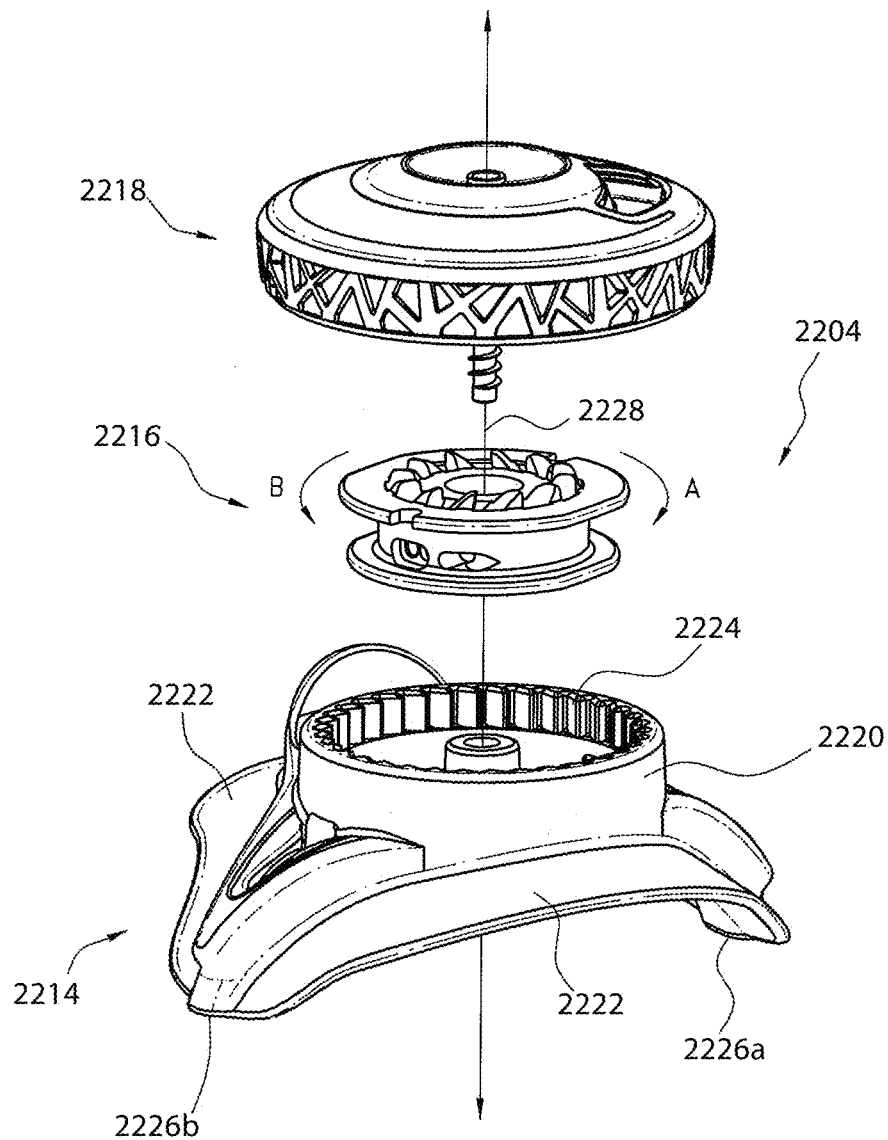
FIG. 63 is an exploded perspective view of the reel from the lacing system of FIG. 62.
Figure 64:
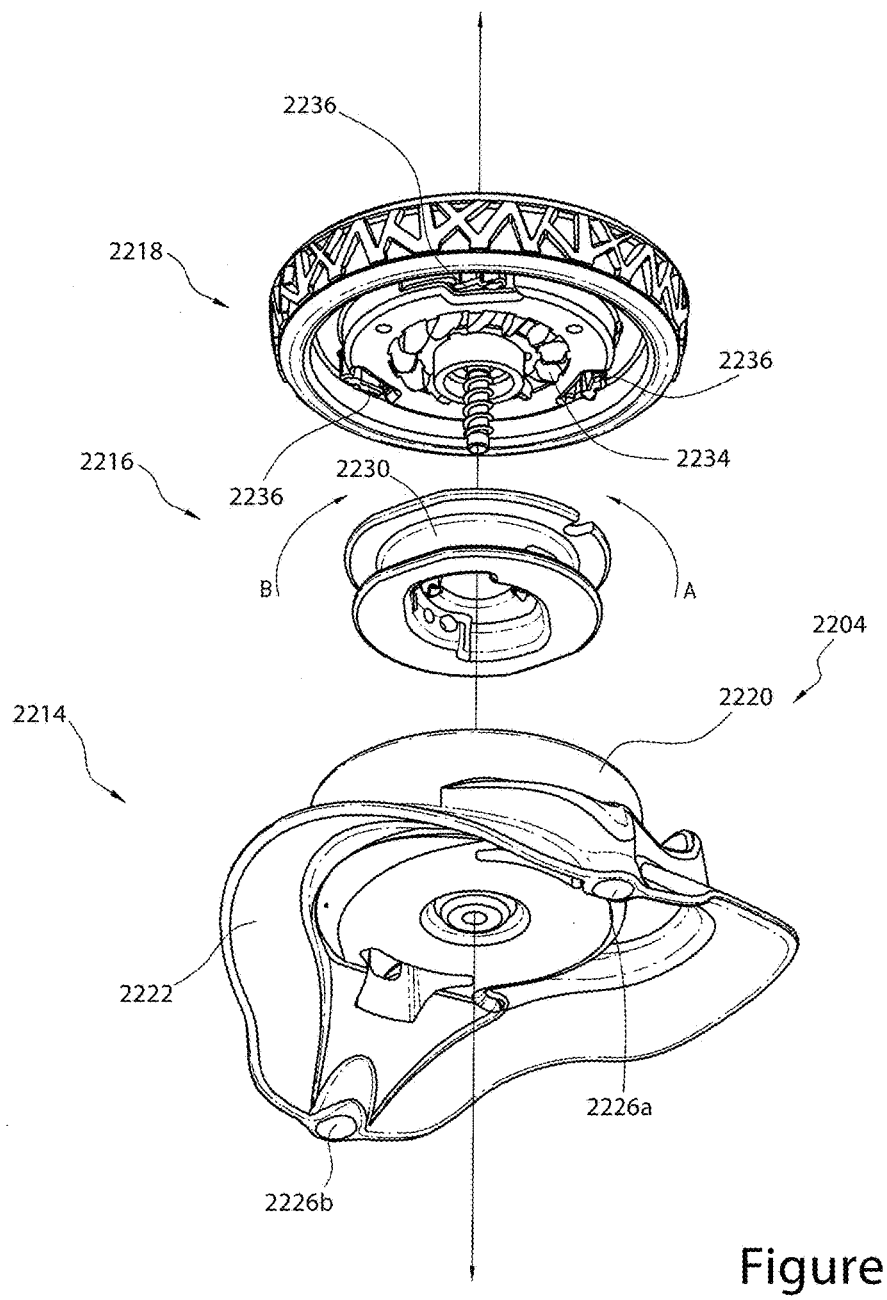
FIG. 64 is another exploded perspective view of the reel of FIG. 63.

FIG. 62 is a perspective view of a lacing system 2200 that can be similar to the lacing system 2100, or any other lacing system described herein. The lacing system can include a reel 2204 which can be similar to the reel 2104, or any other reel described herein. FIG. 63 is an exploded perspective view of the reel 2204. FIG. 64 is another exploded perspective view of the reel 2204.

With reference to FIGS. 62 to 64, the reel 2204 can include a base member 2214, a spool member 2216, and a knob member 2218. The base member can include a housing 2220 and a mounting flange 2222. The housing 2220 can include a plurality of housing teeth 2224, which can extend radially inwardly. The housing 2220 can include lace holes 2226*a-b* that allow the lace 2206 to enter the housing 2220.

The spool member 2216 can be disposed within the housing 2220 such that the spool member 2216 is rotatable about an axis 2228 with respect to the housing 2220. The lace 2206 can be secured to the spool member 2216 such that when the spool member 2216 rotates in a tightening direction (shown by arrow A) the lace 2206 is drawn into the housing 2220 and is wound around the channel 2230 formed in the spool member 2216, and when the spool member 2216 rotates in a loosening direction (shown by arrow B) the lace 2206 unwinds from the channel 2230 of the spool member 2216 and exits the housing 2220 via the lace holes 2226*a-b*. The spool member 2216 can also include spool teeth 2232 formed thereon. It will be understood that the embodiments disclosed herein can be modified such that rotation in the direction shown by arrow B will tighten the lacing system and such that rotation in the direction shown by arrow A will loosen the lacing system.

The knob member 2218 can be attached to the housing 2220 such that the knob member 2218 can rotate about the axis 2228 with respect to the housing 2220. The knob member 2218 can include knob teeth 2234 that can be configured to mate with the spool teeth 2232 to couple the knob member 2218 to the spool member 2216 such that rotation of the knob member 2218 in the tightening direction causes the spool member 2216 to also rotate in the tightening direction. In some embodiments, the rotation of the knob member 2218 in the loosening direction can also cause the spool member 2216 to rotate in the loosening direction. The knob member 2218 can also include one or more pawls 2236 which can be biased radially outwardly so as to mate with the housing teeth 2224. The pawls 2236 and housing teeth 2224 can be configured so that the housing teeth 2224 can displace the pawls 2236 radially inwardly when the knob member 2218 is rotated in the tightening direction, thereby allowing the knob member 2218 to rotate in the tightening direction. The pawls 2236 and the housing teeth 2224 can also be configured so that they engage one another when force is applied to twist the knob member 2218 in the loosening direction, thereby preventing the knob member 2218 from rotating in the loosening direction.

Thus, the reel 2204 can provide a one-way tightening system configured to allow the user to rotate the knob member 2218 in the tightening direction, which causes the spool member 2216 to rotate in the tightening direction, which in turn causes the lace 2206 to be drawn into the housing 2220 via the lace holes 2226*a-b*. As the lace 2206 is drawn into the housing 2220 the lacing system 2200 can tighten, causing the lace guide 2208 to be drawn in the direction toward the reel 2204 (shown by arrow C in FIG. 62). Although the lacing system 2200 is shown with a single lace guide 2208, any other suitable number of lace guides can be used.

Figure 65:
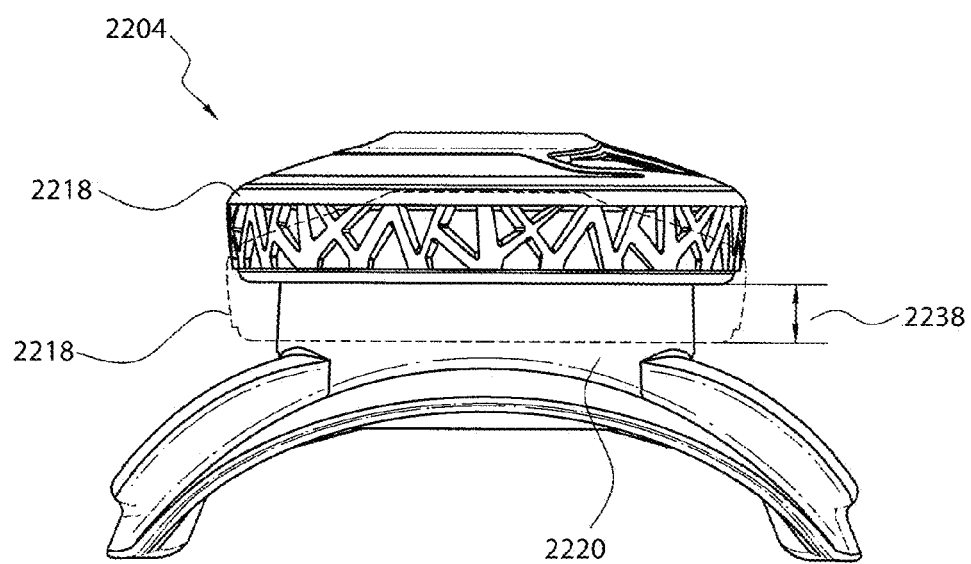
FIG. 65 is a side view of the reel of FIG. 63 with the knob member shown in a disengaged position drawn in normal lines, and with the knob member in an engaged position shown drawn in dotted lines.

In some embodiments, the knob member 2218 can be axially movable along the axis 2228 between a first or engaged position and a second or disengaged position. FIG. 65 is a side view of the reel 2204 showing the knob member 2218 in the disengaged position drawn in normal lines and showing the knob member 2218 in the engaged position outlined in dotted lines. When in the engaged position, the spool teeth 2232 can engage with the knob teeth 2234 to couple the knob member 2218 to the spool member 2216 as described above. Also, when in the engaged position, the pawls 2236 can engage with the housing teeth 2224 to allow the knob member 2218 to rotate in the tightening direction while preventing the knob member 2218 from rotating in the loosening direction, as discussed above.

When in the disengaged position, the knob member 2218 can be positioned axially further away from the base member 2214 by a distance 2238 that is sufficient to cause the knob teeth 2234 to lift away from and disengage the spool teeth 2232 so that the spool member 2216 is decoupled from the knob member 2218 and the spool member 2216 is free to rotate separately from the knob member 2218. Thus, the lace 2206 can be withdrawn from the housing 2220 as the spool member 2216 rotates in the loosening direction causing the lacing system 2200 to loosen. When in the disengaged position, the pawls 2236 of the knob member 2218 can be lifted away from the housing teeth 2224 such that they disengage and the knob member 2218 is free to rotate in the both the tightening and loosening direction without restriction. In some embodiments, when the knob member 2218 is transitioned to the disengaged position, the knob teeth 2234 disengage from the spool teeth 2232 and the pawls 2236 also disengage from the housing teeth 2224. In some embodiments, when the knob member 2218 is transitioned to the disengaged position, the knob teeth 2234 disengage from the spool teeth 2232 while the pawls 2236 continue to engage the housing teeth 2224. In some embodiments, when the knob member 2218 is transitioned to the disengaged position, the knob teeth 2234 continue to engage the spool teeth 2232 but the pawls 2236 disengage from the housing teeth 2224.

The distance 2238 between the engaged and disengaged positions of the knob member 2318 can be at least about 1 mm and/or no more than about 3 mm, and can be about 2.25 mm in some embodiments, although distances outside these ranges can also be used. In some embodiments, the distance 2238 can be approximately the same, or slightly greater than, the height of the spool teeth 2232, the height of the knob teeth 2234, the height of the housing teeth 2224, and/or the height of the pawls 2236.

In some embodiments, because the pawls 2236 engage the housing teeth 2224 in a radial direction while the knob member 2218 is movable between the engaged and disengaged positioned in the axial direction, the reel 2204 can be resistant to accidental disengagement. When the knob member is in the engaged position, and a force is applied to attempt to twist the knob member 2218 in the loosening direction, or lace is pulled tightly causing the spool member 2218 to attempt to twist in the loosening direction, the force is applied to the pawls 2236 as they engage the housing teeth 2224. Because the pawls 2236 are configured to be displaced radially, not axially, substantially none of the force applied to the pawls 2236 is transferred in the axial direction. Therefore, the reel 2204 can resist higher tightening pressure than some reels in which knob pawls engage housing teeth in the axial direction.

Figure 66:
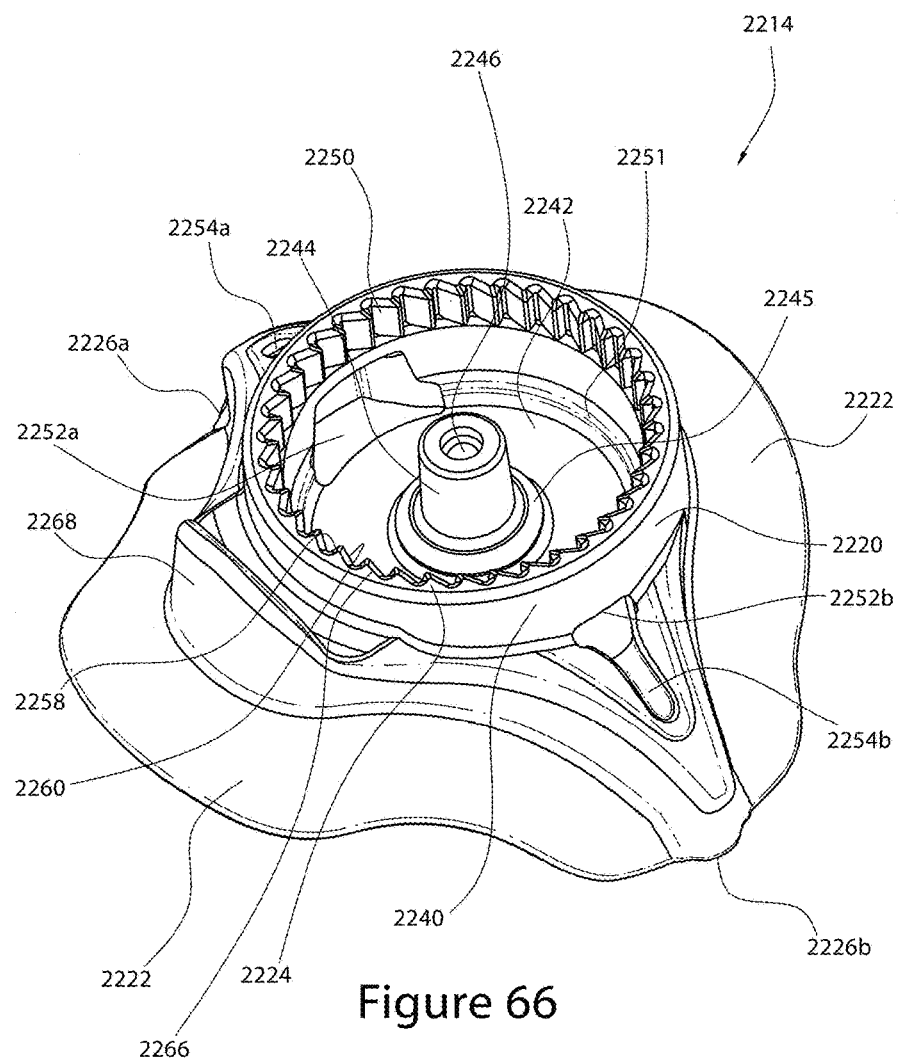
FIG. 66 is a perspective view of the base member from the reel of FIG. 63.
Figure 67:
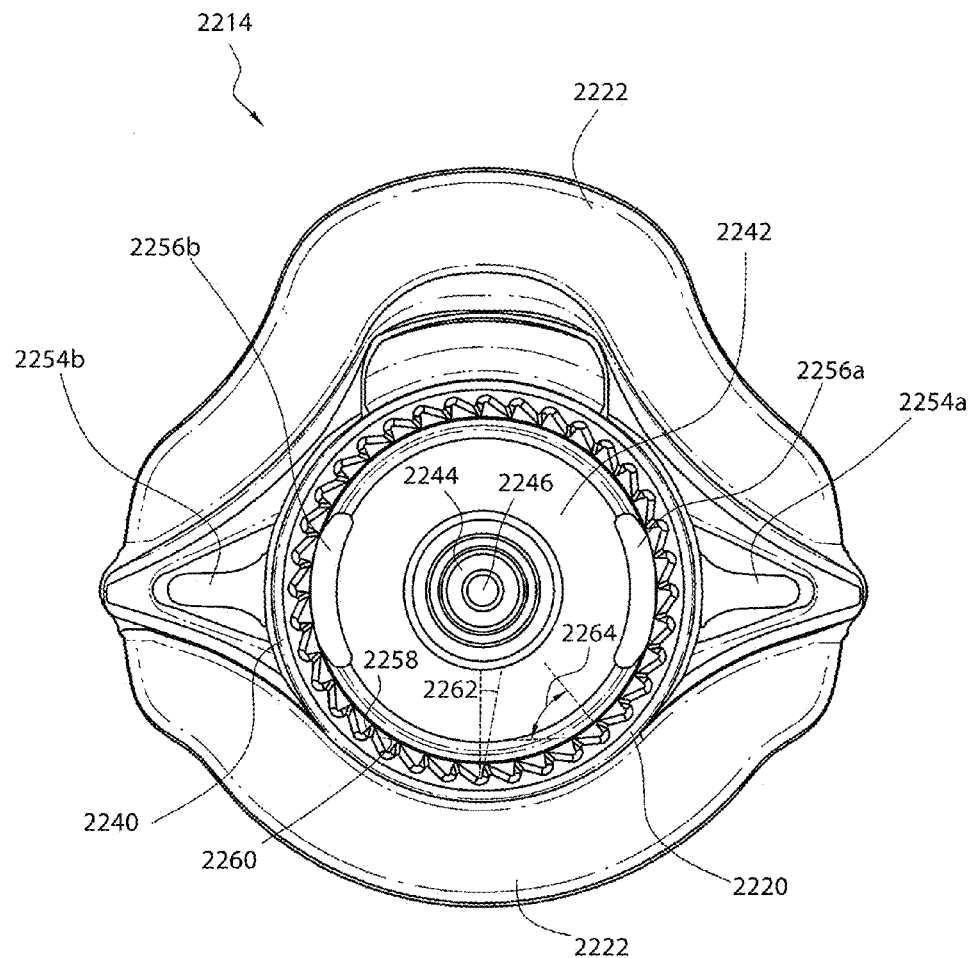
FIG. 67 is a top view of the base member of FIG. 64.
Figure 68:
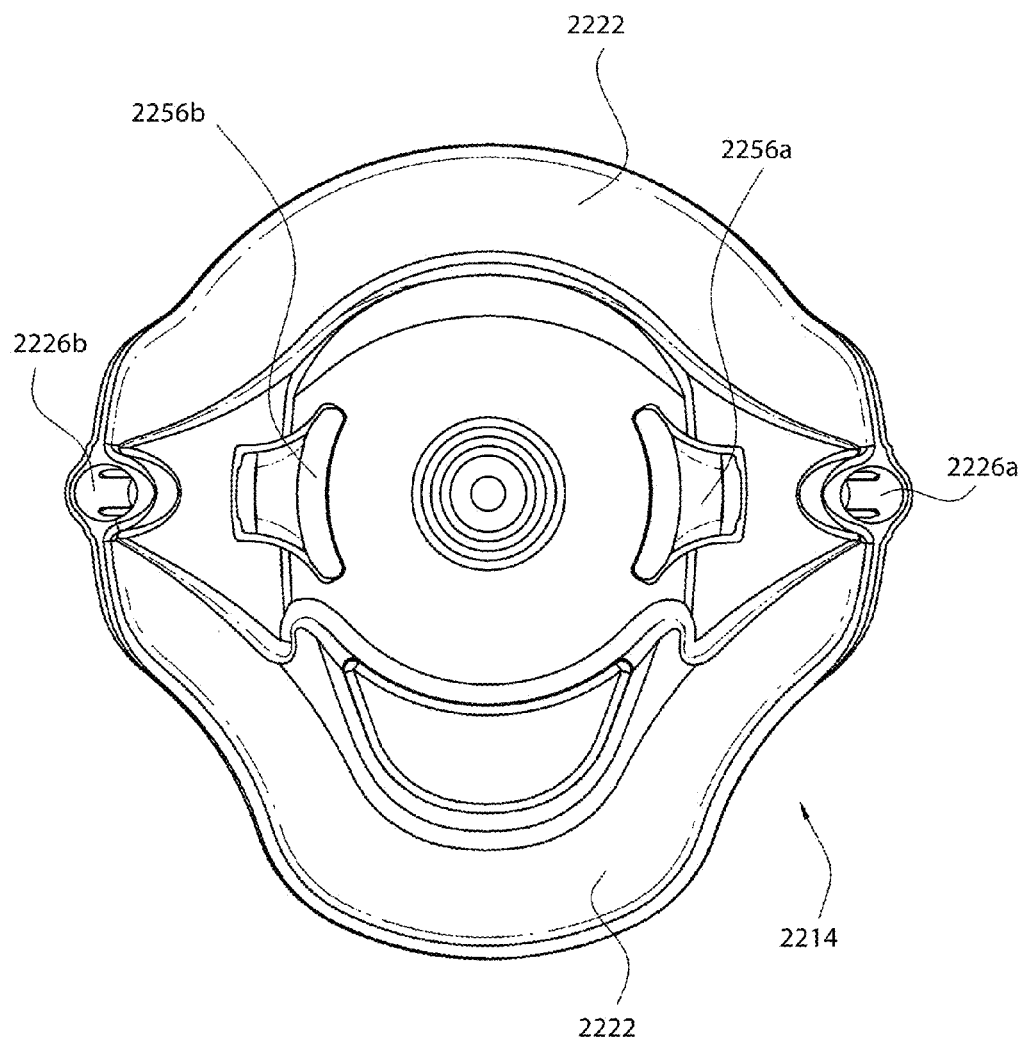
FIG. 68 is a bottom view of the base member of FIG. 64.
Figure 69:
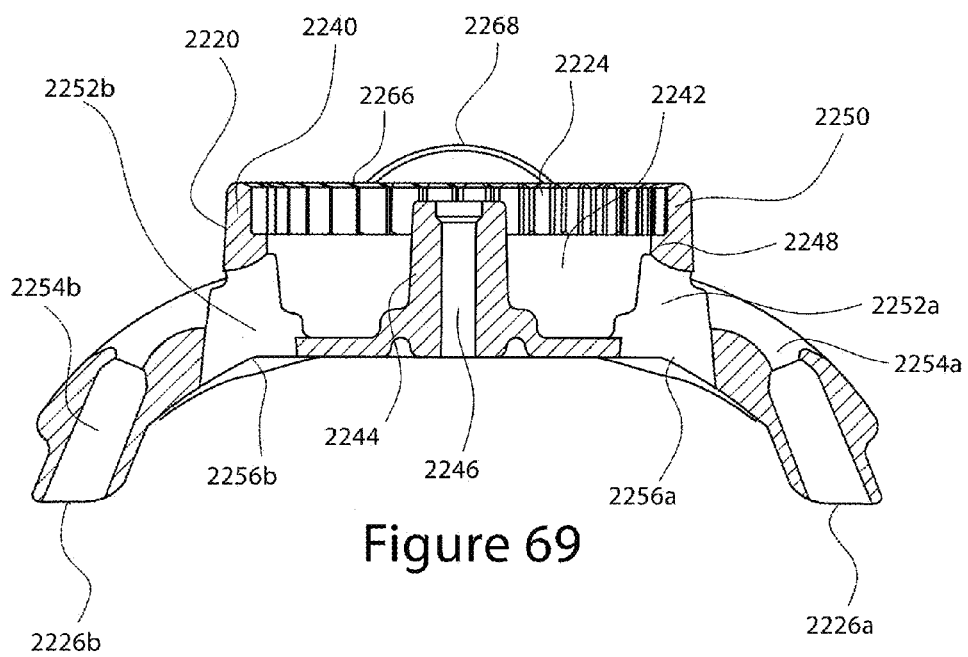
FIG. 69 is a cross sectional side view of the base member of FIG. 64.

FIG. 66 is a perspective view of the base member 2214. FIG. 67 is a top view of the base member 2214. FIG. 68 is a bottom view of the base member 2214. FIG. 69 is a cross sectional view of the base member 2214. The base member 2214 a mounting flange 2222 which can be mounted onto the outside structure of an article of footwear or other article, or the mounting flange 2222 can be mounted underneath an outer structure of the article so that at least a portion of the mounting flange 2222 is hidden from view. The mounting flange 2222 can be secured to the article by stitching, or in any other suitable manner such as using an adhesive, or using rivets, etc. The mounting flange 2222 can be contoured to fit a particular portion of the article (e.g., the back of a shoe), or the mounting flange can be flexible to fit a variety of shapes. The mounting flange 2222 can extend fully or partially around the circumference of the housing 2220. The mounting flange 2222 can be somewhat resilient to accommodate the flexing of the article during use. In some embodiments, the mounting flange 2222 can be omitted, and the base member 2214 or housing 2220 can be mounted to the article by a screw or rivet or other fastener. For example, a threaded portion of the base member 2214 or housing 2220 can be threaded into a corresponding threaded connector on the article. In some embodiments, the mounting flange 2222 is connected to the article and the reel 2204 is subsequently attached to the flange 2222.

The housing 2220 can be attached to, or integrally formed with, the mounting flange 2222 and can extend upward therefrom, as illustrated. The housing 2220 can include an outer wall 2240 that surrounds a depression 2242, which can be substantially circular in shape. A shaft 2244 can extend axially upwardly from the base of the depression 2242, and the shaft 2244 can be aligned substantially coaxially with the depression 2242. The shaft 2244 can include a step 2245 or beveled portion where the shaft 2244 meets the base of the depression 2242. The shaft 2244 can include a bore 2246 in the center thereof which can facilitate the securing of the knob member 2218 to the housing 2220. The bore 2246 can be threaded or otherwise configured to axially secure a fastener that is inserted therein. The shaft 2244 can form a supporting surface about which the spool member 2216 can rotate.

The outer wall 2240 of the housing 2220 can be substantially cylindrical in shape and can be substantially coaxial with the shaft 2244. The inner surface of the outer wall 2240 can include a lower portion 2248, and an upper portion 2250. The lower portion 2248 can be generally smooth and can include a step 2251 or beveled portion where the outer wall 2240 meets the base of the depression 2242. The lower portion 2248 can include one or more lace openings 2252a-b which can be in connected to the lace holes 2226a-b by lace channels 2254a-b so that the lace 2206 can pass through the housing 2220 and enter the depression 2242. As can best be seen in FIG. 69, a lower portion of the lace channels 2254a-b nearest to the lace holes 2226a-b can be closed while an upper portion of the lace channels 2254a-b nearest to the lace openings 2252a-b can be open at the top. Also, the lace channels 2254a-b and/or the lace openings 2252a-b can be in connected to openings 2256a-b formed in the base of the housing 2220. The openings 2256a-b and the open tops of the lace channels 2254a-b can provide access to the lace 2206 during use and installation, and can also provide an exit pathway for water or other material that may enter the depression 2242 during use, and can facilitate the molding of the lace channels 2254a-b when the base member 2214 is made of few components (e.g., a single integrated piece).

The housing 2220 can include housing teeth 2224 that extend radially inwardly from the upper portion 2250 of the outer wall 2240. In the illustrated embodiment, the housing includes 36 housing teeth 2224, but any other suitable number of housing teeth 2224 can be used. As can best be seen in FIG. 67, each of the housing teeth 2224 can include a first side 2258 and a second side 2260. The first side 2258 can be shorter than the second side 2260, and in some embodiments, the first side 2258 can be about half as long as the second side 2260. In some embodiments, the first side 2258 of the housing teeth 2224 can be at least about 0.5 mm long and/or no more than about 1.0 mm long, and can be about 0.85 mm long, and the second side can be at least about 1.0 mm long and/or no more than about 2.0 mm long, and can be about 1.75 mm long. Other dimensions outside of these specific ranges are also possible. The first side 2258 of the housing teeth 2224 can be angled away from a line that points directly radially inwardly by and angle 2262 that can be at least about 5° and/or at most about 15°, and can be about 10° in some embodiments. The second side 2260 of the housing teeth 2224 can be angled away from a line that points directly radially inwardly by an angle 2264 that can be at least about 45° and/or no more than about 65°, and can be about 55° in some embodiments. Other angles outside these specially identified ranges are also possible. In some embodiments, the transition between housing teeth 2224 and between the first and second sides 2258, 2260 of the housing teeth 2224 can be curved, but hard edged transitions can also be used. The housing teeth 2224 can be configured to interface with the pawls 2236 as discussed in greater detail below. The housing teeth 2224 can include angled top surfaces 2266 to facilitate the transition of the pawls 2236 from the disengaged to engaged positions as will be described in greater detail below.

The base member 2214 can include one or more guard pieces 2268 that can extend axially upwardly further than the outer wall 2240 of the housing 2220 such that the guard piece 2268 can function to cover a portion of the knob member 2218 when the knob member 2218 is attached to the housing 2220. In some embodiments, the guard piece 2268 can be omitted. In some embodiments, the reel 2204 can be disposed within a recess of the article such that a portion of the article itself extends to cover a portion of the knob member 2218. The guard 2268, or portion of the article functioning as a guard, can protect the knob member 2218 and can reduce the occurrence of accidental disengagement of the knob member 2218.

Figure 70A:
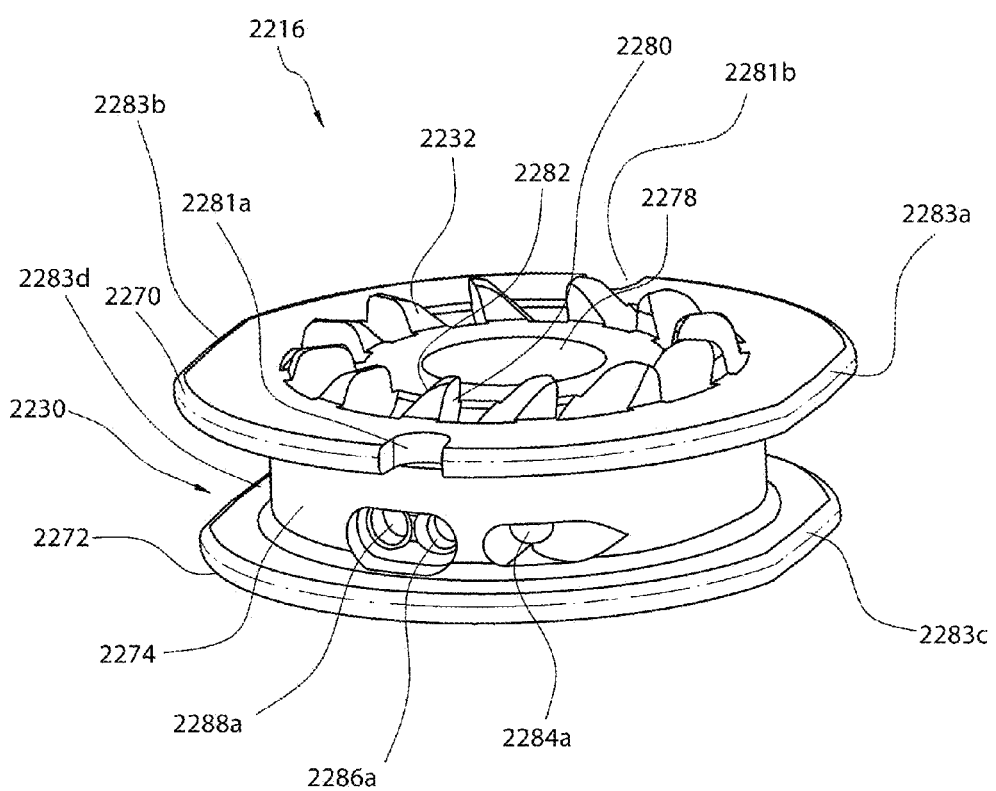
FIG. 70A is perspective view of the spool member from the reel of FIG. 63.
Figure 71:
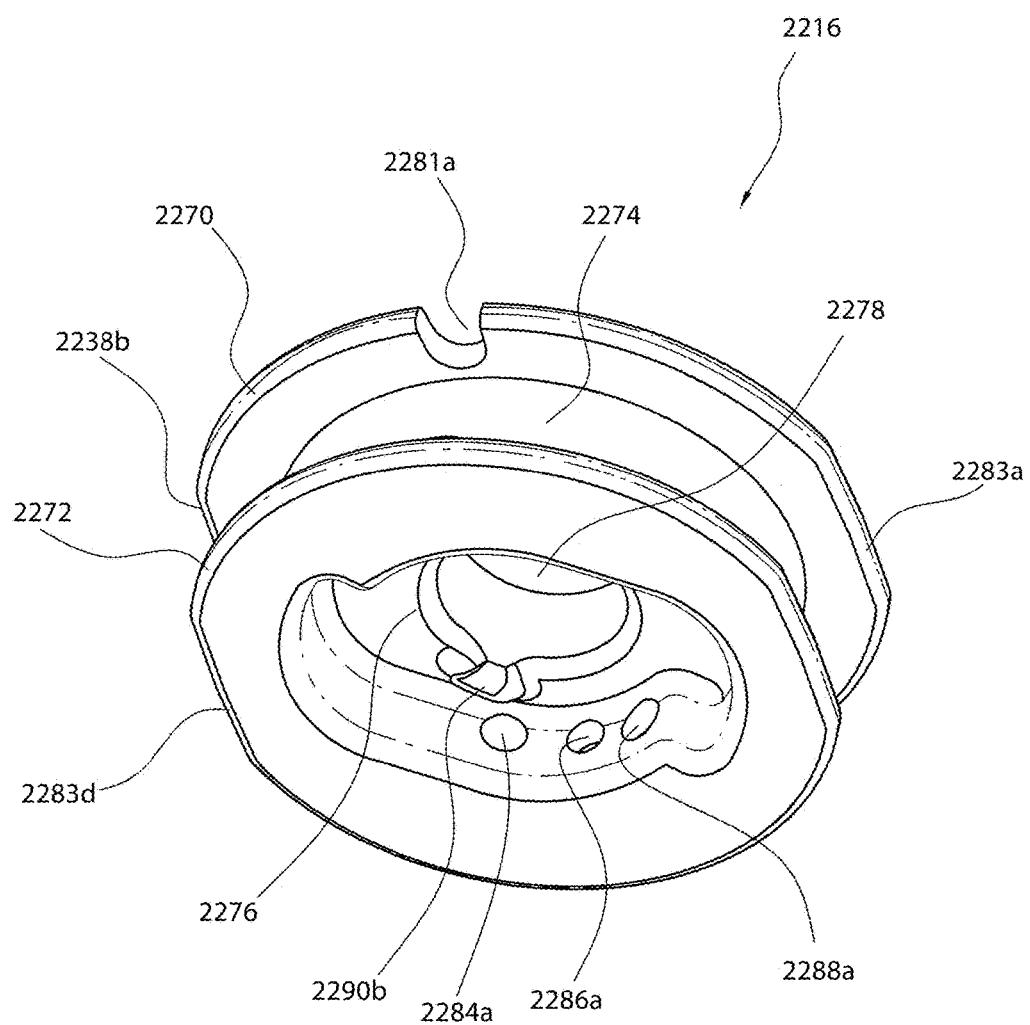
FIG. 71 is another perspective view of the spool member of FIG. 70A.
Figure 72:
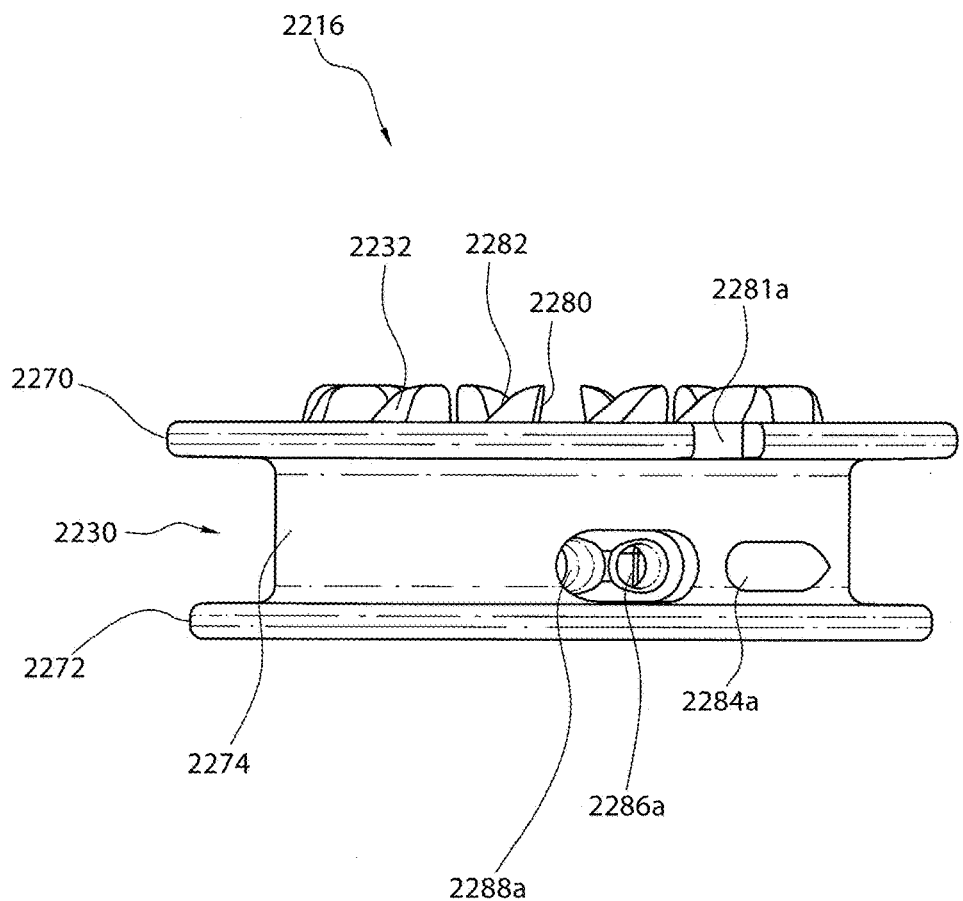
FIG. 72 is a side view of the spool member of FIG. 70A.
Figure 73A:
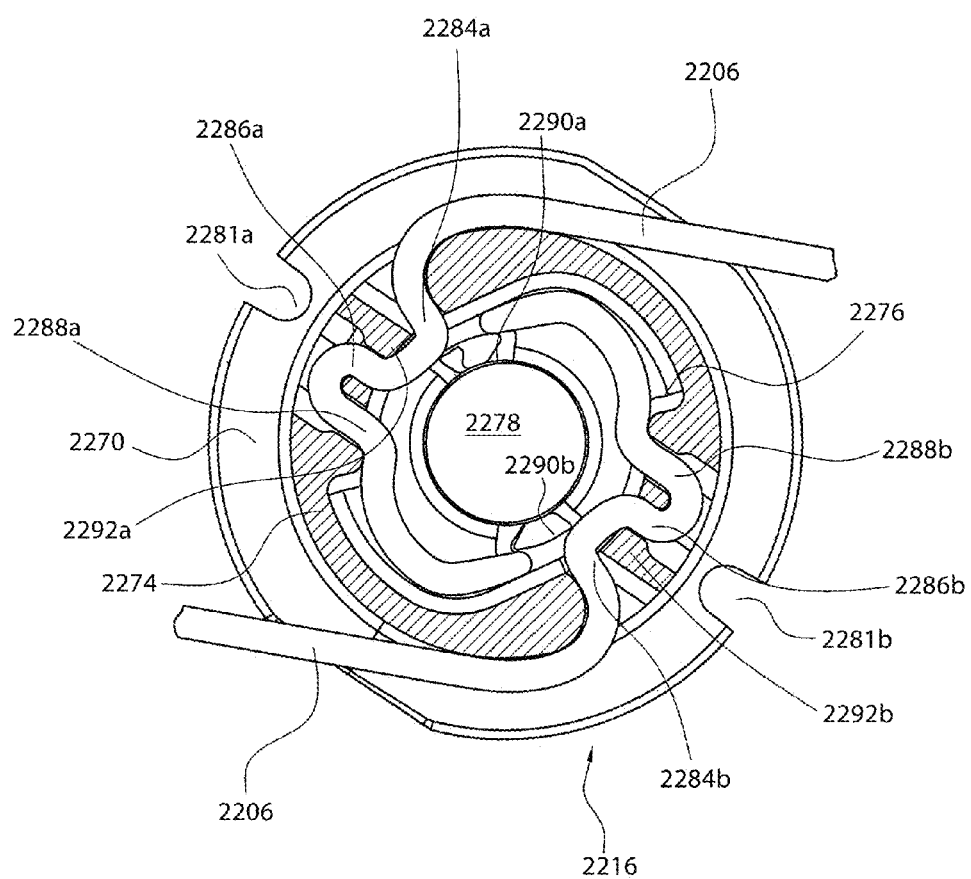
FIG. 73A is a cross sectional view of the spool member of FIG. 70A shown with a lace secured thereto in a first configuration.
Figure 73B:
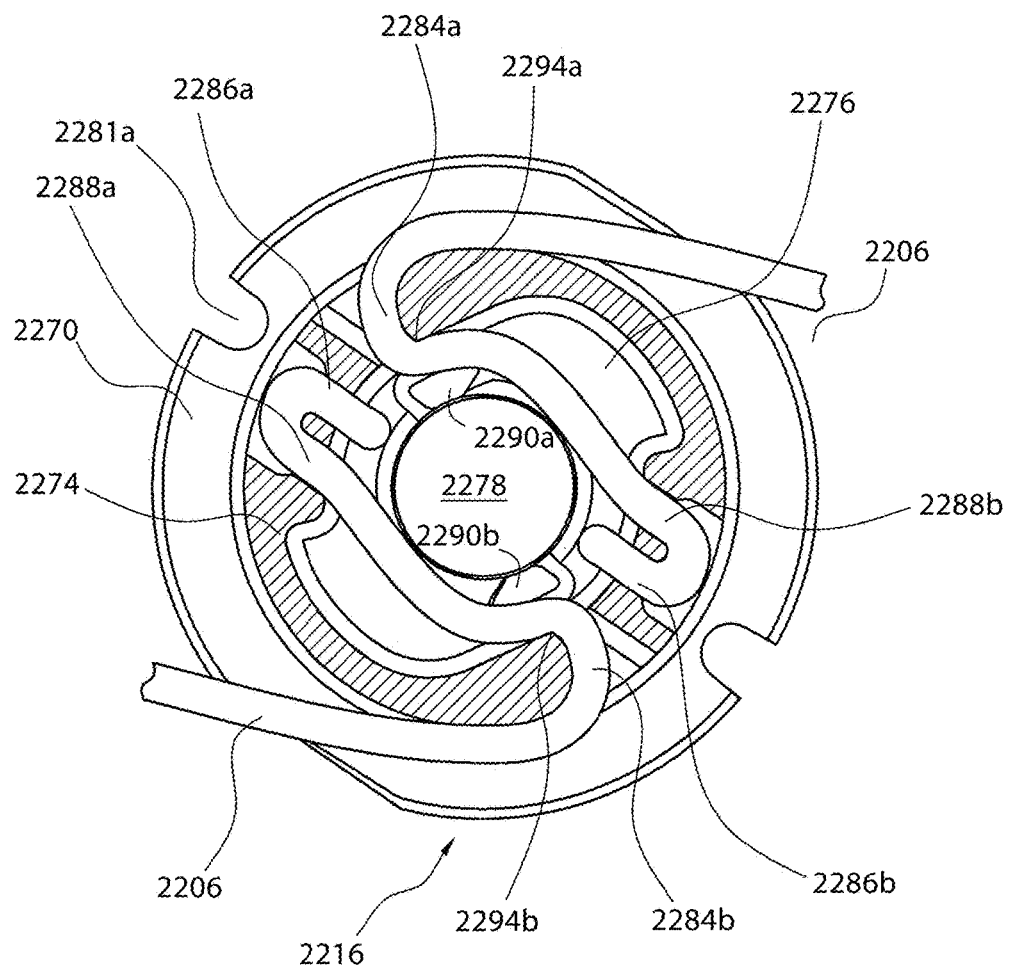
FIG. 73B is a cross sectional view of the spool member of FIG. 70A shown with a lace secured thereto in a second configuration.
Figure 74:
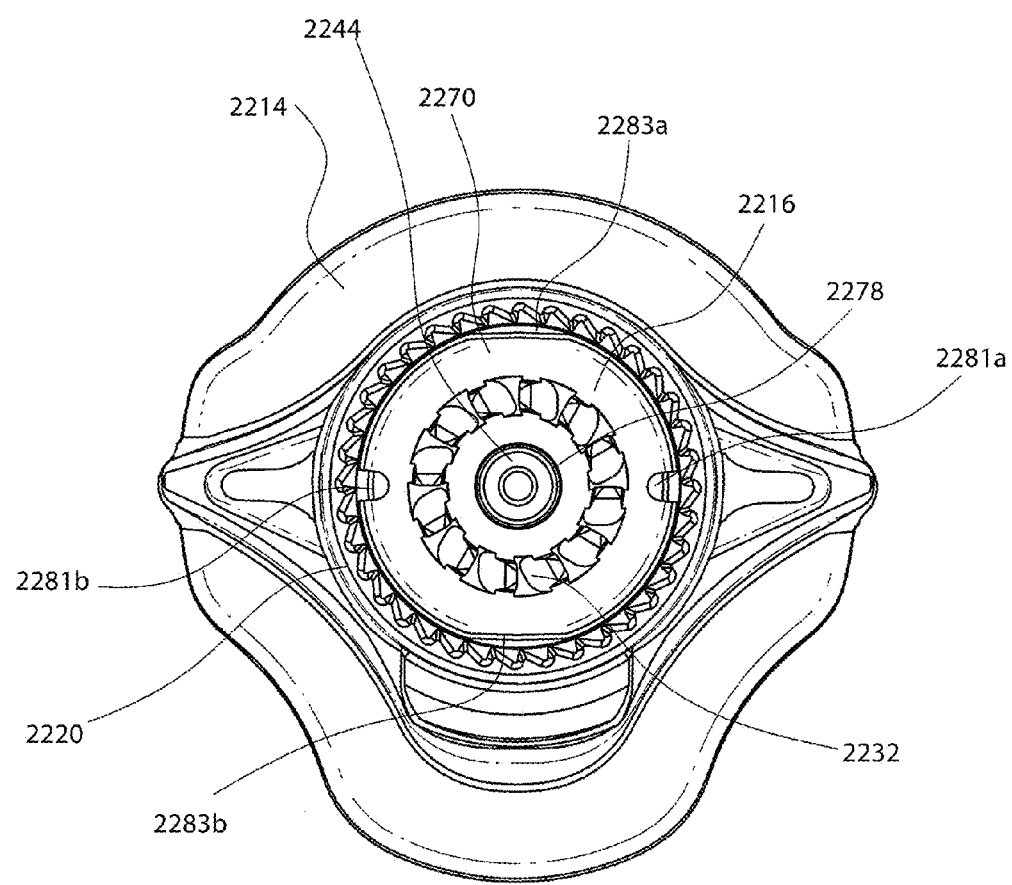
FIG. 74 is a top view of the spool member of FIG. 70A shown disposed in the housing of the base member of FIG. 64.

FIG. 70A is a perspective view of the spool member 2216. FIG. 71 is another perspective view of the spool member 2216. FIG. 72 is a side view of the spool member 2216. FIGS. 73A-B are a cross sectional bottom views of the spool member 2216 with the lace 2206 attached thereto. FIG. 74 is a top view of the spool member 2216 disposed within the housing 2220.

The spool member 2216 can include an upper flange 2270 and a lower flange 2272 with a substantially cylindrical wall 2274 formed therebetween. The outer surface of the wall 2274, the bottom surface of the upper flange 2270, and the top surface of the lower flange 2272 can form a channel 2230 for collecting the lace 2206 as it is wound around the spool member 2216. The inner surface of the wall 2274 can surround a depression 2276 formed in the bottom of the spool member 2216. A central opening 2278 can extend through the ceiling of the depression. As can best be seen in FIG. 74, when the spool member 2216 is disposed within the depression 2242 of the housing 2220, the shaft 2244 can pass through the central opening 2278 of the spool member 2216. The step 2245 or beveled edge at the bottom of the shaft 2244 can be received into the depression 2276 formed in the bottom of the spool member 2216. The lower flange 2272 can be formed slightly smaller than the upper flange 2270 (as can best be seen in FIG. 72) so that the lower flange 2272 can fit inside the step 2251 or beveled edge at the edge of the depression 2242, and to facilitate removal and/or installation of the spool member 2216 from/into the housing 2220 with the lace 2206 attached. Thus, in some embodiments, the bottom surface of the lower flange 2272 can sit flush against the base of the depression 2242. In some embodiments, a portion of the housing 2220 can be configured to contact a portion of the spool member 2216 to maintain the bottom surface of the lower flange 2272 a small distance from the base of the depression to reduce the amount of friction as the spool member 2216 rotates. When the spool member 2216 is fully inserted into the depression 2242 of the housing 2220, the top surface of the upper flange 2270 can substantially align with the top of the lower portion 2248 of the outer wall 2240 such that the upper flange 2270 does not overlap the housing teeth 2224.

Spool teeth 2232 can be formed on the top surface of the spool member 2216. In the illustrated embodiment, 12 spool teeth 2232 are shown, but any other suitable number of spool teeth 2232 can be used. Each of the spool teeth 2232 can include a first side 2280 and a second side 2282. The first side 2280 can be substantially vertical in some embodiments. In some embodiments, the first side can be angled by at least about 5° and/or by no more than about 15°, and in some embodiments by about 10° from the vertical plane. The second side 2282 can be angled by at least about 35° and/or by no more than about 55°, and in some embodiments by about 45° from the vertical plane. The first side 2280 can be at least about 1.5 mm long and/or no more than about 2.5 mm long, and can be about 2.0 mm long. The second side can be at least about 2.5 mm long and/or no more than about 3.5 mm long, and can be about 3.0 mm long. Dimensions and angles outside the identified ranges can also be used. The spool teeth 2232 can be configured to interface with the knob teeth 2234 as discussed in greater detail herein.

Figure 70B:
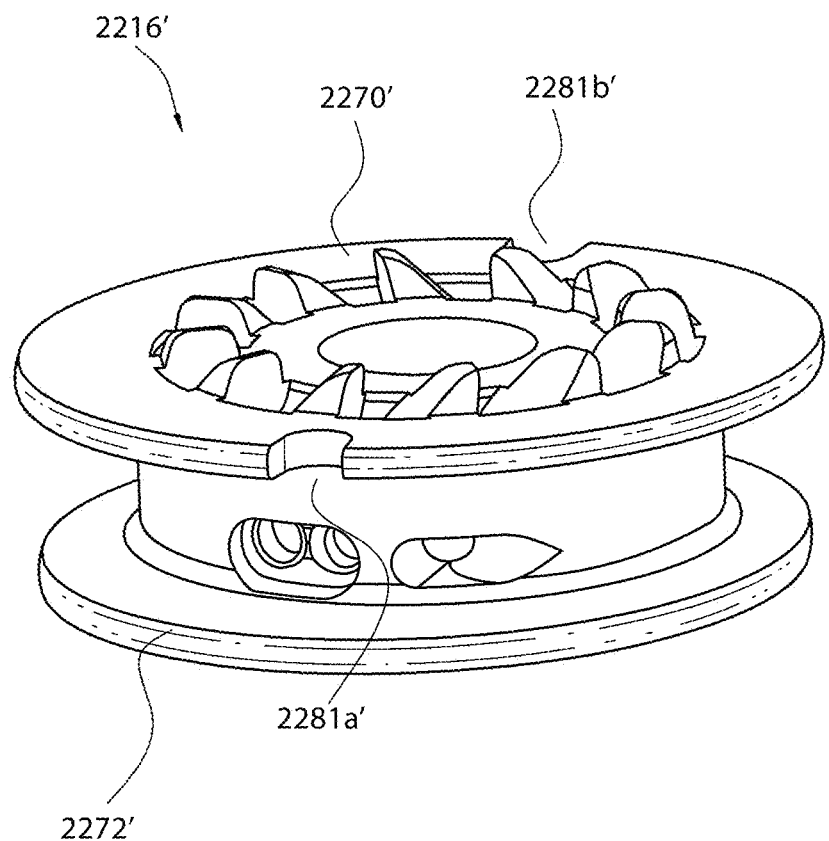
FIG. 70B is a perspective view of another embodiment of a spool member.

In some embodiments, one or more cutouts 2281a-b can be formed in the upper flange 2270 of the spool member 2216. Also, in some embodiments, the upper flange 2270 and/or the lower flange can be substantially circular in shape, but can have one or more flattened edges 2283a-d. The cutouts 2281a-b and/or the flattened edges 2283a-d can facilitate the removal of the spool member 2216 from the housing 2220 (e.g., when replacing the lace 2206). A screwdriver or other tool can be inserted between the spool member 2216 and the housing 2220 wall and the spool member 2216 can be pried out of the housing 2220. Many variations are possible. For example, FIG. 70B is a perspective view of a spool member 2216' which is similar to the spool member 2216 in many respects, except that the upper flange 2270' and the lower flange 2272' of the spool member 2216' do not have flattened edges 2283a-d. Thus, the upper flange 2270' and the lower flange 2272' can be substantially circular in shape. In some embodiments, the upper flange 2270' can include cutouts 2281a' and 2281b' which can facilitate the removal of the spool member 2216' from the housing 2220. In some embodiments, the flanges 2270' and 2272' that do not include flattened edges 2283a-d can prevent the lace 2206 from becoming trapped or wedged in the gaps formed between the housing 2220 and the flattened edges 2283a-d, especially when a relatively thin lace is used.

The depth of the channel 2230 can be at least about 1.5 mm and/or no more than about 2.5 mm, and in some cases can be about 2.0 mm. The channel 2230 can have a width that is at least about 3.0 mm and/or no more than about 4.0 mm, and in some cases can be about 3.5 mm. The outer surface of the wall 2274 can have a diameter of at least about 10 mm and/or no more than about 20 mm, and can be in some cases about 14 mm. Dimensions outside the given ranges are also possible. The lace 2206 can be generally small enough in diameter that the channel 2230 can hold at least about 300 mm of lace and/or no more than about 600 mm of lace, and in some embodiments about 450 mm of lace, although the spool member 2216 and lace 2206 can be configured to hold amounts of lace outside these given ranges.

The lace or cable can have a diameter of at least about 0.5 mm and/or no more than about 1.5 mm, and in some embodiments the diameter can be about 0.75 mm or 1.0 mm, although diameters outside these ranges can also be used. The lace 2206 can be a highly lubricious cable or fiber having a low modulus of elasticity and a high tensile strength. In some embodiments, the cable can have multiple strands of material woven together. While any suitable lace can be used, some embodiments can utilize a lace formed from extended chain, high modulus polyethylene fibers. One example of a suitable lace material is sold under the trade name SPECTRA™, manufactured by Honeywell of Morris Township, N.J. The extended chain, high modulus polyethylene fibers advantageously have a high strength to weight ratio, are cut resistant, and have very low elasticity. One preferred lace made of this material is tightly woven. The tight weave provides added stiffness to the completed lace. The additional stiffness provided by the weave offers enhanced pushability, such that the lace is easily threaded (e.g., into the reel 2204). Additionally, in some embodiments, the lace can be formed from a molded monofilament polymer. In some embodiments, the lace can be made from woven steel with or without a polymer or other lubrication coating.

One or more ends of the lace 2206 can be secured to the spool member 2216. In some embodiments, the lace 2206 can be removably or fixedly attached to the spool member 2216. In some embodiments, the lace 2206 can be threaded through a hole formed in the spool member 2216 and a knot can be formed in the end of the lace 2206, or an anchoring member can be attached thereto, to prevent the end from being pulled back through the hole. In some embodiments, the lace 2206 can be tied to a portion of the spool member 2216. The lace can also be secured to the spool member 2216 by an adhesive any other suitable manner. In some embodiments, the lace 2206 is secured to the spool member 2216 by weaving the lace 2206 through a series of openings that cause the lace 2206 to turn at such angles so as to produce sufficient friction to prevent the lace 2206 from being dislodged from the spool member 2216. In some embodiments, the lace 2206 wraps over itself so that the lace 2206 tightens on itself when pulled. In some embodiments, only one end of the lace 2206 is secured to the spool member 2216, with the other end of the lace 2206 being secured to the base member 2214 or to the article being tightened.

The spool member 2216 can include a first set of lace holes 2284a, 2286a, 2288a which can be configured to secure a first end of the lace 2206. In some embodiments, a second set of lace holes 2284b, 2286b, 2288b can be used to secure the second end of the lace 2206. Lace guides 2290a-b can also be formed in the depression 2276 to facilitate the securing of the lace 2206 to the spool member 2216.

In the embodiment shown in FIG. 73A, a first end of the lace 2206 can pass through the lace hole 2284a into the depression 2276. The lace guide 2290a can direct the lace 2206 toward the lace hole 2286a, and in some embodiments, the lace guide 2290a can be positioned such that the lace 2206 is wedged between the lace guide 2290a and a portion 2292a of the wall 2274 between the holes 2284a and 2286a. The lace 2206 can exit the depression 2276 through the lace hole 2286a and then turn an angle of approximately 180° to reenter the depression through the lace hole 2288a. In some embodiments, the tip of the first end of the lace 2206 can be tucked into the opposing lace guide 2290b to prevent the tip from moving about within the depression 2276 and interfering with the rotation of the spool member 2216. In some embodiments, the amount of lace 2206 that passes through the lace holes 2284a, 2286a, 2288a can be configured so that only a small portion of the lace 2206 reenters the depression 2276 through the hole 2288a so that the tip is not tucked into the opposing lace guide 2290b. The second end of the lace 2206 can be secured to the spool member 2216 by the lace holes 2284a, 2286b, 2288b, and the lace guide 2290b, and the portion 2292b of the wall 2274 in like manner.

Other lace securing configurations are possible. For example, in the embodiment shown in FIG. 73B, the first end of the lace 2206 passes through the lace hole 2284a to enter the depression 2276. The lace guide 2290 can direct the lace 2206 toward the lace hole 2288b, and the lace guide 2290a can be configured such that the lace 2206 is wedged between the lace guide 2290a and the portion 2294a of the wall adjacent to the lace hole 2284a. The lace 2206 can pass through the lace hole 2288b and then turn an angle of approximately 180° to reenter the depression 2276 through the lace hole 2286b. The second end of the lace 2206 can be secured to the spool member 2216 by the lace holes 2284b, 2288a, 2286a, and the lace guide 2290b and the portion 2294b of the wall 2274 in like manner.

Figure 73C:
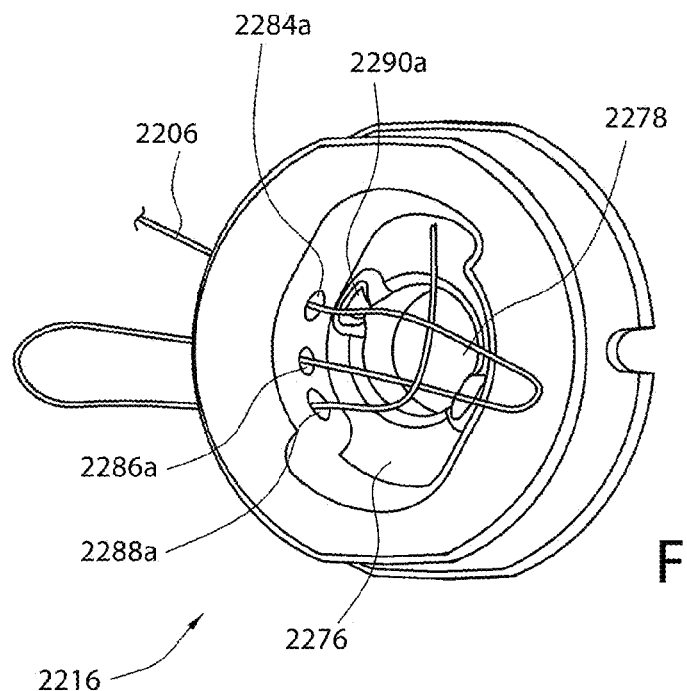
FIG. 73C is a perspective view of the spool member of FIG. 70A showing a lace being secured to the spool member in a third configuration.
Figure 73D:
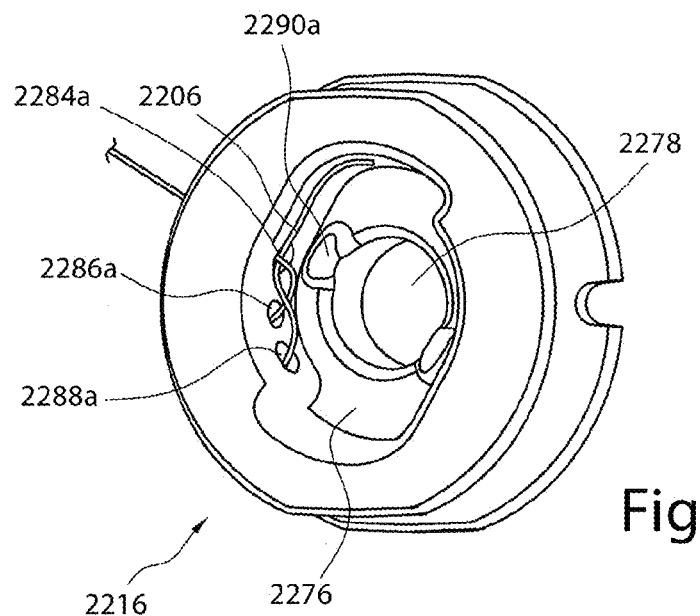
FIG. 73D is a perspective view of the spool member of FIG. 70A showing the lace being secured to the spool member in a fourth configuration.

FIGS. 73C and 73D illustrate another manner in which the lace 2206 can be secured to the spool member 2216. As shown in FIG. 73C, the end of the lace 2216 is threaded through the lace hole 2284a into the depression 2276, then through the lace hole 2286a out of the depression 2276, and then through the lace hole 2288a back into the depression 2276. The end of the lace 2206 can then be passed through the loop in the lace formed between the lace holes 2284a, 2286a, as shown in FIG. 73C. The lace 2206 can then be tightened so that the lace crosses under itself as shown in FIG. 73D. For example, the loose end of the lace 2206 can be held with one hand while pulling the loop formed between the lace holes 2284a and 2286a to remove the slack from the loop formed between the lace holes 2286a and 2288a. Then the slack in the loop formed between the lace holes 2284a and 2286a can be pulled out of the depression 2276 through the lace hole 2284a until the lace tightens down on itself. Thus, once tightened, the lace 2206 bears down on itself more tightly when it is pulled, thereby preventing the lace 2206 from disengaging from the spool member 2216.

The lace can pass over the top of the portion of the loop that is closest to the lace hole 2288a and then under the portion of the loop that is furthest from the lace hole 2288a, as shown. Then, when the lace is tightened, the loose end of the lace 2206 can be directed generally toward the base of the depression 2276, rather than being directed generally out from the depression 2276 as would be the case if the lace were threaded over the top of the portion of the loop furthest from the lace hole 2288a. By biasing the loose end of the lace toward the base of the depression 2276, the loose end of the lace can be prevented from interfering with the insertion of the spool member 2216 into the housing 2220. The lace guide 2190a can be positioned to keep the loose end of the lace 2206 positioned near the periphery of the depression 2276 so that the loose end of the lace 2206 does not enter the central opening 2278 or otherwise interfere with the spool member 2216 being inserted into the housing 2220.

Figure 75:
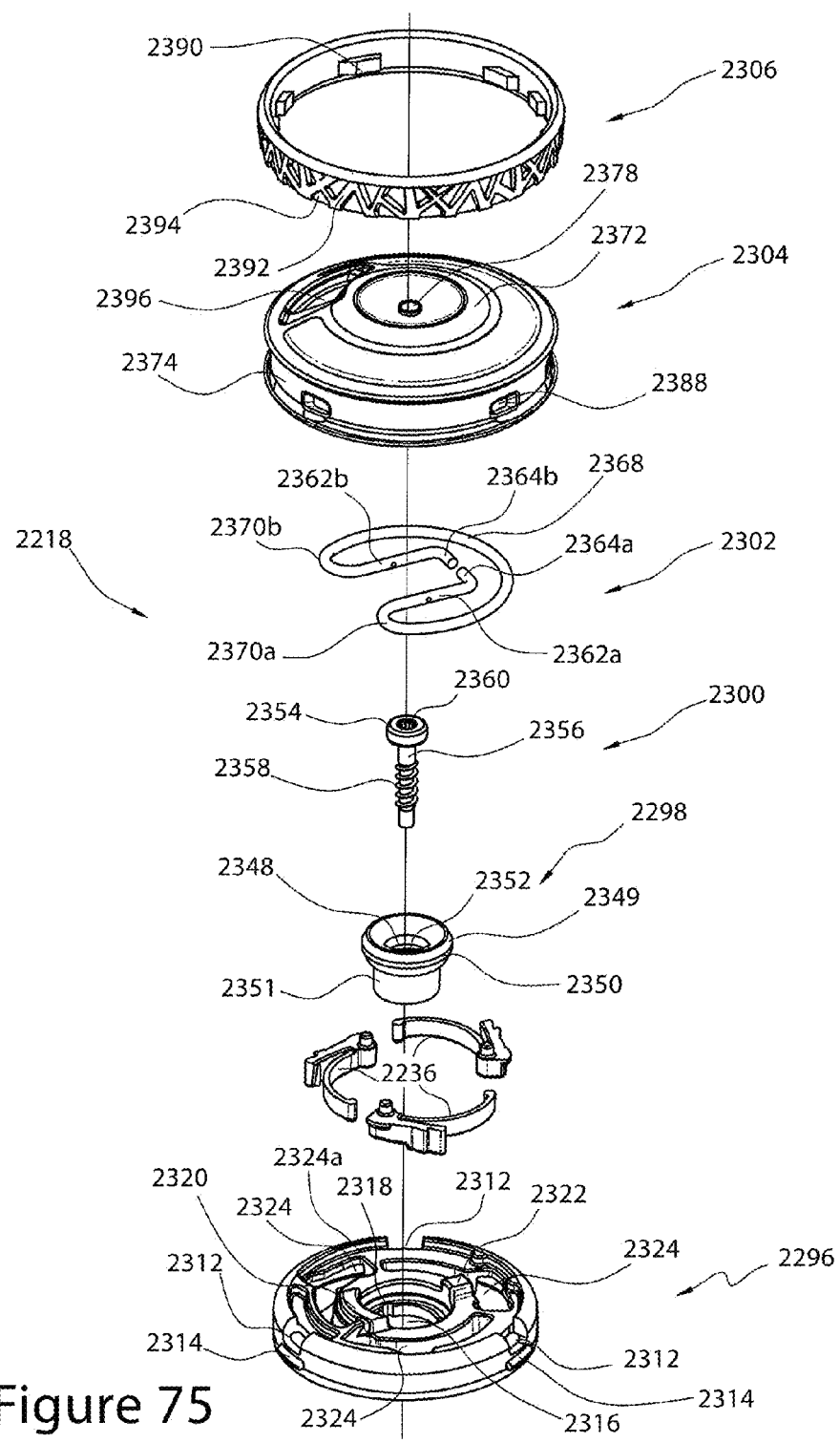
FIG. 75 is an exploded perspective view of the knob member from the reel of FIG. 63.
Figure 76:
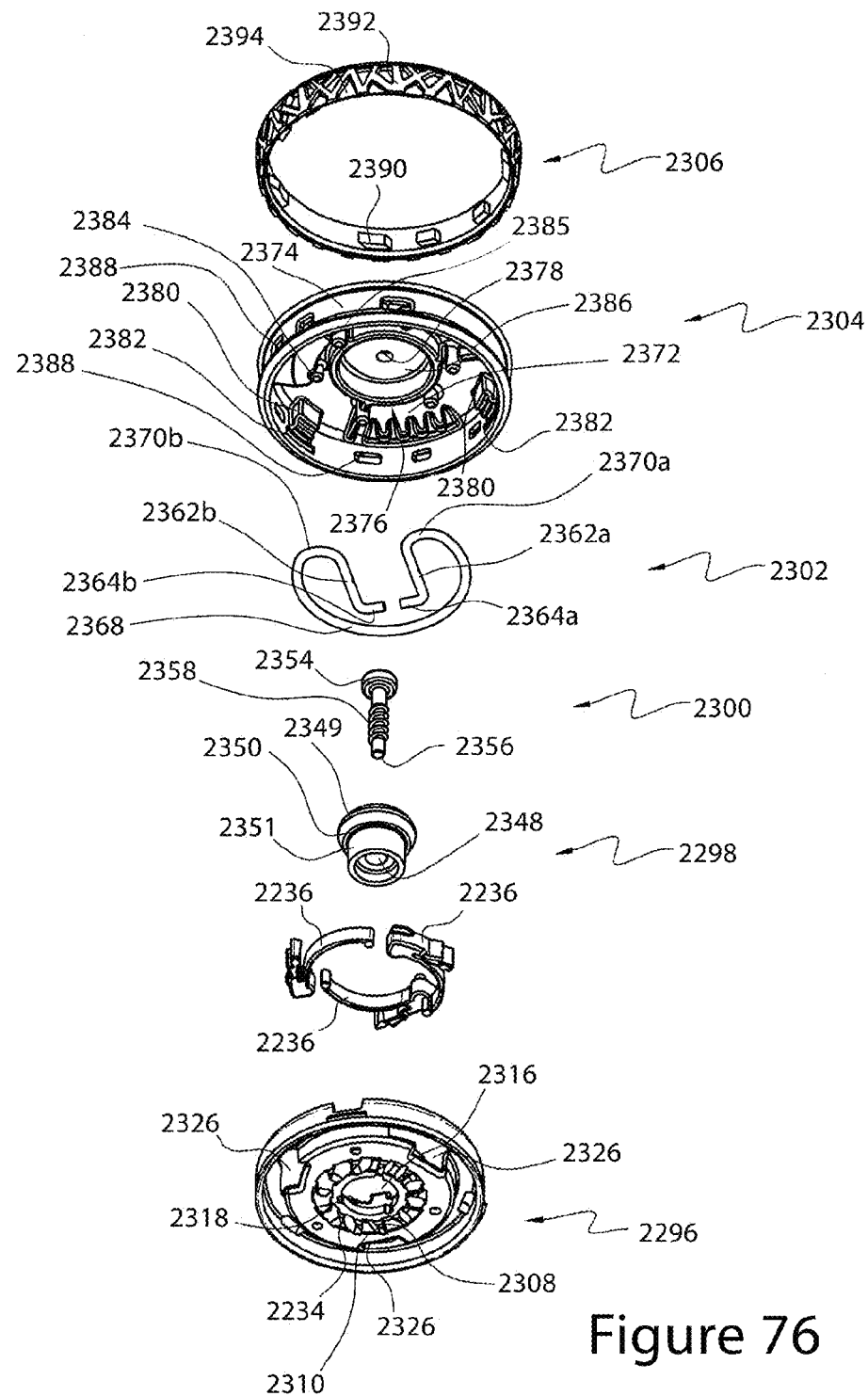
FIG. 76 is another exploded perspective view of the knob member from FIG. 75.

FIG. 75 is an exploded perspective view of the knob member 2218. FIG. 76 is another exploded perspective view of the knob member 2218. The knob member can include a knob core 2296, pawls 2236, a spring bushing 2298, a fastener 2300, a knob spring 2302, a knob cover 2304, and a knob grip 2306.

The knob core 2296 can be generally disc-shaped. The knob core 2296 can include knob teeth 2234 formed on the bottom surface thereof. In the illustrated embodiment, 12 knob teeth 2234 are shown, but any other suitable number of knob teeth 2234 can be used. In some embodiments, the same number of knob teeth 2234 and spool teeth 2232 can be used, and the knob teeth 2234 can be shaped similar to, or the same as, the spool teeth 2232, except that that the knob teeth 2234 are oriented in the opposite direction so that the knob teeth 2234 can engage the spool teeth 2232. Accordingly, the dimensions described above in connection with the spool teeth 2232 can also apply to the knob teeth 2234. When the knob member 2218 is rotated in the tightening direction, the first sides 2308 of the knob teeth 2234 can press against the first sides 2280 of the spool teeth 2232 to drive the spool member 2216 in the tightening direction. When a lace 2206 is tightened around the spool member 2216 applying a force to the spool member 2216 to cause it to tend to twist in the loosening direction, the second sides 2282 of the spool teeth 2232 can bear against the second sides 2310 of the knob teeth 2234 so that the force is transferred to the knob member 2218 to cause it to tend to twist in the loosening direction. As will be discussed below, the force can cause the pawls 2236 to engage with the housing teeth 2224 to prevent the knob member 2218 and the spool member 2216 from rotating in the loosening direction, thereby maintaining the lace 2206 in the tightened configuration.

The knob core 2296 can include features to facilitate the securing of the knob cover 2304 thereto. The knob core 2296 can include notches 2312 formed in the top surface thereof near the periphery of the knob core 2296. Protrusions 2314 can extend radially outwardly from the periphery of the knob core 2296 at locations below the notches 2312. The knob core 2296 can include a central opening 2316 through the center thereof, which can be configured to accept the spring bushing 2298. A top portion of the central opening 2316 can be wider than a lower portion of the central opening 2316 forming a step 2318 therein. The knob core 2296 can also include features to facilitate the securing of the knob spring thereto, including, for example, a wide engagement tab 2320 and a narrow engagement tab 2322.

The knob core 2296 can also include pawl depressions 2324, configured to accept the corresponding pawls 2236. The pawl depressions 2324 can be generally shaped similarly to the pawls 2236, but can be somewhat larger than the pawls 2236 to allow the pawls 2236 to pivot and move within the pawl depressions 2324 during operation, as is described in greater detail elsewhere herein. The pawl depressions 2324 can include pawl openings 2326 formed in a portion of the base and/or side thereof to allow a portion of the pawls (e.g., the pawl teeth) to extend through the knob core 2296 (as can be seen in the assembled knob member 2218 shown in FIG. 64) and interface with the housing teeth 2224.

Figure 77:
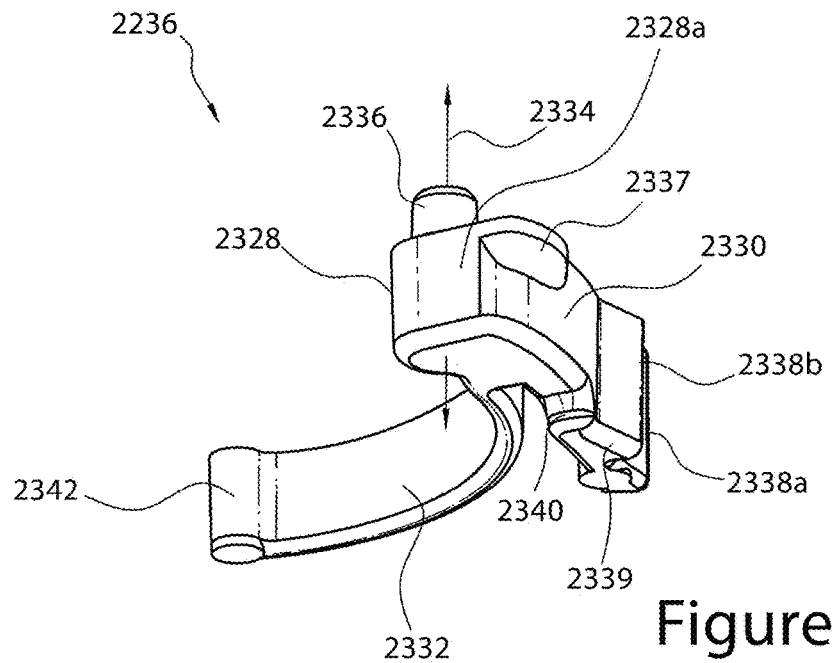
FIG. 77 is a perspective view of a pawl from the knob member of FIG. 75.
Figure 78:
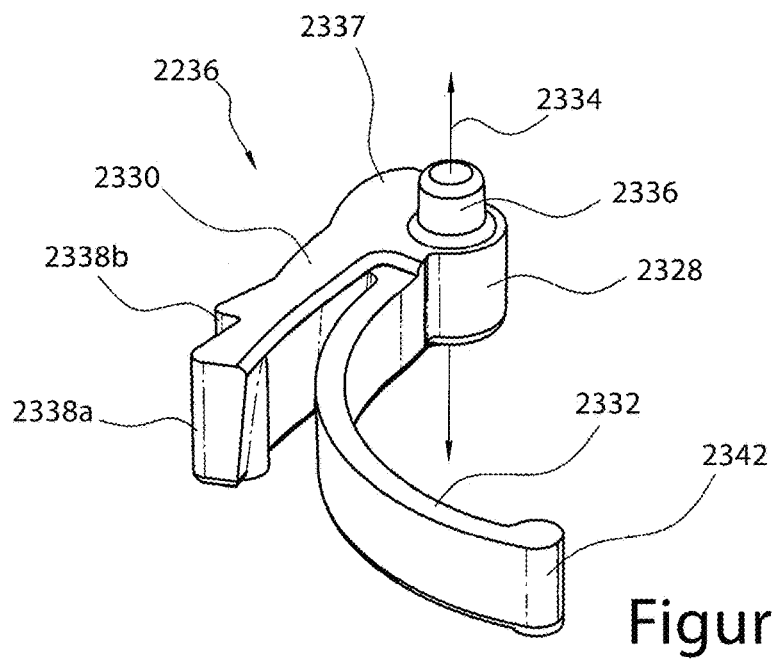
FIG. 78 is another perspective view of the pawl from the FIG. 77.

FIGS. 77 and 78 are perspective views of a pawl 2236. The pawl 2236 can include a pawl base 2328, a pawl beam 2330, and a pawl spring 2332. The pawl base 2328 can be configured to interface with the knob core 2296 and/or the knob cover 2304 so that the pawl 2236 can pivot about an axis 2334. A pivot tab 2336 can extend upward from the pawl base 2328 along the axis 2334. The pivot tab 2336 can be substantially cylindrical in shape and can be coaxial with the axis 2334. A flange 2337 can extend out from one side of the pawl base 2328, and the flange 2337 can facilitate the pivoting of the pawl 2236. As can be seen in FIGS. 77 and 78, in some embodiments, the pawl beam 2330, the pawl spring 2332, and other components of the pawl 2236 can be integrally formed (e.g., molded) as a single piece.

The pawl beam 2330 can be formed of a material, thickness, and length such that the pawl beam 2330 is substantially rigid and does not flex as the pawl 2236 is displaced by the housing teeth 2224 when the knob member 2218 is rotated in the tightening direction. One or more pawl teeth 2338a-b can be positioned near the end of the pawl beam 2330 opposite the pawl base 2328. In the embodiment shown, two pawl teeth 2338a-b are used, but any other suitable number of pawl teeth 2338a-b can be used instead. The pawl teeth 2338a-b, and in some cases the entire pawl beam 2330, can have an angled or beveled bottom surface 2339 which can facilitate the transition of the knob member 2218 from the disengaged position to the engaged position, as is discussed in greater detail elsewhere herein. The pawl beam 2330 can include a step 2340 formed where the end of the pawl beam 2330 extends lower than the rest of the pawl 2236. The downward extending portion of the pawl beam can be configured to extend through, or into, the pawl opening 2326 formed in the pawl depression 2324 of the knob core 2296.

Figure 79:
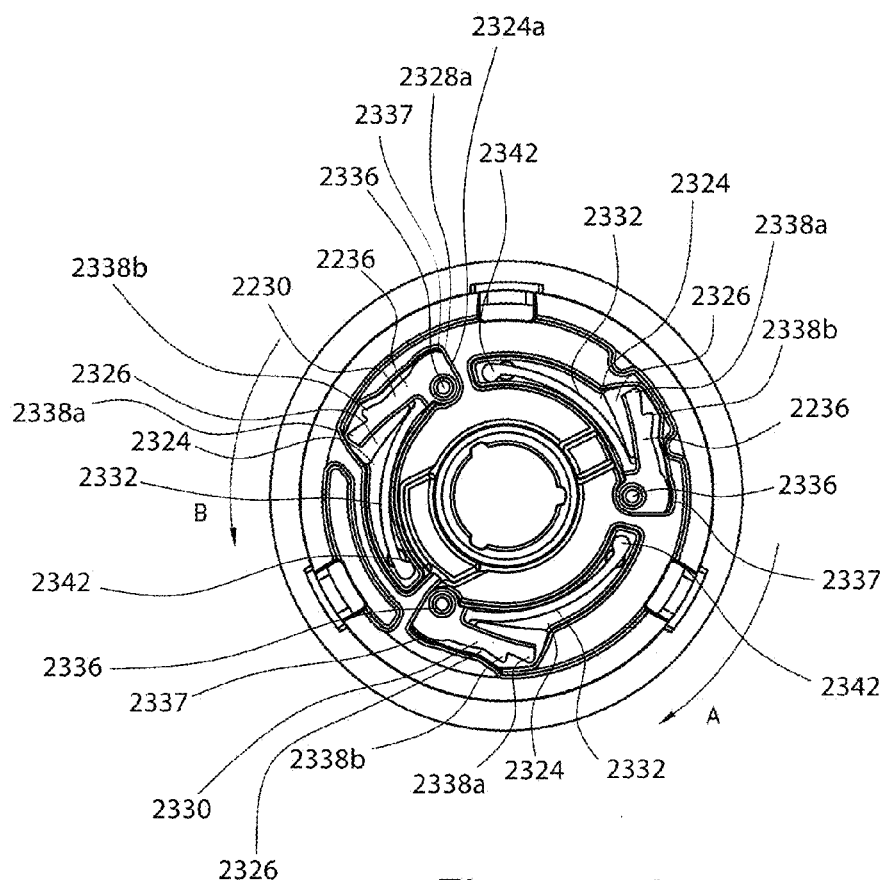
FIG. 79 is a top view of the pawls of FIG. 75 disposed in the knob core of FIG. 75, with the pawls configured to engage the housing teeth of the housing.

The pawl base 2328 can include an end surface 2328a configured to engage surface 2324a of pawl depression 2324 (as can be seen in FIG. 79). In some embodiments, as pressure is applied to one or more pawl teeth 2338, the load can be transferred through pawl beam 2330 to the engagement of end surface 2328a and surface 2324a. In some embodiments, as the pawl 2236 pivots radially outwardly about the axis 2334, the end surface 2328a of the pawl base 2328 can abut against the surface 2324a of the pawl depression 2324, thereby limiting the distance that the pawl 2326 can pivot radially outwardly. For example, the pawl 2236 can be permitted to pivot radially outwardly enough to engage the housing teeth 2224, but not significantly further. This can relieve pressure off of the pawls 2236 when a loosening force is applied to the knob member 2218, which can produce a component of force urging the pawls 2236 radially outward, as discussed below. The interface between the surfaces 2328a and 2324a can also limit the radial movement of the pawls 2236 when the knob member 2218 is in the disengaged position, thereby keeping the pawls 2236 radially inward enough that the knob member 2218 can be pressed to the engaged position without substantial interference from the pawls 2236. In some embodiments, pawl 2236 is positioned in pawl depression 2324 and is generally trapped between the knob cover 2304 and the knob core 2296. As explained below, top tabs 2384 can engage pivot tab 2336 to inhibit axial movement of the pawl 2236. Similarly, beam tabs 2385 extending downward from knob cover 2304 can engage the upper surface of the pawl beam 2330 to inhibit axial movement thereof.

The pawl spring 2332 can be a cantilever or arch spring as shown in the illustrated embodiment, but any other suitable type of spring can be used. The pawl spring 2332 can extend out from the pawl base 2328 in the same general direction as the pawl beam 2330. The pawl spring 2332 can be curved away from the pawl beam 2330. A generally cylindrically shaped end piece 2342 can be formed at the end of the pawl spring. The pawl spring 2332 can be made of a material, thickness, and length such that the pawl spring 2332 is resiliently flexible so that it flexes as the pawl 2236 is displaced by the housing teeth 2224 when the knob member 2218 is rotated in the tightening direction. The pawl spring 2332 is shown in the relaxed position in FIGS. 77 and 78. In some embodiments, the pawl beam 2330 and the pawl spring 2332 are independently formed and then coupled to form the pawl 2236. Thus, pawl beam 2330 and pawl spring 2332 need not be formed of the same material. For example, a metal pawl beam 2330 may be advantageous because of its relatively high strength to thickness ratio while it may be advantageous to use a plastic pawl spring 2332. In some embodiments, the same material may be used in each, even when the beam pawl beam 2330 and the pawl spring 2332 are separately formed. In the illustrated embodiment of FIGS. 77-78, the pawl spring 2332 and the pawl beam 2330 can be integrally formed of the same material as a single piece, thereby simplifying the manufacturing and assembly cost and complexity. In some embodiments, different springs may be used than that shown in the illustrated embodiments. For example, a metal or plastic leaf spring or a wire coiled spring may be used in some applications.

Because the pawl beam 2330 and pawl spring 2332 are separate portions, the pawl spring 2332 can be altered to be more easily flexible (e.g., by making the pawl spring 2332 thinner) without reducing the amount of force the pawl beam 2330 is able to withstand as the knob member 2218 is twisted in the loosening direction. Likewise, the pawl beam 2330 can be altered so that it can withstand greater force applied to the knob 2218 in the loosening direction (e.g., by making the pawl beam 2330 thicker) without making the pawl spring 2332 less flexible. Thus, the pawl 2236 can be tuned to a desired level of flexibility and strength. For example, a pawl 2236 can be configured to withstand large amounts of force when the knob member 2218 is twisted in the loosening direction while also being easily radially displaceable when the knob member 2218 is rotated in the tightening direction. In some embodiments, the force applied to the pawl 2236 when the knob member 2218 is twisted in the loosening direction is born by the pawl beam 2330 and substantially none of the force is born by the pawl spring 2332. This configuration can be advantageous over embodiments in which a pawl includes a load bearing beam that also flexes to displace the pawl (e.g., during tightening), because the load bearing capability of the flexible pawl is reduced as the pawl is made more flexible, and the flexibility of the pawl is reduced as the beam is made to withstand higher forces. Thus, when using the flexible beam pawl, a sufficient amount of loosening force can cause the pawl beam to buckle, thereby compromising the lacing system. However, when using the pawls 2236, the pawl beam 2330 can be configured to be substantially rigid even when a relatively large loosening force is applied, and the pawl spring 2332 can be configured to allow the pawl beam 2330 to pivot easily when a tightening force is applied.

Figure 80:
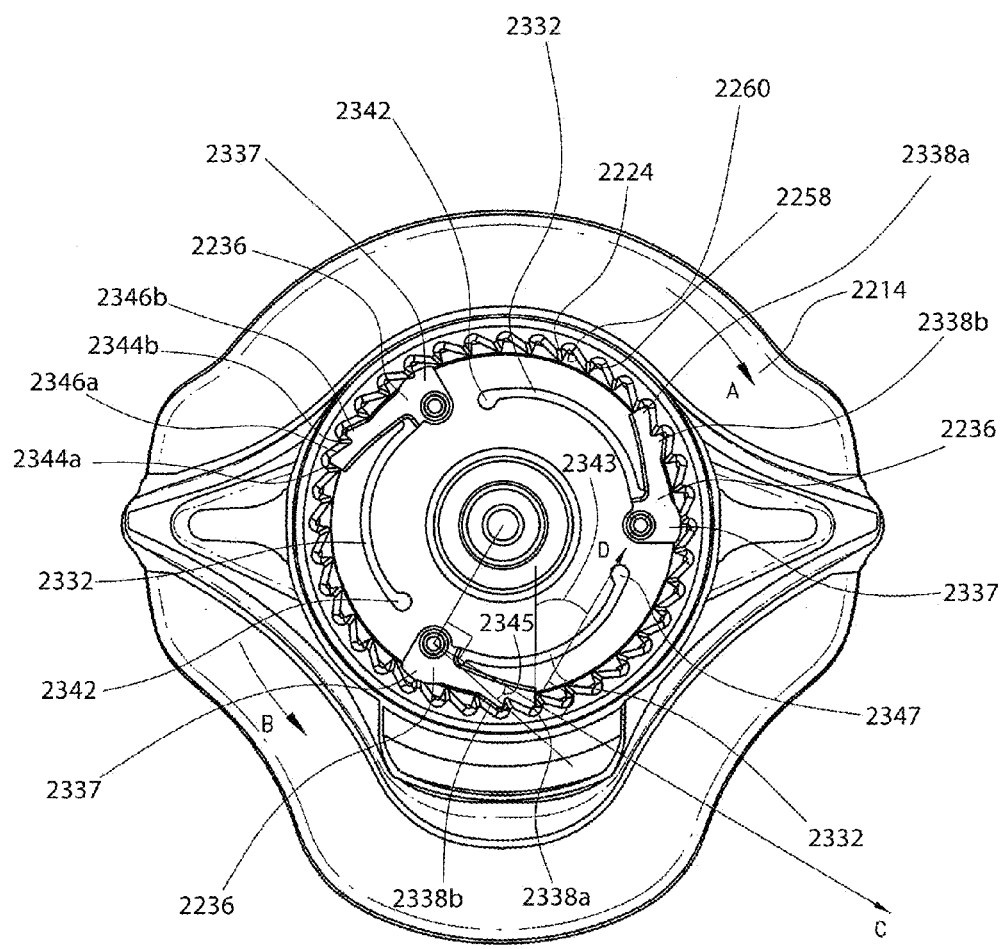
FIG. 80 is a top view of the pawls of FIG. 75 shown engaged with the housing teeth on the base member of FIG. 64.
Figure 81:
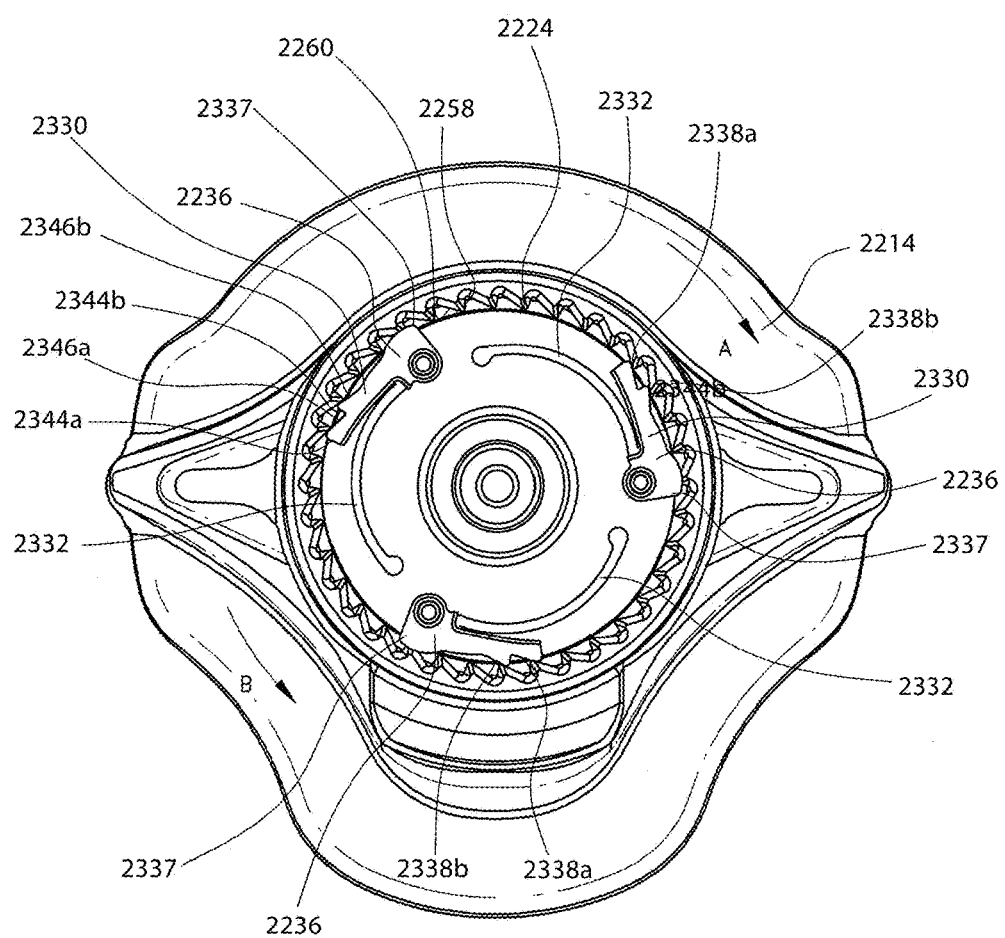
FIG. 81 is a top view of the pawls of FIG. 75 shown displaced radially inwardly as the knob member is rotated in the tightening direction.

FIG. 79 is a top view showing the pawls 2236 positioned inside of the pawl depressions 2324 of the knob core 2296. Although the housing 2220 is not shown in FIG. 79, the pawls 2236 are shown in the position where the pawl teeth 2338a-b are engaged with the housing teeth 2224. FIG. 80 is a top view showing the base member 2214 and the pawls 2236 in the same position as in FIG. 79 with the pawl teeth 2338a-b engaged with the housing teeth 2224. FIG. 81 is a top view of the base member 2214 and the pawls 2236 in a displaced configuration as the knob member 2218 is rotated in the tightening direction. The elements of the knob member 2218, other than the pawls 2236, and the spool member 2216 are omitted from the view shown in FIGS. 80 and 81 for simplicity.

In some embodiments, the pawl springs 2332 can be partially flexed to a position that is less curved than the relaxed position when inserted into the pawl depressions 2324. The flexed pawl springs 2332 can cause the pawls 2236 to tend to pivot so that the pawl beams 2330 are biased radially outwardly and so that the pawl teeth 2338a-b bear radially outwardly against the housing teeth 2224. When the knob member 2218 is twisted in the loosening direction (shown by arrow B) the first sides 2344a-b of the pawl teeth 2338a-b can bear against the first sides 2258 of the housing teeth 2224 to prevent the knob member 2218 from rotating in the loosening direction. In some embodiments, the pawl depressions 2324 can be configured to receive the pawls 2236 without the pawl springs 2332 needing to be partially flexed. Thus, in some embodiments, the pawl springs 2332 can be in the relaxed position when the pawl beams 2330 are engaged with the housing teeth 2224 to prevent the knob 2218 from loosening. When the pawl beams 2330 are displaced away from the housing teeth 2224, the pawl springs 2332 can transition from a relaxed to a flexed state such that the pawl beams 2330 are biased toward the housing teeth 2224. Also, as shown for example in FIG. 80, in some embodiments, one or more of the pawl teeth 2338a-b can engaged the housing teeth 2224 at locations that are radially outside a tangent line that extends from the pivot axis 2334 of the pawl 2236. In the embodiment of FIG. 80, the pawl tooth 2338b can engage the corresponding housing tooth 2224 at a location on a line that is angled radially outward from the tangent line C by an angle 2345 that is at least about 5° and/or less than or equal to about 15°, and can be about 10° in some embodiments. Thus, when a loosening force is applied to the knob member 2218 (shown by arrow B), a component of the force is directed to urge the pawl 2236 to pivot radially outwardly. Thus, as more loosening force is applied to the knob member 2218, the pawl teeth 2338a-b are urged to engage the housing teeth 2224 more firmly. This can prevent the pawls 2236 from unintentionally disengaging from the housing teeth 2224 when a large loosening force is applied. As the pawl 2236 is urged radially outward, the pawl beam can abut against the tips of one or more housing teeth 2224 not engaged by the pawl teeth 2338a-b, which can prevent the pawl beam 2330 from buckling outwardly and can transfer some of the loosening force into the housing. As discussed above, the surface 2328a of the pawl base 2328 can abut against the surface 2324a of the pawl depression 2324, thereby limiting the amount that the pawl 2236 can rotate radially outwardly.

In some embodiments, multiple pawl teeth 2338a-b can be used so that the multiple pawl teeth 2338a-b simultaneously engage multiple corresponding housing teeth 2224 so that, when the knob member 2218 is twisted in the loosening direction, the applied force is distributed across multiple teeth per pawl 2236 to prevent the knob member 2218 from rotating in the loosening direction. By distributing the force across multiple teeth, the housing teeth 2224 and pawl teeth 2338a-b can relatively small in size while still providing sufficient engagement surface area between the first sides 2258 of the housing teeth 2224 and the first sides 2344a-b of the pawl teeth 2338a-b. For example, the engagement of two pawl teeth 2338a-b with two consecutive housing teeth 2224 as shown can provide substantially the same engagement surface area for resisting rotation in the loosening direction as a single pawl tooth and housing tooth of twice the size shown. As the size of the housing teeth 2224 is reduced, the number of housing teeth 2224 can increase, and the tightening resolution of the reel 2204 can increase. When the knob member 2218 is advanced by one housing tooth 2224 in the tightening direction (shown by arrow A), the rotational distance that the knob member 2218 travels is reduced as the size of the housing teeth 2224 is reduced and the number of housing teeth 2224 is increased. Thus, by using more, and smaller, housing teeth 2224, the tightening resolution of the reel 2204 is increased so that the lacing system 2200 can be tightened more precisely to the desired level of tightness. Also, as the size of the housing teeth 2224 is reduced, the distance that the pawls 2236 are displaced in the radially inward direction when the knob member 2218 is tightened is also reduced, thereby making the knob member 2218 easier to rotate in the tightening direction. It is important to note that, in some embodiments, because the multiple pawl teeth 2338a-b are used, the knob member 2218 can be easily rotated in the tightening direction while strongly resisting rotation in the loosening direction. Although two pawl teeth 2338a-b are shown per pawl 2236, additional pawl teeth (e.g., three, four, five, or more) can be used, and, in some embodiments, a single pawl tooth can be used. As shown for example in FIG. 80, in some embodiments, one or more of the pawl teeth 2338a-b and the housing teeth 2224 can be configured to lock together when fully engaged, thereby preventing the pawl 2236 from rotating radially inward unless the knob member 2218 is moved in the tightening direction (shown by arrow A). The surface 2258 of the housing tooth 2224 and the surface 2344a of the pawl tooth 2338a can be form an angle 2343 (e.g., by at least about 5° and/or by less than or equal to about 15°, or by about 10°) from a line D, which can be perpendicular to the tangent line C for the pivot axis 2334 of the pawl 2236. The line D can be tangent to the arc tracked by the surface 2344a of the pawl tooth 2338a as it pivots radially inward. Since the surface 2258 of the housing tooth 2224 is angled towards the pawl beam 2330, the surface 2334a can abut against the surface 2258 when a force urges the surface 2334a to move in the direction of arrow D. Thus, when the pawl tooth 2338a fully engages the housing tooth 2224 such that the surface 2344a of the pawl tooth 2338a abuts against the surface 2258 of the housing tooth 2224, the pawl 2236 is prevented from rotating in the radially inward direction because radially inward rotation would cause the surface 2344a of the pawl tooth 2338a to press more firmly against the surface 2258 of the housing tooth 2224. The angled interface between the surfaces 2258 and 2344a can also provide a force on the pawl 2236 in the radially outward direction when a loosening force is applied (shown by arrow B). To allow the pawl 2236 to rotate radially inwardly, the pawl 2236 can be shifted in the tightening direction (shown by arrow A) so that the surface 2344a of the pawl tooth 2338a disengages from the surface 2258 of the housing tooth 2224. The other pawl teeth (e.g., pawl tooth 2338b) can operate similar to the pawl tooth 2338a to prevent unintentional disengagement of the pawls 2236.

When the knob member 2218 is rotated in the tightening direction (shown by arrow A), the second sides 2260 of the housing teeth 2224 can slide along the second sides 2346a-b of the pawl teeth 2338a-b, causing the pawls 2236 to rotate about the pivot axis (e.g., about the pivot tab 2336) so that the pawl beams 2330 are displaced radially inwardly away from the housing teeth 2224, as shown in FIG. 81. As the pawls 2236 rotate, the pawl springs 2232 can be further flexed, for example to a position that is less curved, and the end piece 2342 can slide along the wall of the pawl depression 2224 that is further away from the pawl base 2328. The curved edge of the generally cylindrically shaped end piece 2342 can provide a small contact area between the end piece 2342 and the wall of the pawl depression 2224 to reduce the amount of friction therebetween as the end piece 2342 slides. Once the tips of the pawl teeth 2338a-b pass the tips of the housing teeth 2224, the pawls 2236 can snap radially outwardly to a position similar to that shown in FIG. 80 except that the pawls 2236 are advance by one housing tooth 2224, or one step, in the tightening direction. To tighten the lacing system 2200, the user can rotate the knob member 2218 in the tightening direction by a desired amount, with the pawls 2236 snapping back after each step to prevent rotation in the loosening direction.

As can be seen in FIGS. 80 and 81, the flanges 2337 of the pawls 2236 can extend radially outwardly past the tips of the housing teeth 2224, but the flanges 2337 can be positioned near the tops of the pawls 2236 where the flanges 2337 do not contact the housing teeth 2224. Rather, the flanges 2337 can contact a portion of the wall 2325 of the pawl depressions 2324, as can be seen in FIG. 79. As the pawls 2236 rotate, the flanges 2337 can roll slightly against the wall of the pawl depressions 2324 to facilitate the desired rotational displacement of the pawls 2236. The mating of flange 2337 and wall portion 2325 can also assist in maintaining the general radial and axial position of the pawl 2236 in the pawl depression 2324.

The pawls 2236 can be configured differently than as shown in the illustrated embodiments. For example, in some embodiments, the flexible arm of the pawl spring 2332 can curve toward the pawl beam 2330 (e.g., in the opposite direction as that shown in the illustrated embodiments), and a middle portion of the curved arm of the pawl spring 2332 can ride along a wall of the corresponding depression 2324. In some embodiments, the curved arm can be configured so that it is more curved when in the more flexed position (e.g., when the pawl beam 2330 is displaced away from the housing teeth 2224) than when in the less flexed position (e.g., when the pawl beam 2330 is engaged with the housing teeth 2224). In some embodiments, the flexible arm can be attached to the pawl 2236 at locations other than that shown in the illustrated embodiment. For example, the flexible arm of the pawl spring 2332 can be extend from the end of the pawl beam 2330 that is furthest from the pivot tab 2336. Other variations are possible. Also, in some embodiments, the pawl spring 2332 can include a flexible arm that extends in generally the opposite direction as the pawl beam 2330, or generally radially inwardly, or in various other suitable directions so long as the pawl spring 2332 can be flexed to bias the pawl beam 2330 toward the housing teeth 2224. As discussed above, the pawl spring 2332 can also be made from a leaf spring, or a coil spring, or any other suitable biasing member configured to bias the pawl beam 2330 radially toward the housing teeth 2224.

Although various embodiments discussed herein include housing teeth 2224 that extend radially inwardly and pawls 2236 configured to be biased radially outwardly toward the housing teeth 2224, other configurations are possible. For example, the housing teeth 2224 can extend radially outwardly. The housing teeth 2224 can be formed, for example, on the outside surface of the shaft 2244 or similar structure. In these embodiments, the pawls 2236 can be configured to be biased radially inwardly toward the housing teeth 2224. In some embodiments it may be advantageous to position the housing teeth 2224 nearer to the periphery of the reel 2204 (e.g., as shown in the illustrated embodiments) so that the housing teeth 2224 are disposed along a larger circumference so that more housing teeth 2224 can be included, thereby increasing the tightening resolution (the number of teeth per revolution) of the reel 2204.

Figure 82:
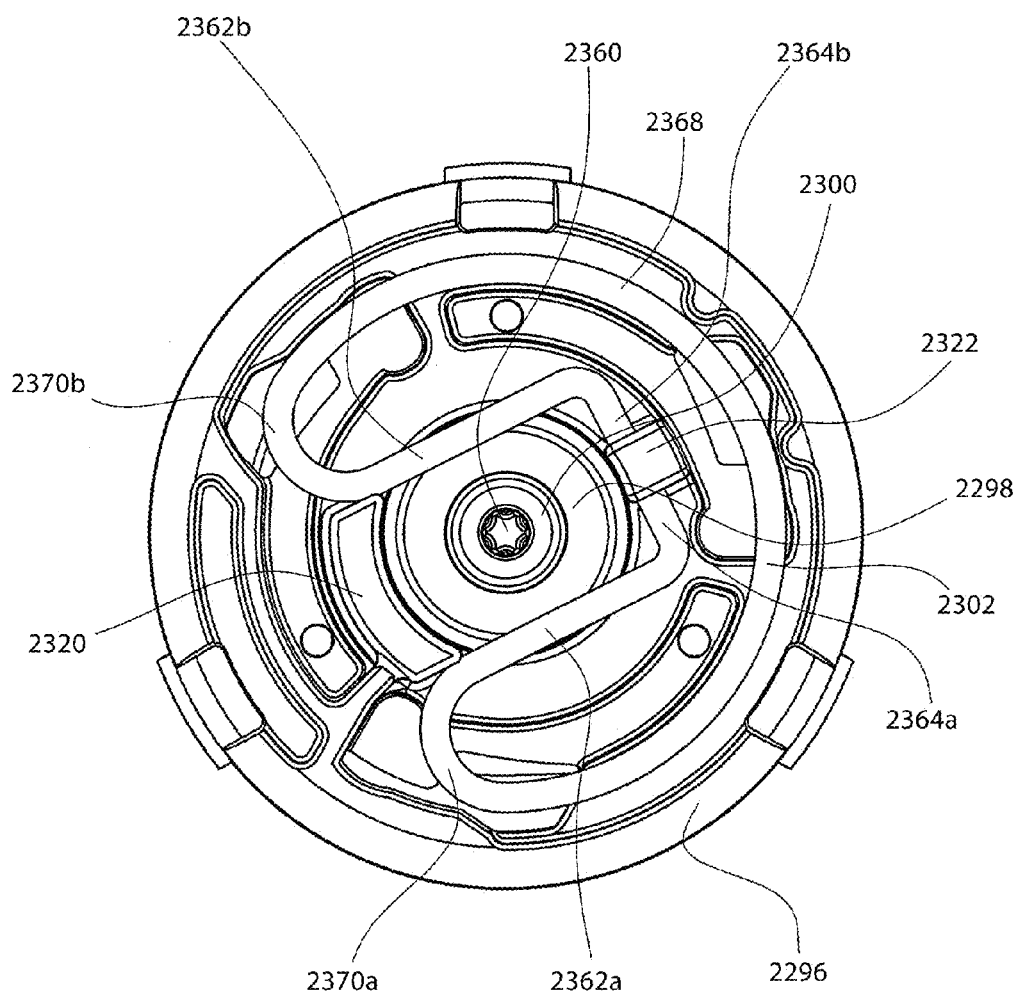
FIG. 82 is a top view of the spring bushing, fastener, and knob spring of FIG. 75 shown assembled with the knob core of FIG. 75.

FIG. 82 is a top view of the knob core 2296, the spring bushing 2298, the fastener 2300, and the knob spring 2302 in the assembled configurations. With reference now to FIGS. 75, 76, and 82, the spring bushing 2298 can be generally cylindrical in shape and can have a central opening 2348 formed through the center thereof. The outer surface of the spring busing 2298 can be wider at a top portion 2349 than at a bottom portion 2351, forming a step 2350 which can be configured to abut against the step 2318 formed in the central opening 2316 of the knob core 2296 when the spring bushing 2298 is fully inserted into the central opening 2316 of the knob core 2296. In the central opening 2348 that passes through the center of the spring bushing 2298, the upper portion can be wider than a lower portion, to form a step 2352.

The head 2354 of the fastener 2300 can abut against the step 2352 in the central opening of the spring bushing 2298 when the fastener 2300 is fully inserted into the central opening 2348 of the spring bushing 2298. The fastener 2300 can be a screw having a shaft 2356 that includes threads 2358 configured to engage the threads formed in the bore 2246 formed in the shaft 2244 of the housing. In some embodiments, the bore 2246 can include a threaded metal insert or a plastic thread molded as part of the bore 2246. In some embodiments, the bore 2246 does not have preformed threads, and the threads 2358 of the fastener 2300 can form the threads in the bore the first time that the fastener 2300 is inserted into the bore 2246. The head 2354 can include a notch 2360, which can be hexagonally or cross shaped, or otherwise configured to allow a screwdriver or other tool to turn the fastener 2300. In some embodiments, the knob member 2218 can be coupled to the housing 2220 in some other way, such as using a snap together fastener or rivet or ultrasonic welding. Other alternatives are possible.

The knob spring 2302 can include a pair of opposing engagement portions 2362a-b which can be configured to engage the spring bushing 2298. A pair of end pieces 2364a-b can extend approximately orthogonally from the engagement portions 2362a-b in an inward direction. An interconnecting portion 2368, which can be shaped to follow the partial circumference of a circle, can be attached to the engagement portions 2362a-b by curved connectors 2370a-b.

The knob spring 2302 can be secured to the knob core 2296. The wide engagement tab 2320 can be configured to fit between the curved connectors 2370a-b of the knob spring 2302, and the narrow engagement tab 2322 can be configured to fit between the end pieces 2364a-b of the knob spring 2302 to prevent the knob spring 2302 from rotating or otherwise moving with respect to the knob core 2296. In some embodiments, the wide engagement tab 2320 and/or the narrow engagement tab 2322 can be configured to receive the knob spring 2302 so that the knob spring 2302 is maintained in a slightly flexed configuration with the curved connectors 2370a-b bearing against the wide engagement tab 2320 and/or the end pieces 2364a-b bearing against the narrow engagement tab 2322. In some embodiments, the knob spring 2302 can be prevented from moving axially by the knob cover 2304 when it is attached to the knob core 2296.

The knob spring 2302 can be configured such that the engagement portions 2362a-b can be resiliently moved apart from one other to allow the upper wide portion 2349 of the spring bushing 2298 to pass between the engagement portions 2362a-b. The spring bushing 2298 can be in a disengaged position, as shown in FIG. 82, where the spring bushing 2298 is located below the engagement portions 2362a-b. In the engaged position, the upper wide portion 2349 of the spring bushing 2298 can be disposed above the engagement portions 2362a-b of the knob spring 2302. The upper wide portion 2349 of the spring bushing can be wider than the distance between the engagement portions 2362a-b of the knob spring 2302 to prevent the spring bushing from inadvertently transitioning between the engaged and disengaged positions. To transfer the spring bushing 2298 from the engaged to the disengaged positions, a force can be applied, for example by pulling the knob member 2218 in the axial direction away from the base member 2214, that causes the spring bushing 2298 to press down against the engagement portions 2362a-b causing the engagement portions 2362a-b to resiliently separate from one another until the upper wide portion 2359 of the spring bushing 2298 passes between the engagement portions 2362a-b. To transfer the spring bushing 2298 from the disengaged to the engaged positions, a force can be applied, for example by pushing the knob member 2218 in the axial direction toward the base member 2214, that causes the spring bushing 2298 to press up against the engagement portions 2362a-b causing the engagement portions 2362a-b to resiliently separate from one another until the upper wide portion 2359 of the spring bushing 2298 passes between the engagement portions 2362a-b.

Many variations are possible. For example, in some embodiments, the engagement portions 2362a-b can be maintained rigidly in place and the spring bushing 2298 can be made from a resiliently compressible material so that the spring bushing 2298 can transition between the engaged and disengaged positions by resiliently compressing and passing between the engagement portions 2362a-b. In some embodiments, the fastener 2300 and the spring bushing 2298 can be combined into a single piece. The knob spring 2302 can assume a variety of other shapes and can be attached to the knob core 2296 in a variety of other manners such that the engagement portions 2262a-b are configured to resiliently flex away from one another. The spring bushing 2298 can be formed in various other shapes than that shown in the illustrated embodiments. In some embodiments, the spring bushing 2298 can be rotationally asymmetrical and can rotate with the knob core 2296 and knob spring 2302. Thus, in some cases, the spring bushing 2298 can have flat sides that engage the knob spring 2302 along a line instead of just at a point.

With reference now to FIGS. 75 and 76, the knob cover 2304 can be generally disc shaped. The knob cover 2304 can have a domed or generally frustoconical top wall 2372 and a peripheral wall 2374 with a cavity 2376 formed therein. A central opening 2378 can be formed at the center of the top wall 2372 to allow a screwdriver or other tool to be inserted therethrough to engage the notch 2360 on the fastener 2300. The knob cover 2304 can include securing tabs 2380 and notches 2382 configured to engage the corresponding notches 2312 and protrusions 2314 on the knob core 2196 to secure the knob cover 2304 to the knob core 2296 using a snap-fit connection. The knob cover 2304 can be secured to the knob core 2296 in various other ways such as using an adhesive, a threaded connection, ultrasonic welding, or any other suitable manner. The knob cover 2304 can be either fixedly or removably attached to the knob core 2296. When the knob cover 2304 is attached to the knob core 2296, the pawls 2236, the spring bushing 2298, the fastener 2300, and the knob spring 2302 can be enclosed therebetween.

Top tabs 2384 can extend downward from the underside of the top wall 2372 of the knob cover 2304. The top tabs 2384 can align with the pivot tabs 2336 of the pawls 2236, and the bottom surfaces of the top tabs 2384 can contact, or nearly contact, the top surfaces of the pivot tabs 2336 of the pawls 2236 to thereby prevent the pawls from moving axially. Many variations are possible. In some embodiments, the pivot tabs 2336 of the pawls 2236 can fit into bores formed in the knob cover 2304 to secure the pawls 2236 and allow the pawls 2236 to pivot about the pivot tabs 2336.

A recess 2386 can be formed at the center of the cavity 2376, and the recess 2386 can be configured to receive the upper wide portion 2349 of the spring bushing 2298 when the spring bushing 2298 is in the engaged position.

The peripheral wall 2374 of the knob cover 2304 can include notches 2388 configured to receive corresponding tabs 2390 formed on the inside surface of the knob grip 2306. The knob grip 2306 can be generally doughnut shaped and can include raised portions 2392 and/or depressions 2394 on the outside surface to facilitate the gripping of the knob member 2218. In some embodiments, the knob grip 2306 can be omitted or can be divided into intermittent portions disposed about the periphery of the knob cover 2304. Other variations are possible.

An opening 2396 can be formed in a portion of the top wall 2372 of the knob cover 2304 to provide a view of some of the internal components of the reel 2204 during use, or to provide an exit path for water or other foreign material to exit the reel 2204. In some embodiments, the opening 2396 can be omitted.

Figure 83A:
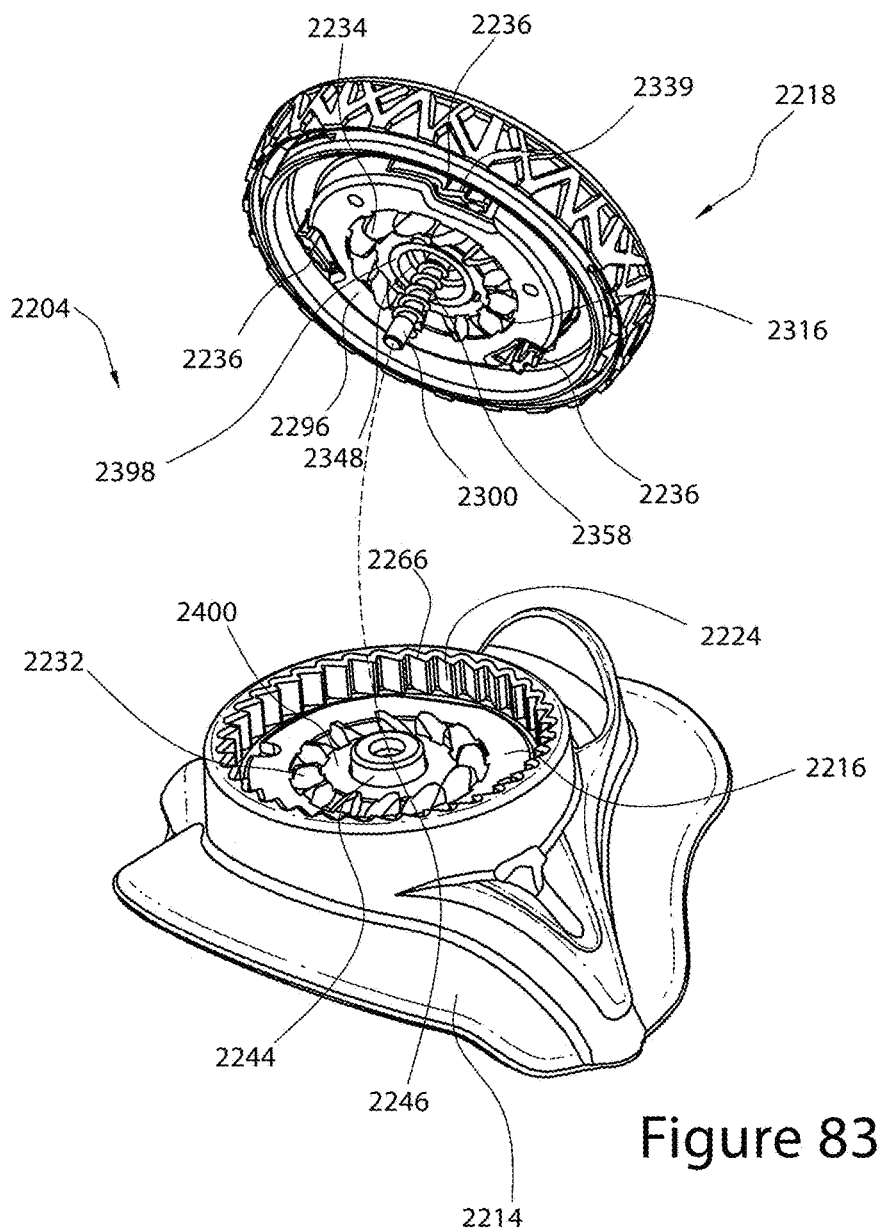
FIG. 83A is an exploded view of the reel of FIG. 64 shown in an engaged configuration.
Figure 83B:
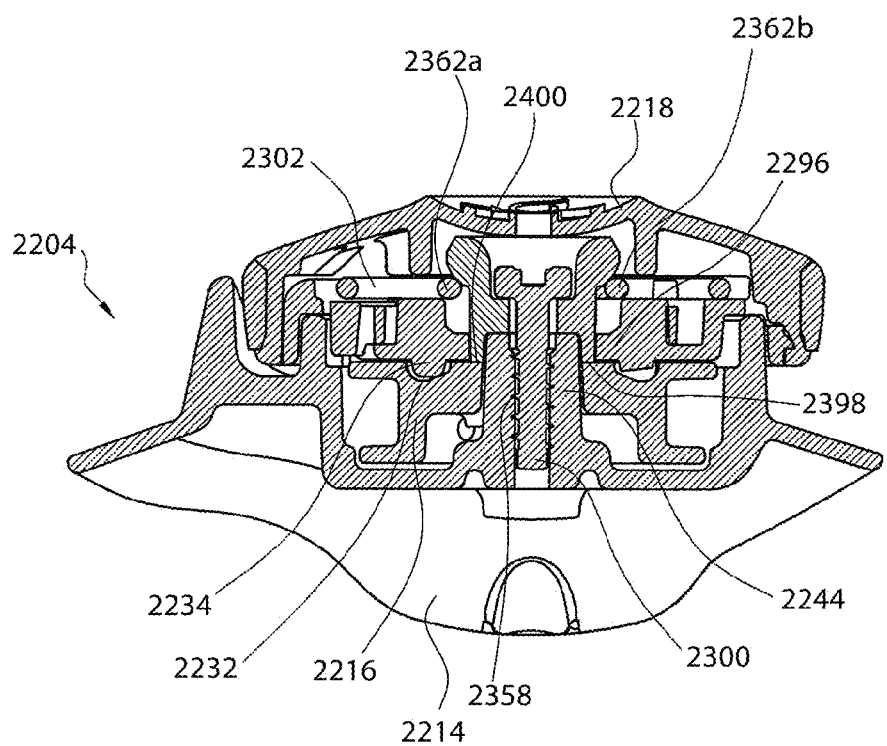
FIG. 83B is a cross sectional view of the reel of FIG. 64 shown in an engaged configuration.
Figure 84A:
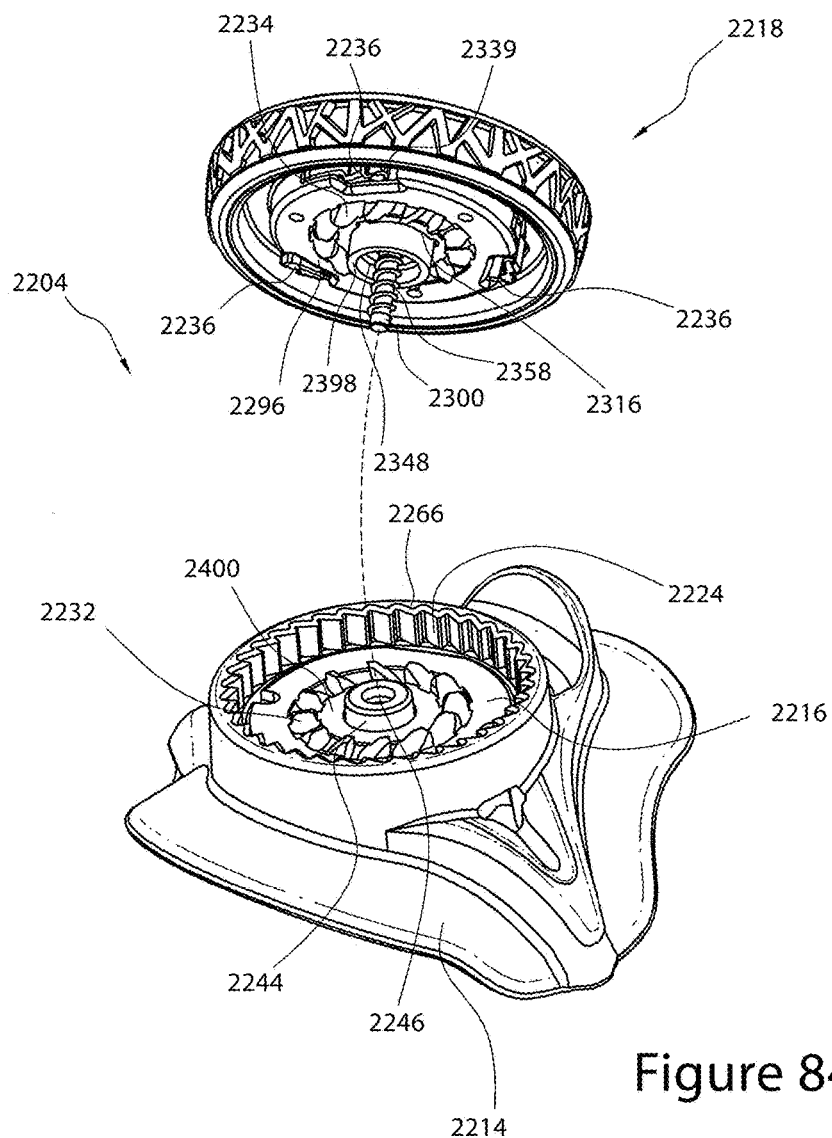
FIG. 84A is an exploded view of the reel of FIG. 64 shown in a disengaged configuration.
Figure 84B:
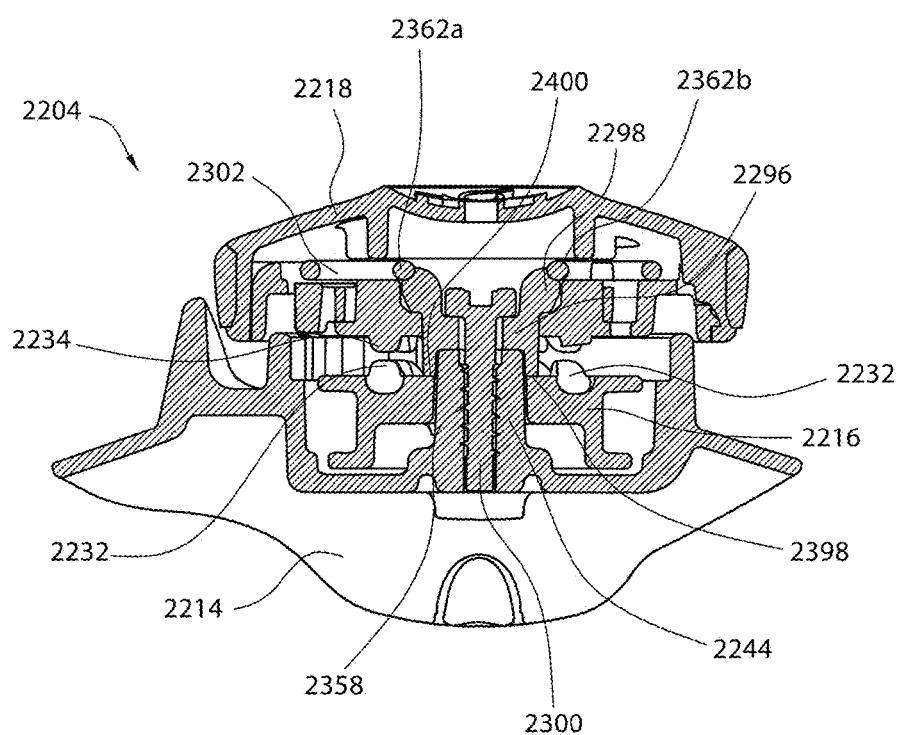
FIG. 84B is a cross sectional view of the reel of FIG. 64 shown in a disengaged configuration.

As mentioned above, the knob member 2218 can be axially movable between engaged and disengaged positions. FIG. 83A is an exploded view of the reel 2204 with the knob member 2218 in the engaged configuration. FIG. 83B is a cross sectional view of the reel 2204 with the knob member 2218 in the engaged configuration. FIG. 84A is an exploded view of the reel 2204 with the knob member 2218 in the disengaged configuration. FIG. 84B is a cross sectional view of the reel 2204 with the knob member 2218 in the disengaged configuration. The knob member 2218 can be secured to the base member 2214 by twisting the fastener 2300 so that the threads 2358 mate with corresponding threads in the bore 2246 formed in the shaft 2244. In some embodiments, when the fastener 2300 is sufficiently tightened, the portion of the shaft 2244 that extends up past the spool member 2216 can enter into a lower portion of the central opening 2348 formed through the spring bushing 2298. The bottom edge 2398 of the spring bushing 2298 can abut against, or nearly contact, the annular region 2400 inside of the spool teeth 2232.

When the knob member 2218 is in the engaged position, as shown in FIGS. 83A and 83B, the spring bushing 2298 and the fastener 2300 can be maintained in an raised position by the knob spring 2302, as discussed above, so that the bottom edge 2398 of the spring bushing 2298 does not extend past the central opening 2316 of the knob core 2296. Thus, the knob member 2218 is maintained in the lower engaged position (shown in dotted lines in FIG. 65), with the bottom of the knob core 2296 abutting against, or in close proximity to, the top surface of the spool member 2216. Thus, when in the engaged position, the knob teeth 2234 engage the spool teeth 2232, and the pawls 2236 engage the housing teeth 2224.

When the knob member 2218 is in the disengaged position, as shown in FIGS. 84A and 84B, the spring bushing 2298 and the fastener 2300 can be maintained in a lowered position by the knob spring 2302, as discussed above, so that the bottom edge 2398 of the spring bushing 2298 extends past the central opening 2316 of the knob core 2296 by at least about 1.0 mm and/or by no more than about 3.0 mm, and in some embodiments by about 2.25 mm, although other configurations outside these ranges are also possible. Since the bottom edge 2398 of the spring bushing 2298 continued to abut against, or nearly contact, the annular region 2400 of the spool member 2216, the knob member 2218 is raised away from the spool member 2216 and base member 2214 by an amount (e.g., about 2.25 mm) sufficient to cause the knob teeth 2234 to disengage from the spool teeth 2232 and/or to cause the pawls 2236 to disengage from the housing teeth 2224. In the embodiment shown, when the knob is in the disengaged position, the knob teeth 2234 disengage from the spool teeth 2232 and the pawls 2236 also disengage from the housing teeth 2224. Thus, in the illustrated disengaged configuration the spool member 2216 can be free to rotate in the loosening direction independent of the knob member 2218 to loosen the lacing system 2200, and the knob member 2218 can be free to rotate in both the tightening and loosening directions.

Many variations are possible. In some embodiments, when in the disengaged position, the knob teeth 2234 can disengage from the spool teeth 2232 while the pawls 2236 continue to engage the housing teeth 2224 (e.g., if the step 2340 shown in FIG. 77 were made larger so that the pawl teeth 2338a-b extended further downward). In these embodiments, the knob member 2218 can be impeded from rotating in the loosening direction even when in the disengaged position, but the spool member 2216 can be free to rotate in the loosening direction independent of the knob member 2218 to allow the lace 2206 to be withdrawn to loosen the lacing system 2200. In some embodiments, when in the disengaged position, the knob teeth 2234 can continue to engage the spool teeth 2232 (e.g., if the knob teeth 2234 and/or the spool teeth 2232 were made taller than in the illustrated embodiments) while the pawls 2236 can disengage from the housing teeth 2224. In these embodiments, the spool member 2216 continues to be coupled to the knob member 2218 even when in the disengaged position, but the knob member 2218 and spool member 2216 are permitted to rotated together in the loosening direction to release the lace 2206 from the reel 2204 to loosen the lacing system 2200. Other variations are also possible. For example, in some embodiments, the spool member 2216 can be integrally formed with, or fixedly attached to, or removably attached to the knob member 2218, and the spool teeth 2232 and knob teeth 2234 can be omitted.

As mentioned above, when in the disengaged position, the pawls 2236 can be raised sufficiently to disengage from the housing teeth 2224. In some embodiments, because the pawls are biased radially outwardly by the pawl springs 2232, the pawls 2236 can deflect radially outwardly so that portions of the bottom surfaces of the pawls 2236 are positioned above portions of the top surfaces of the housing teeth 2224. Thus in some embodiments, when the knob member 2218 is transitioned back to the engaged position, the pawls 2236 must be deflected radially inwardly so that they can reengage with the housing teeth 2224. As also mentioned above, at least a portion of the top surfaces 2266 of the housing teeth 2224 can be angled or beveled and/or at least a portion of the bottom surfaces 2339 of the pawls 2236 can be angled or beveled, so that the downward pressure applied when the knob member is returned to the engaged position can cause the pawls 2236 to deflect radially inwardly to facilitate the reengagement of the pawls 2236 with the housing teeth 2224. In some embodiments, the pawl depressions 2324 or other portions of the knob member 2218, can be configured to prevent the pawls 2236 from deflecting radially outwardly past the radial position where the pawls 2236 engage the housing teeth 2224, thereby reducing or eliminating the need to deflect the pawls 2236 inwardly when transitioning the knob member 2218 to the engaged position.

The knob member 2218 can be transitioned from the engaged position to the disengaged position by pulling the knob member 2218 axially away from the base member 2214 with enough force to cause the spring bushing 2298 to displace the knob spring 2302 and pass therethrough. To transition the knob member 2218 from the disengaged position to the engaged position the knob member 2218 can be pushed in the axial direction toward the base member 2214 with enough force to cause the spring bushing 2298 to displace the knob spring 2302 and pass therethrough.

The radial engagement of the pawls 2236 with the housing teeth 2224 can reduce or eliminate the occurrence of unintentionally transitioning the knob member 2218 from the engaged to disengaged positions by applying force to tend to twist the knob member 2218 in the loosening direction. If the lace 2206 is pulled, it can impart a force tending to twist the spool member 2216 in the loosening direction, and the force can be transferred to the knob 2218 via the spool teeth 2232 and knob teeth 2234, and the pawls 2236 can distributed the force radially among a certain number of the housing teeth 2224. Because the pawls 2236 engage the housing teeth radially, not axially, and because the pawls 2236 are configured to be displaced radially (when tightening the reel 2204), substantially none of the force is applied to the knob 2218 in the axial direction. Thus, the radial pawls 2236 do not impart any substantial force in the direction of the axial direction that would tend to separate the spool teeth 2232 from the knob teeth 2234 which can lead to unintentional disengagement of the knob member 2218 and/or unintentional loosening of the spool member 2216. Thus, the reel 2204 can be configured to withstand greater amounts of force applied to pull on the lace 2206 or applied to try and twist the knob member 2218 in the loosening direction without unintentionally causing the knob member 2218 to disengage than a reel 2204 in which the pawls axially engage the housing teeth and the pawls are configured to displace axially during tightening.

Also, in some embodiments, the force applied to the pawls 2236 when the knob 2218 is twisted in the loosening direction is born by the pawl beams 2330 such that substantially none of the force is transferred to the pawl springs 2332. Thus, the pawl springs 2332 can be configured to be easily flexible while the pawl beams 2330 can be configured to be substantially rigid. Therefore, the pawls 2236 can be configured to resist a relatively large amount of force applied to twist the knob member 2218 in the loosening direction because that force is born by the rigid pawl beams 2330, while the pawls can also be configured to rotate radially when a relatively small force is applied to twist the knob member 2218 in the tightening direction because that force is transferred to the flexible pawl springs 2332.

The components of the lacing systems described herein can be formed from any suitable material such as, but not limited to, plastic, carbon or other fiber reinforced plastic, aluminum, steel, rubber, or any other suitable material or combination of such materials. In some embodiments, the base member 2214, spool member 2216, knob core 2296, pawls 2236, spring bushing 2298, knob cover 2304, lace guides, or any other suitable components described herein can be injection molded or otherwise formed from any suitable polymeric material, such as nylon, PVC or PET. Some of the components described herein can be formed from a lubricious plastic such as PTFE, or other material useful in reducing the friction between a lace and such components as desired. Additionally, some of the components described herein can be coated or layered with a lubricious material to reduce the friction with interacting components or parts. The fastener 2300, and the knob spring 2302 can be made from a metal (e.g., aluminum or steel), but other materials can also be used such as plastics. The knob grip 2306 can be formed from rubber, or latex, or silicon, or any other material to facilitate the gripping of the knob member 2218.

Figure 85:
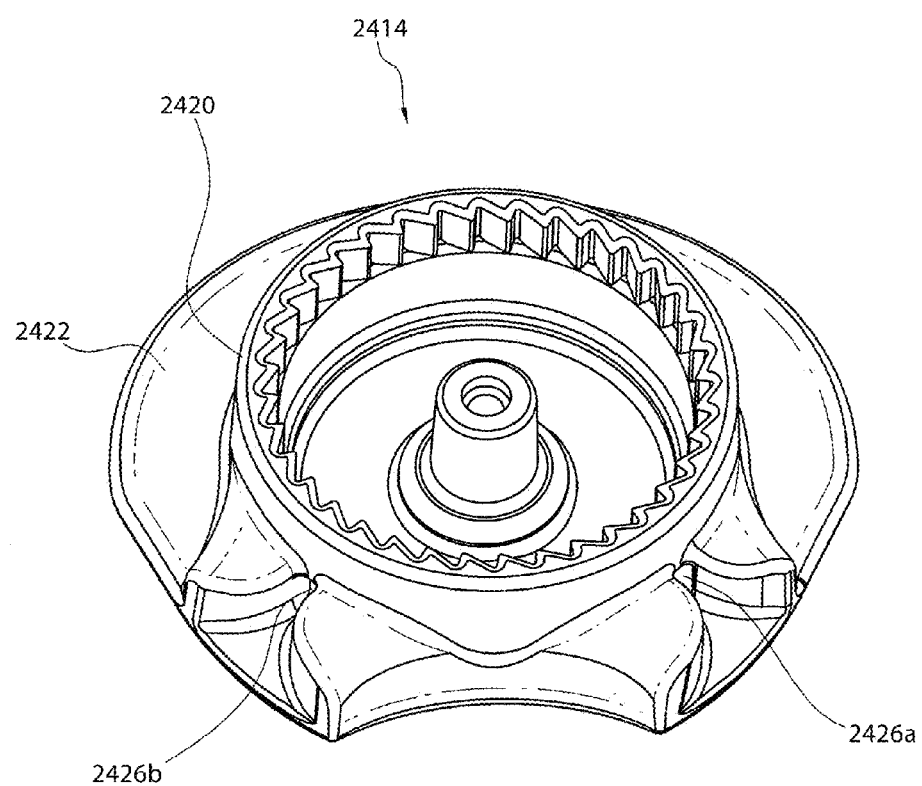
FIG. 85 is a perspective view of an alternative embodiment of a base member that can be used in place of the base member of FIG. 64.

FIG. 85 is a perspective view of an alternative embodiment of a base member 2414 which can be used in place of the base member 2214 discussed above. The base member 2414 can include a housing 2420 and a mounting flange 2422 and can be generally similar to the base member 2214 described above, except that the lace holes 2426a-b can be configured to direct the lace generally radially away from the base member 2414 rather than axially away from the base member 2214 as shown, for example, in FIG. 62. Also, the lace holes 2426a-b are placed generally on the same side of the base member 2414, rather than on opposite ends as in the base member 2214 discussed above. Many variations are possible depending on the particular application to which the lacing system is applied. For example, in some embodiments, the base member can include only one lace hole and only one end of the lace can enter the housing and attach to the spool member. In these embodiments, the other end of the lace can attach to the base member or to the article being tightened.

Figure 86:
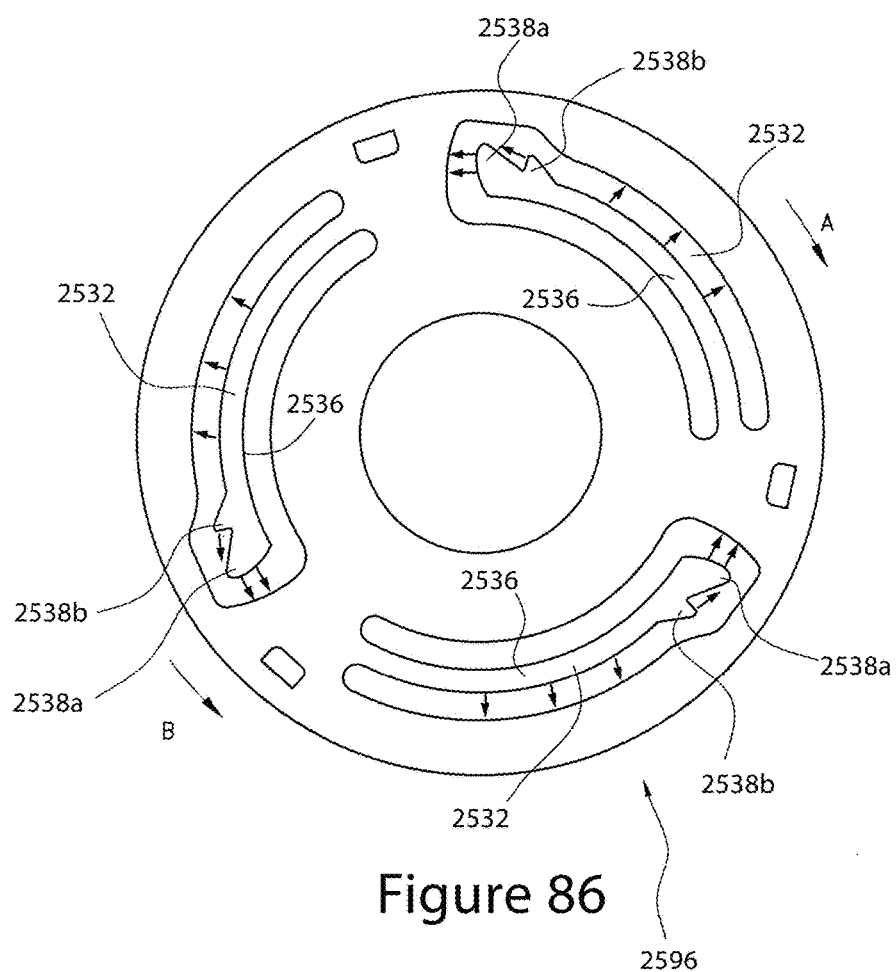
FIG. 86 is a cross sectional view of an alternative embodiment of a knob core.

FIG. 86 is a cross sectional view of another embodiment of a knob core 2596 which can be used in a reel that can be similar in many ways to the reel 2204 described herein. The knob core 2596 can include pawls 2536 which can be integrally formed with the knob core 2596 to simplify construction and assembly of the reel. In other embodiments, the pawls 2536 can be attached to the knob core 2596 in any suitable manner. The pawls 2536 can include pawl arms 2532 which can be made of a material, thickness, and length so as to be flexible to allow the pawls 2536 to be displaced radially inwardly by housing teeth as the knob core 2596 is rotated in the tightening direction (shown by arrow A) in a manner similar to that described above. The pawls 2536 can include pawl teeth 2538a-b formed at the ends of the pawl arms 2532. In the illustrated embodiment two pawl teeth 2538a-b are used per pawl 2536, but any other suitable number of pawl teeth 2538a-b can be used.

When the knob core 2596 is twisted in the loosening direction (shown by arrow B), the pawl teeth 2538a-b can bear against housing teeth (not shown in FIG. 86) to prevent the knob core 2596 from rotating in the loosening direction. The force arrows drawn in FIG. 86 illustrate the directions in which the force is distributed radially. As the pawl teeth 2538a-b bear against the housing teeth, a force is applied from the pawl teeth 2538a-b to the housing teeth as shown. The pawl arms 2532 can be curved as shown so that, when the pawl teeth 2538a-b bear against the housing teeth, the pawl arms 2532 tend to flex or buckle radially outwardly as shown by arrows in FIG. 86. The pawls 2536 can be configured such that the housing teeth abut against the pawl arms 2532 such that, as the pawl arms 2532 attempt to flex or buckle radially outwardly, they bear against the tips of the housing teeth, distribute the force radially to the housing teeth, and are prevented from buckling. In some embodiments, the housing teeth can substantially prevented the pawl arms 2532 from moving radially outwardly. Because pawls 2536 engage the housing teeth radially, not axially, and because the pawls 2536 are configured to be displaced radially, not axially, during tightening, substantially none of the force applied when twisting in the loosening direction is applied axially thereby reducing or eliminating the occurrence of unintentional axial movement of the knob core 2596 from the engaged position to the disengage position.

Although the disclosure is discussed in terms of certain embodiments, it should be understood that the disclosure is not limited to the embodiments specifically shown and discussed. The embodiments are explained herein by way of example, and there are numerous modifications, variations, and other embodiments that may be employed within the scope of the present inventions. Components can be added, removed, and/or rearranged both with the individual embodiments discussed herein and between the various embodiments. For purposes of this disclosure, certain aspects, advantages, and novel features are described herein. It should be understood that not necessarily all such advantages may be achieved in accordance with any particular embodiment. Thus, for example, those of skill in the art will recognize that the inventions may be embodied or carried out in a manner that achieves one advantage or a group of advantages at taught or suggested herein without necessarily achieving other advantages as may be taught or suggested herein.

Although various embodiments of lacing systems are described herein, the various components, features, or other aspects of the embodiments of the lacing systems described herein can be combined or interchanged to form additional embodiments of lacing systems not explicitly described herein, all of which are contemplated as being a part of the present disclosure. In addition, while a number of variations have been shown and described in detail, other modifications, which are within the scope of the this disclosure, will be readily apparent to those of skill in the art based upon this disclosure. Thus, it is intended that the scope of the disclosure should not be limited by the particular disclosed embodiments described above.

What is claimed is:

1. An article comprising:
   a base material;
   a tightening mechanism coupled to the base material, the tightening mechanism comprising a rotatable knob;
   a tension member operably coupled with the tightening mechanism such that rotation of the knob in a tightening direction tensions the tension member and tightens the article; and
   a strip or segment of resilient material positioned about the base material and coupled therewith so that a portion of the strip or segment of resilient material is disposed over the tightening mechanism to exert a pressure or force on the tightening mechanism that is directed toward the base material;
   wherein opposing ends of the strip or segment of resilient material are coupled with the base material so that a mid-portion of the strip or segment of resilient material is positioned over the tightening mechanism and covers opposing peripheral sides of the tightening mechanism.

2. The article of claim 1, wherein the base material comprises a hole and at least a portion of the tightening mechanism extends through the hole in the base material.

3. The article of claim 1, wherein the article is a shoe and wherein the tightening mechanism and the strip or segment of resilient material are coupled with a heel portion of the shoe.

4. The article of claim 1, wherein the strip or segment of resilient material is positioned over the tightening mechanism so that at least a portion of the tightening mechanism is exposed.

5. The article of claim 4, wherein the strip or segment of resilient material is positioned over the tightening mechanism so that opposing lateral sides of the tightening mechanism are exposed for grasping and rotation by a user.

6. The article of claim 1, wherein the strip or segment of resilient material enables the knob to be pulled axially outward from the article.

7. The article of claim 6, wherein the force or pressure applied by the strip or segment of resilient material is sufficient to cause the knob to return to an axially inward position after the knob is released by a user.

8. A method of making an article comprising:
   providing a base material;
   coupling a tightening mechanism to the base material, the tightening mechanism comprising a rotatable knob;
   positioning a tension member about the article and operationally coupling the tension member with the tightening mechanism such that rotation of the knob in a tightening direction tensions the tension member and tightens the article; and
   coupling opposing ends of a strip or segment of resilient material with the base material so that a mid-portion of the strip or segment of resilient material is disposed over the tightening mechanism and covers opposing peripheral sides of the tightening mechanism and so that the mid-portion of the strip or segment of resilient material exerts a pressure or force on the tightening mechanism that is directed toward the base material.

9. The method of claim 8, wherein the base material comprises a hole and wherein coupling the tightening mechanism to the base material comprises positioning the tightening mechanism such that at least a portion of the tightening mechanism extends through the hole in the base material.

10. The method of claim 8, wherein the strip or segment of resilient material enables the knob to be pulled axially outward from the article.

11. The method of claim 8, wherein the mid-portion of the strip or segment of resilient material is disposed over the tightening mechanism so that opposing lateral sides of the tightening mechanism are exposed for grasping and rotation by a user.

* * * * *